United States Patent
Gieffers et al.

(10) Patent No.: US 10,844,108 B2
(45) Date of Patent: Nov. 24, 2020

(54) SINGLE-CHAIN CD27-RECEPTOR AGONIST PROTEINS

(71) Applicant: Apogenix AG, Heidelberg (DE)

(72) Inventors: Christian Gieffers, Dossenheim (DE);
Oliver Hill, Neckarsteinach (DE);
Meinolf Thiemann, Schriesheim (DE);
Tim Schnyder, Igersheim (DE)

(73) Assignee: Apogenix AG, Heidelberg (DE)

( * ) Notice: Subject to any disclaimer, the term of this patent is extended or adjusted under 35 U.S.C. 154(b) by 130 days.

(21) Appl. No.: 15/956,964

(22) Filed: Apr. 19, 2018

(65) Prior Publication Data

US 2018/0244751 A1 Aug. 30, 2018

Related U.S. Application Data

(63) Continuation of application No. PCT/EP2016/075579, filed on Oct. 24, 2016.

(60) Provisional application No. 62/245,689, filed on Oct. 23, 2015.

(51) Int. Cl.
*C07K 14/705* (2006.01)
*C07K 16/28* (2006.01)
*A61K 38/00* (2006.01)

(52) U.S. Cl.
CPC .... *C07K 14/70575* (2013.01); *C07K 16/2809* (2013.01); *C07K 16/2818* (2013.01); *A61K 38/00* (2013.01); *C07K 2319/00* (2013.01); *C07K 2319/22* (2013.01); *C07K 2319/30* (2013.01); *C07K 2319/32* (2013.01); *C07K 2319/35* (2013.01); *C07K 2319/74* (2013.01)

(58) Field of Classification Search
CPC .......... C07K 14/70575; C07K 16/2818; C07K 2319/00; C07K 2319/74; C07K 2319/30; A61K 38/00
See application file for complete search history.

(56) References Cited

U.S. PATENT DOCUMENTS 9,908,927 B2  3/2018  Hill et al.

FOREIGN PATENT DOCUMENTS

| WO | 01/25277 A1 | 4/2001 |
|---|---|---|
| WO | 01/49866 A1 | 7/2001 |
| WO | 02/09055 A1 | 1/2002 |
| WO | 2004085478 A2 | 10/2004 |
| WO | 2005103077 A1 | 11/2005 |
| WO | 2010/010051 | 1/2010 |
| WO | 2015164588 A1 | 10/2015 |

OTHER PUBLICATIONS

Carine Cormary et al, "Induction of T-cell antitumor immunity and protection against tumor growth by secretion of soluble human CD70 molecules", Cancer Gene Therapy, May 21, 2004, pp. 497-507, vol. 11, No. 7.
Tania F. Rowley et al, "Stimulation by Soluble CD70 Promotes Strong Primary and Secondary CD8+ Cytotoxic T Cell Responses In Vivo", The Journal of Immunology, May 15, 2004, pp. 6039-6046, vol. 172, No. 10, US.
Agnes Wyzgol, "Generierung and Charakterisierung rekombinanter TNF-Liganden" Jan. 1, 2012. English summary included.
International Search Report and Written Opinion of the International Searching Authority dated Jan. 17, 2017 issued in PCT/EP2016/075579.
Tetsuya Shiraishi, et al., "Increased cytotoxicity of soluble Fas ligand by fusing isoleucine zipper motif", Biochemical and Biophysical Research Communications 322 (2004) 197-202.
Li-Zhen He, et al., "Agonist Anti-Human CD27 Monoclonal Antibody Induces T Cell Activation and Tumor Immunity in Human CD27-Transgenic Mice", The Journal of Immunology, Sep. 11, 2013, 191: 4174-4183.
Pascal Schneider, et al., "Conversion of Membrane-bound Fas(CD95) Ligand to Its Soluble Form Is Associated with Downregulation of Its Proapoptotic Activity and Loss of Liver Toxicity", J. Exp. Med., vol. 187, No. 8, Apr. 20, 1998, pp. 1205-1213.

Primary Examiner — Ruixiang Li
(74) Attorney, Agent, or Firm — Perkins Coie LLP; Viola Kung

(57) ABSTRACT

Provided herein are specific CD27 receptor agonist proteins, nucleic acids encoding the same, and methods of treating a subject having a CD27L-associated disease or disorder. The CD27 receptor agonist proteins provided herein comprise three soluble CD27L domains an and Fc fragment. The CD27 receptor agonist proteins are substantially non-aggregating and suitable for therapeutic, diagnostic and/or research applications.

16 Claims, 10 Drawing Sheets

Specification includes a Sequence Listing.

SEQUENCE LISTING

<160> NUMBER OF SEQ ID NOS: 47

<210> SEQ ID NO 1
<211> LENGTH: 193
<212> TYPE: PRT
<213> ORGANISM: Homo sapiens
<220> FEATURE:
<223> OTHER INFORMATION: CD27 ligand (wt)

<400> SEQUENCE: 1

Met Pro Glu Glu Gly Ser Gly Cys Ser Val Arg Arg Pro Tyr Gly
1               5                   10                  15

Cys Val Leu Arg Ala Ala Leu Val Pro Leu Val Ala Gly Leu Val Ile
                20                  25                  30

Cys Leu Val Val Cys Ile Gln Arg Phe Ala Gln Ala Gln Gln Gln Leu
            35                  40                  45

Pro Leu Glu Ser Leu Gly Trp Asp Val Ala Glu Leu Gln Leu Asn His
    50                  55                      60

Thr Gly Pro Gln Gln Asp Pro Arg Leu Tyr Trp Gln Gly Gly Pro Ala
65                  70                  75                  80

Leu Gly Arg Ser Phe Leu His Gly Pro Glu Leu Asp Lys Gly Gln Leu
                85                  90                  95

Arg Ile His Arg Asp Gly Ile Tyr Met Val His Ile Gln Val Thr Leu
            100                 105                 110

Ala Ile Cys Ser Ser Thr Thr Ala Ser Arg His His Pro Thr Thr Leu
            115                 120                 125

Ala Val Gly Ile Cys Ser Pro Ala Ser Arg Ser Ile Ser Leu Leu Arg
            130                 135                 140

Leu Ser Phe His Gln Gly Cys Thr Ile Ala Ser Gln Arg Leu Thr Pro
145                 150                 155                 160

Leu Ala Arg Gly Asp Thr Leu Cys Thr Asn Leu Thr Gly Thr Leu Leu
                165                 170                 175

Pro Ser Arg Asn Thr Asp Glu Thr Phe Phe Gly Val Gln Trp Val Arg
                180                 185                 190

Pro

<210> SEQ ID NO 2
<211> LENGTH: 8
<212> TYPE: PRT
<213> ORGANISM: Artificial Sequence
<220> FEATURE:
<223> OTHER INFORMATION: linker

<400> SEQUENCE: 2

Gly Ser Gly Ser Gly Asn Gly Ser
1               5

<210> SEQ ID NO 3
<211> LENGTH: 8
<212> TYPE: PRT
<213> ORGANISM: Artificial Sequence
<220> FEATURE:
<223> OTHER INFORMATION: linker

<400> SEQUENCE: 3

Gly Ser Gly Ser Gly Ser Gly Ser
1               5

<210> SEQ ID NO 4
<211> LENGTH: 8
<212> TYPE: PRT
<213> ORGANISM: Artificial Sequence
<220> FEATURE:
<223> OTHER INFORMATION: linker

<400> SEQUENCE: 4

Gly Gly Ser Gly Ser Gly Ser Gly
1               5

```
<210> SEQ ID NO 5
<211> LENGTH: 6
<212> TYPE: PRT
<213> ORGANISM: Artificial Sequence
<220> FEATURE:
<223> OTHER INFORMATION: linker

<400> SEQUENCE: 5

Gly Gly Ser Gly Ser Gly
1               5

<210> SEQ ID NO 6
<211> LENGTH: 4
<212> TYPE: PRT
<213> ORGANISM: Artificial Sequence
<220> FEATURE:
<223> OTHER INFORMATION: linker

<400> SEQUENCE: 6

Gly Gly Ser Gly
1

<210> SEQ ID NO 7
<211> LENGTH: 8
<212> TYPE: PRT
<213> ORGANISM: Artificial Sequence
<220> FEATURE:
<223> OTHER INFORMATION: linker

<400> SEQUENCE: 7

Gly Gly Ser Gly Asn Gly Ser Gly
1               5

<210> SEQ ID NO 8
<211> LENGTH: 8
<212> TYPE: PRT
<213> ORGANISM: Artificial Sequence
<220> FEATURE:
<223> OTHER INFORMATION: linker

<400> SEQUENCE: 8

Gly Gly Asn Gly Ser Gly Ser Gly
1               5

<210> SEQ ID NO 9
<211> LENGTH: 6
<212> TYPE: PRT
<213> ORGANISM: Artificial Sequence
<220> FEATURE:
<223> OTHER INFORMATION: linker

<400> SEQUENCE: 9

Gly Gly Asn Gly Ser Gly
1               5

<210> SEQ ID NO 10
<211> LENGTH: 6
<212> TYPE: PRT
<213> ORGANISM: Artificial Sequence
<220> FEATURE:
<223> OTHER INFORMATION: linker

<400> SEQUENCE: 10

Gly Ser Gly Ser Gly Ser
1               5
```

```
<210> SEQ ID NO 11
<211> LENGTH: 4
<212> TYPE: PRT
<213> ORGANISM: Artificial Sequence
<220> FEATURE:
<223> OTHER INFORMATION: linker

<400> SEQUENCE: 11

Gly Ser Gly Ser
1

<210> SEQ ID NO 12
<211> LENGTH: 3
<212> TYPE: PRT
<213> ORGANISM: Artificial Sequence
<220> FEATURE:
<223> OTHER INFORMATION: linker

<400> SEQUENCE: 12

Gly Ser Gly
1

<210> SEQ ID NO 13
<211> LENGTH: 218
<212> TYPE: PRT
<213> ORGANISM: Artificial Sequence
<220> FEATURE:
<223> OTHER INFORMATION: human IGG1 Fc N297S

<400> SEQUENCE: 13

Pro Ala Pro Glu Leu Leu Gly Gly Pro Ser Val Phe Leu Phe Pro Pro
1               5                   10                  15

Lys Pro Lys Asp Thr Leu Met Ile Ser Arg Thr Pro Glu Val Thr Cys
            20                  25                  30

Val Val Val Asp Val Ser His Glu Asp Pro Glu Val Lys Phe Asn Trp
        35                  40                  45

Tyr Val Asp Gly Val Glu Val His Asn Ala Lys Thr Lys Pro Arg Glu
    50                  55                  60

Glu Gln Tyr Ser Ser Thr Tyr Arg Val Val Ser Val Leu Thr Val Leu
65                  70                  75                  80

His Gln Asp Trp Leu Asn Gly Lys Glu Tyr Lys Cys Lys Val Ser Asn
                85                  90                  95

Lys Ala Leu Pro Ala Pro Ile Glu Lys Thr Ile Ser Lys Ala Lys Gly
            100                 105                 110

Gln Pro Arg Glu Pro Gln Val Tyr Thr Leu Pro Pro Ser Arg Glu Glu
        115                 120                 125

Met Thr Lys Asn Gln Val Ser Leu Thr Cys Leu Val Lys Gly Phe Tyr
    130                 135                 140

Pro Ser Asp Ile Ala Val Glu Trp Glu Ser Asn Gly Gln Pro Glu Asn
145                 150                 155                 160

Asn Tyr Lys Thr Thr Pro Pro Val Leu Asp Ser Asp Gly Ser Phe Phe
                165                 170                 175

Leu Tyr Ser Lys Leu Thr Val Asp Lys Ser Arg Trp Gln Gln Gly Asn
            180                 185                 190

Val Phe Ser Cys Ser Val Met His Glu Ala Leu His Asn His Tyr Thr
        195                 200                 205

Gln Lys Ser Leu Ser Leu Ser Pro Gly Lys
    210                 215

<210> SEQ ID NO 14
```

```
<211> LENGTH: 217
<212> TYPE: PRT
<213> ORGANISM: Artificial Sequence
<220> FEATURE:
<223> OTHER INFORMATION: human IGG1 Fc (wt)

<400> SEQUENCE: 14

Pro Ala Pro Pro Val Ala Gly Pro Ser Val Phe Leu Phe Pro Pro Lys
1               5                   10                  15

Pro Lys Asp Thr Leu Met Ile Ser Arg Thr Pro Glu Val Thr Cys Val
            20                  25                  30

Val Val Asp Val Ser His Glu Asp Pro Glu Val Lys Phe Asn Trp Tyr
        35                  40                  45

Val Asp Gly Val Glu Val His Asn Ala Lys Thr Lys Pro Arg Glu Glu
    50                  55                  60

Gln Tyr Asn Ser Thr Tyr Arg Val Val Ser Val Leu Thr Val Leu His
65                  70                  75                  80

Gln Asp Trp Leu Asn Gly Lys Glu Tyr Lys Cys Lys Val Ser Asn Lys
                85                  90                  95

Gly Leu Pro Ser Ser Ile Glu Lys Thr Ile Ser Lys Ala Lys Gly Gln
            100                 105                 110

Pro Arg Glu Pro Gln Val Tyr Thr Leu Pro Pro Ser Arg Glu Glu Met
        115                 120                 125

Thr Lys Asn Gln Val Ser Leu Thr Cys Leu Val Lys Gly Phe Tyr Pro
    130                 135                 140

Ser Asp Ile Ala Val Glu Trp Glu Ser Asn Gly Gln Pro Glu Asn Asn
145                 150                 155                 160

Tyr Lys Thr Thr Pro Pro Val Leu Asp Ser Asp Gly Ser Phe Phe Leu
                165                 170                 175

Tyr Ser Lys Leu Thr Val Asp Lys Ser Arg Trp Gln Gln Gly Asn Val
            180                 185                 190

Phe Ser Cys Ser Val Met His Glu Ala Leu His Asn His Tyr Thr Gln
        195                 200                 205

Lys Ser Leu Ser Leu Ser Pro Gly Lys
    210                 215

<210> SEQ ID NO 15
<211> LENGTH: 718
<212> TYPE: PRT
<213> ORGANISM: Artificial Sequence
<220> FEATURE:
<223> OTHER INFORMATION: PROTEIN A (CD27L fused to deglyco Fc)

<400> SEQUENCE: 15

Met Glu Thr Asp Thr Leu Leu Val Phe Val Leu Leu Val Trp Val Pro
1               5                   10                  15

Ala Gly Asn Gly Glu Ser Leu Gly Trp Asp Val Ala Glu Leu Gln Leu
            20                  25                  30

Asn His Thr Gly Pro Gln Gln Asp Pro Arg Leu Tyr Trp Gln Gly Gly
        35                  40                  45

Pro Ala Leu Gly Arg Ser Phe Leu His Gly Pro Glu Leu Asp Lys Gly
    50                  55                  60

Gln Leu Arg Ile His Arg Asp Gly Ile Tyr Met Val His Ile Gln Val
65                  70                  75                  80

Thr Leu Ala Ile Cys Ser Ser Thr Thr Ala Ser Arg His His Pro Thr
                85                  90                  95

Thr Leu Ala Val Gly Ile Cys Ser Pro Ala Ser Arg Ser Ile Ser Leu
```

```
                100             105             110
Leu Arg Leu Ser Phe His Gln Gly Cys Thr Ile Ala Ser Gln Arg Leu
            115                 120                 125
Thr Pro Leu Ala Arg Gly Asp Thr Leu Cys Thr Asn Leu Thr Gly Thr
        130                 135                 140
Leu Leu Pro Ser Arg Asn Thr Asp Glu Thr Phe Phe Gly Val Gln Trp
145                 150                 155                 160
Val Arg Pro Gly Ser Gly Ser Gly Asn Gly Ser Glu Ser Leu Gly Trp
                165                 170                 175
Asp Val Ala Glu Leu Gln Leu Asn His Thr Gly Pro Gln Gln Asp Pro
            180                 185                 190
Arg Leu Tyr Trp Gln Gly Gly Pro Ala Leu Gly Arg Ser Phe Leu His
        195                 200                 205
Gly Pro Glu Leu Asp Lys Gly Gln Leu Arg Ile His Arg Asp Gly Ile
    210                 215                 220
Tyr Met Val His Ile Gln Val Thr Leu Ala Ile Cys Ser Ser Thr Thr
225                 230                 235                 240
Ala Ser Arg His His Pro Thr Thr Leu Ala Val Gly Ile Cys Ser Pro
                245                 250                 255
Ala Ser Arg Ser Ile Ser Leu Leu Arg Leu Ser Phe His Gln Gly Cys
            260                 265                 270
Thr Ile Ala Ser Gln Arg Leu Thr Pro Leu Ala Arg Gly Asp Thr Leu
        275                 280                 285
Cys Thr Asn Leu Thr Gly Thr Leu Leu Pro Ser Arg Asn Thr Asp Glu
    290                 295                 300
Thr Phe Phe Gly Val Gln Trp Val Arg Pro Gly Ser Gly Ser Gly Asn
305                 310                 315                 320
Gly Ser Glu Ser Leu Gly Trp Asp Val Ala Glu Leu Gln Leu Asn His
                325                 330                 335
Thr Gly Pro Gln Gln Asp Pro Arg Leu Tyr Trp Gln Gly Gly Pro Ala
            340                 345                 350
Leu Gly Arg Ser Phe Leu His Gly Pro Glu Leu Asp Lys Gly Gln Leu
        355                 360                 365
Arg Ile His Arg Asp Gly Ile Tyr Met Val His Ile Gln Val Thr Leu
    370                 375                 380
Ala Ile Cys Ser Ser Thr Thr Ala Ser Arg His His Pro Thr Thr Leu
385                 390                 395                 400
Ala Val Gly Ile Cys Ser Pro Ala Ser Arg Ser Ile Ser Leu Leu Arg
                405                 410                 415
Leu Ser Phe His Gln Gly Cys Thr Ile Ala Ser Gln Arg Leu Thr Pro
            420                 425                 430
Leu Ala Arg Gly Asp Thr Leu Cys Thr Asn Leu Thr Gly Thr Leu Leu
        435                 440                 445
Pro Ser Arg Asn Thr Asp Glu Thr Phe Phe Gly Val Gln Trp Val Arg
    450                 455                 460
Pro Gly Ser Ser Ser Ser Ser Ser Gly Ser Cys Asp Lys Thr
465                 470                 475                 480
His Thr Cys Pro Pro Cys Pro Ala Pro Glu Leu Leu Gly Gly Pro Ser
                485                 490                 495
Val Phe Leu Phe Pro Pro Lys Pro Lys Asp Thr Leu Met Ile Ser Arg
            500                 505                 510
Thr Pro Glu Val Thr Cys Val Val Val Asp Val Ser His Glu Asp Pro
        515                 520                 525
```

-continued

```
Glu Val Lys Phe Asn Trp Tyr Val Asp Gly Val Glu Val His Asn Ala
            530                 535                 540
Lys Thr Lys Pro Arg Glu Glu Gln Tyr Ser Ser Thr Tyr Arg Val Val
545                 550                 555                 560
Ser Val Leu Thr Val Leu His Gln Asp Trp Leu Asn Gly Lys Glu Tyr
                565                 570                 575
Lys Cys Lys Val Ser Asn Lys Ala Leu Pro Ala Pro Ile Glu Lys Thr
            580                 585                 590
Ile Ser Lys Ala Lys Gly Gln Pro Arg Glu Pro Gln Val Tyr Thr Leu
        595                 600                 605
Pro Pro Ser Arg Glu Glu Met Thr Lys Asn Gln Val Ser Leu Thr Cys
610                 615                 620
Leu Val Lys Gly Phe Tyr Pro Ser Asp Ile Ala Val Glu Trp Glu Ser
625                 630                 635                 640
Asn Gly Gln Pro Glu Asn Asn Tyr Lys Thr Thr Pro Pro Val Leu Asp
                645                 650                 655
Ser Asp Gly Ser Phe Phe Leu Tyr Ser Lys Leu Thr Val Asp Lys Ser
            660                 665                 670
Arg Trp Gln Gln Gly Asn Val Phe Ser Cys Ser Val Met His Glu Ala
        675                 680                 685
Leu His Asn His Tyr Thr Gln Lys Ser Leu Ser Leu Ser Pro Gly Ser
    690                 695                 700
Ser Ser Ser Ser Ser Ala Trp Ser His Pro Gln Phe Glu Lys
705                 710                 715

<210> SEQ ID NO 16
<211> LENGTH: 21
<212> TYPE: PRT
<213> ORGANISM: Artificial Sequence
<220> FEATURE:
<223> OTHER INFORMATION: hinge linker

<400> SEQUENCE: 16

Gly Ser Ser Ser Ser Ser Ser Ser Gly Ser Cys Asp Lys Thr His
1               5                   10                  15
Thr Cys Pro Pro Cys
            20

<210> SEQ ID NO 17
<211> LENGTH: 20
<212> TYPE: PRT
<213> ORGANISM: Artificial Sequence
<220> FEATURE:
<223> OTHER INFORMATION: universal signal peptide

<400> SEQUENCE: 17

Met Glu Thr Asp Thr Leu Leu Val Phe Val Leu Leu Val Trp Val Pro
1               5                   10                  15
Ala Gly Asn Gly
            20

<210> SEQ ID NO 18
<211> LENGTH: 15
<212> TYPE: PRT
<213> ORGANISM: Artificial Sequence
<220> FEATURE:
<223> OTHER INFORMATION: serine linker with strep tag

<400> SEQUENCE: 18
```

```
Ser Ser Ser Ser Ser Ser Ala Trp Ser His Pro Gln Phe Glu Lys
1               5                   10                  15
```

<210> SEQ ID NO 19
<211> LENGTH: 20
<212> TYPE: PRT
<213> ORGANISM: Artificial Sequence
<220> FEATURE:
<223> OTHER INFORMATION: hinge linker

<400> SEQUENCE: 19

```
Gly Ser Ser Ser Ser Ser Ser Gly Ser Cys Asp Lys Thr His Thr
1               5                   10                  15

Cys Pro Pro Cys
            20
```

<210> SEQ ID NO 20
<211> LENGTH: 19
<212> TYPE: PRT
<213> ORGANISM: Artificial Sequence
<220> FEATURE:
<223> OTHER INFORMATION: hinge linker

<400> SEQUENCE: 20

```
Gly Ser Ser Ser Ser Ser Gly Ser Cys Asp Lys Thr His Thr Cys
1               5                   10                  15

Pro Pro Cys
```

<210> SEQ ID NO 21
<211> LENGTH: 18
<212> TYPE: PRT
<213> ORGANISM: Artificial Sequence
<220> FEATURE:
<223> OTHER INFORMATION: hinge linker

<400> SEQUENCE: 21

```
Gly Ser Ser Ser Ser Gly Ser Cys Asp Lys Thr His Thr Cys Pro
1               5                   10                  15

Pro Cys
```

<210> SEQ ID NO 22
<211> LENGTH: 16
<212> TYPE: PRT
<213> ORGANISM: Artificial Sequence
<220> FEATURE:
<223> OTHER INFORMATION: hinge linker

<400> SEQUENCE: 22

```
Gly Ser Ser Ser Gly Ser Cys Asp Lys Thr His Thr Cys Pro Pro Cys
1               5                   10                  15
```

<210> SEQ ID NO 23
<211> LENGTH: 18
<212> TYPE: PRT
<213> ORGANISM: Artificial Sequence
<220> FEATURE:
<223> OTHER INFORMATION: hinge linker

<400> SEQUENCE: 23

```
Gly Ser Ser Ser Gly Ser Cys Asp Lys Thr His Thr Cys Pro Pro Cys
1               5                   10                  15

Gly Ser
```

<210> SEQ ID NO 24

```
<211> LENGTH: 20
<212> TYPE: PRT
<213> ORGANISM: Artificial Sequence
<220> FEATURE:
<223> OTHER INFORMATION: hinge linker

<400> SEQUENCE: 24

Gly Ser Ser Ser Gly Ser Cys Asp Lys Thr His Thr Cys Pro Pro Cys
1               5                   10                  15

Gly Ser Gly Ser
            20

<210> SEQ ID NO 25
<211> LENGTH: 704
<212> TYPE: PRT
<213> ORGANISM: Artificial Sequence
<220> FEATURE:
<223> OTHER INFORMATION: PROTEIN A - no strep tag

<400> SEQUENCE: 25

Met Glu Thr Asp Thr Leu Leu Val Phe Val Leu Leu Val Trp Val Pro
1               5                   10                  15

Ala Gly Asn Gly Glu Ser Leu Gly Trp Asp Val Ala Glu Leu Gln Leu
            20                  25                  30

Asn His Thr Gly Pro Gln Gln Asp Pro Arg Leu Tyr Trp Gln Gly Gly
        35                  40                  45

Pro Ala Leu Gly Arg Ser Phe Leu His Gly Pro Glu Leu Asp Lys Gly
    50                  55                  60

Gln Leu Arg Ile His Arg Asp Gly Ile Tyr Met Val His Ile Gln Val
65                  70                  75                  80

Thr Leu Ala Ile Cys Ser Ser Thr Thr Ala Ser Arg His His Pro Thr
                85                  90                  95

Thr Leu Ala Val Gly Ile Cys Ser Pro Ala Ser Arg Ser Ile Ser Leu
            100                 105                 110

Leu Arg Leu Ser Phe His Gln Gly Cys Thr Ile Ala Ser Gln Arg Leu
        115                 120                 125

Thr Pro Leu Ala Arg Gly Asp Thr Leu Cys Thr Asn Leu Thr Gly Thr
    130                 135                 140

Leu Leu Pro Ser Arg Asn Thr Asp Glu Thr Phe Phe Gly Val Gln Trp
145                 150                 155                 160

Val Arg Pro Gly Ser Gly Ser Gly Asn Gly Ser Glu Ser Leu Gly Trp
                165                 170                 175

Asp Val Ala Glu Leu Gln Leu Asn His Thr Gly Pro Gln Gln Asp Pro
            180                 185                 190

Arg Leu Tyr Trp Gln Gly Gly Pro Ala Leu Gly Arg Ser Phe Leu His
        195                 200                 205

Gly Pro Glu Leu Asp Lys Gly Gln Leu Arg Ile His Arg Asp Gly Ile
    210                 215                 220

Tyr Met Val His Ile Gln Val Thr Leu Ala Ile Cys Ser Ser Thr Thr
225                 230                 235                 240

Ala Ser Arg His His Pro Thr Thr Leu Ala Val Gly Ile Cys Ser Pro
                245                 250                 255

Ala Ser Arg Ser Ile Ser Leu Leu Arg Leu Ser Phe His Gln Gly Cys
            260                 265                 270

Thr Ile Ala Ser Gln Arg Leu Thr Pro Leu Ala Arg Gly Asp Thr Leu
        275                 280                 285

Cys Thr Asn Leu Thr Gly Thr Leu Leu Pro Ser Arg Asn Thr Asp Glu
```

```
            290                 295                 300

Thr Phe Phe Gly Val Gln Trp Val Arg Pro Gly Ser Gly Ser Gly Asn
305                 310                 315                 320

Gly Ser Glu Ser Leu Gly Trp Asp Val Ala Glu Leu Gln Leu Asn His
                325                 330                 335

Thr Gly Pro Gln Gln Asp Pro Arg Leu Tyr Trp Gln Gly Gly Pro Ala
            340                 345                 350

Leu Gly Arg Ser Phe Leu His Gly Pro Glu Leu Asp Lys Gly Gln Leu
        355                 360                 365

Arg Ile His Arg Asp Gly Ile Tyr Met Val His Ile Gln Val Thr Leu
370                 375                 380

Ala Ile Cys Ser Ser Thr Thr Ala Ser Arg His His Pro Thr Thr Leu
385                 390                 395                 400

Ala Val Gly Ile Cys Ser Pro Ala Ser Arg Ser Ile Ser Leu Leu Arg
                405                 410                 415

Leu Ser Phe His Gln Gly Cys Thr Ile Ala Ser Gln Arg Leu Thr Pro
            420                 425                 430

Leu Ala Arg Gly Asp Thr Leu Cys Thr Asn Leu Thr Gly Thr Leu Leu
        435                 440                 445

Pro Ser Arg Asn Thr Asp Glu Thr Phe Phe Gly Val Gln Trp Val Arg
    450                 455                 460

Pro Gly Ser Ser Ser Ser Ser Ser Gly Ser Cys Asp Lys Thr
465                 470                 475                 480

His Thr Cys Pro Pro Cys Pro Ala Pro Glu Leu Leu Gly Gly Pro Ser
                485                 490                 495

Val Phe Leu Phe Pro Pro Lys Pro Lys Asp Thr Leu Met Ile Ser Arg
            500                 505                 510

Thr Pro Glu Val Thr Cys Val Val Val Asp Val Ser His Glu Asp Pro
        515                 520                 525

Glu Val Lys Phe Asn Trp Tyr Val Asp Gly Val Glu Val His Asn Ala
    530                 535                 540

Lys Thr Lys Pro Arg Glu Glu Gln Tyr Ser Ser Thr Tyr Arg Val Val
545                 550                 555                 560

Ser Val Leu Thr Val Leu His Gln Asp Trp Leu Asn Gly Lys Glu Tyr
                565                 570                 575

Lys Cys Lys Val Ser Asn Lys Ala Leu Pro Ala Pro Ile Glu Lys Thr
            580                 585                 590

Ile Ser Lys Ala Lys Gly Gln Pro Arg Glu Pro Gln Val Tyr Thr Leu
        595                 600                 605

Pro Pro Ser Arg Glu Glu Met Thr Lys Asn Gln Val Ser Leu Thr Cys
    610                 615                 620

Leu Val Lys Gly Phe Tyr Pro Ser Asp Ile Ala Val Glu Trp Glu Ser
625                 630                 635                 640

Asn Gly Gln Pro Glu Asn Asn Tyr Lys Thr Thr Pro Pro Val Leu Asp
                645                 650                 655

Ser Asp Gly Ser Phe Phe Leu Tyr Ser Lys Leu Thr Val Asp Lys Ser
            660                 665                 670

Arg Trp Gln Gln Gly Asn Val Phe Ser Cys Ser Val Met His Glu Ala
        675                 680                 685

Leu His Asn His Tyr Thr Gln Lys Ser Leu Ser Leu Ser Pro Gly Lys
    690                 695                 700

<210> SEQ ID NO 26
```

<211> LENGTH: 703
<212> TYPE: PRT
<213> ORGANISM: Artificial Sequence
<220> FEATURE:
<223> OTHER INFORMATION: CD27L-wt fused to SEQ_14

<400> SEQUENCE: 26

```
Met Glu Thr Asp Thr Leu Leu Val Phe Val Leu Leu Val Trp Val Pro
1               5                   10                  15

Ala Gly Asn Gly Glu Ser Leu Gly Trp Asp Val Ala Glu Leu Gln Leu
            20                  25                  30

Asn His Thr Gly Pro Gln Gln Asp Pro Arg Leu Tyr Trp Gln Gly Gly
        35                  40                  45

Pro Ala Leu Gly Arg Ser Phe Leu His Gly Pro Glu Leu Asp Lys Gly
50                  55                  60

Gln Leu Arg Ile His Arg Asp Gly Ile Tyr Met Val His Ile Gln Val
65                  70                  75                  80

Thr Leu Ala Ile Cys Ser Ser Thr Thr Ala Ser Arg His His Pro Thr
                85                  90                  95

Thr Leu Ala Val Gly Ile Cys Ser Pro Ala Ser Arg Ser Ile Ser Leu
            100                 105                 110

Leu Arg Leu Ser Phe His Gln Gly Cys Thr Ile Ala Ser Gln Arg Leu
        115                 120                 125

Thr Pro Leu Ala Arg Gly Asp Thr Leu Cys Thr Asn Leu Thr Gly Thr
130                 135                 140

Leu Leu Pro Ser Arg Asn Thr Asp Glu Thr Phe Phe Gly Val Gln Trp
145                 150                 155                 160

Val Arg Pro Gly Ser Gly Ser Gly Asn Gly Ser Glu Ser Leu Gly Trp
                165                 170                 175

Asp Val Ala Glu Leu Gln Leu Asn His Thr Gly Pro Gln Gln Asp Pro
            180                 185                 190

Arg Leu Tyr Trp Gln Gly Gly Pro Ala Leu Gly Arg Ser Phe Leu His
        195                 200                 205

Gly Pro Glu Leu Asp Lys Gly Gln Leu Arg Ile His Arg Asp Gly Ile
210                 215                 220

Tyr Met Val His Ile Gln Val Thr Leu Ala Ile Cys Ser Ser Thr Thr
225                 230                 235                 240

Ala Ser Arg His His Pro Thr Thr Leu Ala Val Gly Ile Cys Ser Pro
                245                 250                 255

Ala Ser Arg Ser Ile Ser Leu Leu Arg Leu Ser Phe His Gln Gly Cys
            260                 265                 270

Thr Ile Ala Ser Gln Arg Leu Thr Pro Leu Ala Arg Gly Asp Thr Leu
        275                 280                 285

Cys Thr Asn Leu Thr Gly Thr Leu Leu Pro Ser Arg Asn Thr Asp Glu
290                 295                 300

Thr Phe Phe Gly Val Gln Trp Val Arg Pro Gly Ser Gly Ser Gly Asn
305                 310                 315                 320

Gly Ser Glu Ser Leu Gly Trp Asp Val Ala Glu Leu Gln Leu Asn His
                325                 330                 335

Thr Gly Pro Gln Gln Asp Pro Arg Leu Tyr Trp Gln Gly Gly Pro Ala
            340                 345                 350

Leu Gly Arg Ser Phe Leu His Gly Pro Glu Leu Asp Lys Gly Gln Leu
        355                 360                 365

Arg Ile His Arg Asp Gly Ile Tyr Met Val His Ile Gln Val Thr Leu
370                 375                 380
```

Ala Ile Cys Ser Ser Thr Thr Ala Ser Arg His His Pro Thr Thr Leu
385                 390                 395                 400

Ala Val Gly Ile Cys Ser Pro Ala Ser Arg Ser Ile Ser Leu Leu Arg
            405                 410                 415

Leu Ser Phe His Gln Gly Cys Thr Ile Ala Ser Gln Arg Leu Thr Pro
        420                 425                 430

Leu Ala Arg Gly Asp Thr Leu Cys Thr Asn Leu Thr Gly Thr Leu Leu
    435                 440                 445

Pro Ser Arg Asn Thr Asp Glu Thr Phe Phe Gly Val Gln Trp Val Arg
450                 455                 460

Pro Gly Ser Ser Ser Ser Ser Ser Gly Ser Cys Asp Lys Thr
465                 470                 475                 480

His Thr Cys Pro Pro Cys Pro Ala Pro Val Ala Gly Pro Ser Val
                485                 490                 495

Phe Leu Phe Pro Pro Lys Pro Lys Asp Thr Leu Met Ile Ser Arg Thr
                500                 505                 510

Pro Glu Val Thr Cys Val Val Val Asp Val Ser His Glu Asp Pro Glu
            515                 520                 525

Val Lys Phe Asn Trp Tyr Val Asp Gly Val Glu Val His Asn Ala Lys
        530                 535                 540

Thr Lys Pro Arg Glu Glu Gln Tyr Asn Ser Thr Tyr Arg Val Val Ser
545                 550                 555                 560

Val Leu Thr Val Leu His Gln Asp Trp Leu Asn Gly Lys Glu Tyr Lys
                565                 570                 575

Cys Lys Val Ser Asn Lys Gly Leu Pro Ser Ser Ile Glu Lys Thr Ile
                580                 585                 590

Ser Lys Ala Lys Gly Gln Pro Arg Glu Pro Gln Val Tyr Thr Leu Pro
            595                 600                 605

Pro Ser Arg Glu Glu Met Thr Lys Asn Gln Val Ser Leu Thr Cys Leu
        610                 615                 620

Val Lys Gly Phe Tyr Pro Ser Asp Ile Ala Val Glu Trp Glu Ser Asn
625                 630                 635                 640

Gly Gln Pro Glu Asn Asn Tyr Lys Thr Thr Pro Pro Val Leu Asp Ser
                645                 650                 655

Asp Gly Ser Phe Phe Leu Tyr Ser Lys Leu Thr Val Asp Lys Ser Arg
                660                 665                 670

Trp Gln Gln Gly Asn Val Phe Ser Cys Ser Val Met His Glu Ala Leu
            675                 680                 685

His Asn His Tyr Thr Gln Lys Ser Leu Ser Leu Ser Pro Gly Lys
        690                 695                 700

<210> SEQ ID NO 27
<211> LENGTH: 684
<212> TYPE: PRT
<213> ORGANISM: Artificial Sequence
<220> FEATURE:
<223> OTHER INFORMATION: CD27L-wt fused to SEQ_13 (no signal peptide, no
      strep tag)

<400> SEQUENCE: 27

Glu Ser Leu Gly Trp Asp Val Ala Glu Leu Gln Leu Asn His Thr Gly
1               5                   10                  15

Pro Gln Gln Asp Pro Arg Leu Tyr Trp Gln Gly Gly Pro Ala Leu Gly
            20                  25                  30

Arg Ser Phe Leu His Gly Pro Glu Leu Asp Lys Gly Gln Leu Arg Ile

```
                 35                  40                  45
His Arg Asp Gly Ile Tyr Met Val His Ile Gln Val Thr Leu Ala Ile
 50                  55                  60
Cys Ser Ser Thr Thr Ala Ser Arg His His Pro Thr Thr Leu Ala Val
 65                  70                  75                  80
Gly Ile Cys Ser Pro Ala Ser Arg Ser Ile Ser Leu Leu Arg Leu Ser
                     85                  90                  95
Phe His Gln Gly Cys Thr Ile Ala Ser Gln Arg Leu Thr Pro Leu Ala
                100                 105                 110
Arg Gly Asp Thr Leu Cys Thr Asn Leu Thr Gly Thr Leu Leu Pro Ser
                115                 120                 125
Arg Asn Thr Asp Glu Thr Phe Phe Gly Val Gln Trp Val Arg Pro Gly
130                 135                 140
Ser Gly Ser Gly Asn Gly Ser Glu Ser Leu Gly Trp Asp Val Ala Glu
145                 150                 155                 160
Leu Gln Leu Asn His Thr Gly Pro Gln Gln Asp Pro Arg Leu Tyr Trp
                165                 170                 175
Gln Gly Gly Pro Ala Leu Gly Arg Ser Phe Leu His Gly Pro Glu Leu
                180                 185                 190
Asp Lys Gly Gln Leu Arg Ile His Arg Asp Gly Ile Tyr Met Val His
                195                 200                 205
Ile Gln Val Thr Leu Ala Ile Cys Ser Ser Thr Thr Ala Ser Arg His
210                 215                 220
His Pro Thr Thr Leu Ala Val Gly Ile Cys Ser Pro Ala Ser Arg Ser
225                 230                 235                 240
Ile Ser Leu Leu Arg Leu Ser Phe His Gln Gly Cys Thr Ile Ala Ser
                245                 250                 255
Gln Arg Leu Thr Pro Leu Ala Arg Gly Asp Thr Leu Cys Thr Asn Leu
                260                 265                 270
Thr Gly Thr Leu Leu Pro Ser Arg Asn Thr Asp Glu Thr Phe Phe Gly
                275                 280                 285
Val Gln Trp Val Arg Pro Gly Ser Gly Ser Gly Asn Gly Ser Glu Ser
                290                 295                 300
Leu Gly Trp Asp Val Ala Glu Leu Gln Leu Asn His Thr Gly Pro Gln
305                 310                 315                 320
Gln Asp Pro Arg Leu Tyr Trp Gln Gly Gly Pro Ala Leu Gly Arg Ser
                325                 330                 335
Phe Leu His Gly Pro Glu Leu Asp Lys Gly Gln Leu Arg Ile His Arg
                340                 345                 350
Asp Gly Ile Tyr Met Val His Ile Gln Val Thr Leu Ala Ile Cys Ser
                355                 360                 365
Ser Thr Thr Ala Ser Arg His His Pro Thr Thr Leu Ala Val Gly Ile
                370                 375                 380
Cys Ser Pro Ala Ser Arg Ser Ile Ser Leu Leu Arg Leu Ser Phe His
385                 390                 395                 400
Gln Gly Cys Thr Ile Ala Ser Gln Arg Leu Thr Pro Leu Ala Arg Gly
                405                 410                 415
Asp Thr Leu Cys Thr Asn Leu Thr Gly Thr Leu Leu Pro Ser Arg Asn
                420                 425                 430
Thr Asp Glu Thr Phe Phe Gly Val Gln Trp Val Arg Pro Gly Ser Ser
                435                 440                 445
Ser Ser Ser Ser Ser Gly Ser Cys Asp Lys Thr His Thr Cys Pro
450                 455                 460
```

Pro Cys Pro Ala Pro Glu Leu Leu Gly Gly Pro Ser Val Phe Leu Phe
465                 470                 475                 480

Pro Pro Lys Pro Lys Asp Thr Leu Met Ile Ser Arg Thr Pro Glu Val
            485                 490                 495

Thr Cys Val Val Val Asp Val Ser His Glu Asp Pro Glu Val Lys Phe
                500                 505                 510

Asn Trp Tyr Val Asp Gly Val Glu Val His Asn Ala Lys Thr Lys Pro
            515                 520                 525

Arg Glu Glu Gln Tyr Ser Ser Thr Tyr Arg Val Val Ser Val Leu Thr
            530                 535                 540

Val Leu His Gln Asp Trp Leu Asn Gly Lys Glu Tyr Lys Cys Lys Val
545                 550                 555                 560

Ser Asn Lys Ala Leu Pro Ala Pro Ile Glu Lys Thr Ile Ser Lys Ala
                565                 570                 575

Lys Gly Gln Pro Arg Glu Pro Gln Val Tyr Thr Leu Pro Pro Ser Arg
            580                 585                 590

Glu Glu Met Thr Lys Asn Gln Val Ser Leu Thr Cys Leu Val Lys Gly
            595                 600                 605

Phe Tyr Pro Ser Asp Ile Ala Val Glu Trp Glu Ser Asn Gly Gln Pro
610                 615                 620

Glu Asn Asn Tyr Lys Thr Thr Pro Pro Val Leu Asp Ser Asp Gly Ser
625                 630                 635                 640

Phe Phe Leu Tyr Ser Lys Leu Thr Val Asp Lys Ser Arg Trp Gln Gln
                645                 650                 655

Gly Asn Val Phe Ser Cys Ser Val Met His Glu Ala Leu His Asn His
            660                 665                 670

Tyr Thr Gln Lys Ser Leu Ser Leu Ser Pro Gly Lys
            675                 680

<210> SEQ ID NO 28
<211> LENGTH: 698
<212> TYPE: PRT
<213> ORGANISM: Artificial Sequence
<220> FEATURE:
<223> OTHER INFORMATION: CD27L-wt fused to SEQ_13 (incl. strep tag)

<400> SEQUENCE: 28

Glu Ser Leu Gly Trp Asp Val Ala Glu Leu Gln Leu Asn His Thr Gly
1               5                   10                  15

Pro Gln Gln Asp Pro Arg Leu Tyr Trp Gln Gly Gly Pro Ala Leu Gly
            20                  25                  30

Arg Ser Phe Leu His Gly Pro Glu Leu Asp Lys Gly Gln Leu Arg Ile
        35                  40                  45

His Arg Asp Gly Ile Tyr Met Val His Ile Gln Val Thr Leu Ala Ile
    50                  55                  60

Cys Ser Ser Thr Thr Ala Ser Arg His His Pro Thr Thr Leu Ala Val
65                  70                  75                  80

Gly Ile Cys Ser Pro Ala Ser Arg Ser Ile Ser Leu Leu Arg Leu Ser
                85                  90                  95

Phe His Gln Gly Cys Thr Ile Ala Ser Gln Arg Leu Thr Pro Leu Ala
            100                 105                 110

Arg Gly Asp Thr Leu Cys Thr Asn Leu Thr Gly Thr Leu Leu Pro Ser
            115                 120                 125

Arg Asn Thr Asp Glu Thr Phe Phe Gly Val Gln Trp Val Arg Pro Gly
        130                 135                 140

```
Ser Gly Ser Gly Asn Gly Ser Glu Ser Leu Gly Trp Asp Val Ala Glu
145                 150                 155                 160

Leu Gln Leu Asn His Thr Gly Pro Gln Gln Asp Pro Arg Leu Tyr Trp
                165                 170                 175

Gln Gly Gly Pro Ala Leu Gly Arg Ser Phe Leu His Gly Pro Glu Leu
            180                 185                 190

Asp Lys Gly Gln Leu Arg Ile His Arg Asp Gly Ile Tyr Met Val His
            195                 200                 205

Ile Gln Val Thr Leu Ala Ile Cys Ser Ser Thr Thr Ala Ser Arg His
210                 215                 220

His Pro Thr Thr Leu Ala Val Gly Ile Cys Ser Pro Ala Ser Arg Ser
225                 230                 235                 240

Ile Ser Leu Leu Arg Leu Ser Phe His Gln Gly Cys Thr Ile Ala Ser
                245                 250                 255

Gln Arg Leu Thr Pro Leu Ala Arg Gly Asp Thr Leu Cys Thr Asn Leu
            260                 265                 270

Thr Gly Thr Leu Leu Pro Ser Arg Asn Thr Asp Glu Thr Phe Phe Gly
        275                 280                 285

Val Gln Trp Val Arg Pro Gly Ser Gly Ser Gly Asn Gly Ser Glu Ser
290                 295                 300

Leu Gly Trp Asp Val Ala Glu Leu Gln Leu Asn His Thr Gly Pro Gln
305                 310                 315                 320

Gln Asp Pro Arg Leu Tyr Trp Gln Gly Gly Pro Ala Leu Gly Arg Ser
                325                 330                 335

Phe Leu His Gly Pro Glu Leu Asp Lys Gly Gln Leu Arg Ile His Arg
            340                 345                 350

Asp Gly Ile Tyr Met Val His Ile Gln Val Thr Leu Ala Ile Cys Ser
            355                 360                 365

Ser Thr Thr Ala Ser Arg His His Pro Thr Thr Leu Ala Val Gly Ile
        370                 375                 380

Cys Ser Pro Ala Ser Arg Ser Ile Ser Leu Leu Arg Leu Ser Phe His
385                 390                 395                 400

Gln Gly Cys Thr Ile Ala Ser Gln Arg Leu Thr Pro Leu Ala Arg Gly
                405                 410                 415

Asp Thr Leu Cys Thr Asn Leu Thr Gly Thr Leu Leu Pro Ser Arg Asn
            420                 425                 430

Thr Asp Glu Thr Phe Phe Gly Val Gln Trp Val Arg Pro Gly Ser Ser
            435                 440                 445

Ser Ser Ser Ser Ser Gly Ser Cys Asp Lys Thr His Thr Cys Pro
450                 455                 460

Pro Cys Pro Ala Pro Glu Leu Leu Gly Gly Pro Ser Val Phe Leu Phe
465                 470                 475                 480

Pro Pro Lys Pro Lys Asp Thr Leu Met Ile Ser Arg Thr Pro Glu Val
                485                 490                 495

Thr Cys Val Val Val Asp Val Ser His Glu Asp Pro Glu Val Lys Phe
            500                 505                 510

Asn Trp Tyr Val Asp Gly Val Glu Val His Asn Ala Lys Thr Lys Pro
            515                 520                 525

Arg Glu Glu Gln Tyr Ser Ser Thr Tyr Arg Val Val Ser Val Leu Thr
        530                 535                 540

Val Leu His Gln Asp Trp Leu Asn Gly Lys Glu Tyr Lys Cys Lys Val
545                 550                 555                 560
```

```
Ser Asn Lys Ala Leu Pro Ala Pro Ile Glu Lys Thr Ile Ser Lys Ala
            565                 570                 575

Lys Gly Gln Pro Arg Glu Pro Gln Val Tyr Thr Leu Pro Pro Ser Arg
        580                 585                 590

Glu Glu Met Thr Lys Asn Gln Val Ser Leu Thr Cys Leu Val Lys Gly
    595                 600                 605

Phe Tyr Pro Ser Asp Ile Ala Val Glu Trp Glu Ser Asn Gly Gln Pro
610                 615                 620

Glu Asn Asn Tyr Lys Thr Thr Pro Pro Val Leu Asp Ser Asp Gly Ser
625                 630                 635                 640

Phe Phe Leu Tyr Ser Lys Leu Thr Val Asp Lys Ser Arg Trp Gln Gln
                645                 650                 655

Gly Asn Val Phe Ser Cys Ser Val Met His Glu Ala Leu His Asn His
            660                 665                 670

Tyr Thr Gln Lys Ser Leu Ser Leu Ser Pro Gly Ser Ser Ser Ser Ser
        675                 680                 685

Ser Ala Trp Ser His Pro Gln Phe Glu Lys
    690                 695
```

<210> SEQ ID NO 29
<211> LENGTH: 683
<212> TYPE: PRT
<213> ORGANISM: Artificial Sequence
<220> FEATURE:
<223> OTHER INFORMATION: CD27L-wt fused to SEQ_14 (no signal peptide, no
      strep tag)

<400> SEQUENCE: 29

```
Glu Ser Leu Gly Trp Asp Val Ala Glu Leu Gln Leu Asn His Thr Gly
1               5                   10                  15

Pro Gln Gln Asp Pro Arg Leu Tyr Trp Gln Gly Gly Pro Ala Leu Gly
            20                  25                  30

Arg Ser Phe Leu His Gly Pro Glu Leu Asp Lys Gly Gln Leu Arg Ile
        35                  40                  45

His Arg Asp Gly Ile Tyr Met Val His Ile Gln Val Thr Leu Ala Ile
    50                  55                  60

Cys Ser Ser Thr Thr Ala Ser Arg His His Pro Thr Thr Leu Ala Val
65                  70                  75                  80

Gly Ile Cys Ser Pro Ala Ser Arg Ser Ile Ser Leu Leu Arg Leu Ser
                85                  90                  95

Phe His Gln Gly Cys Thr Ile Ala Ser Gln Arg Leu Thr Pro Leu Ala
            100                 105                 110

Arg Gly Asp Thr Leu Cys Thr Asn Leu Thr Gly Thr Leu Leu Pro Ser
        115                 120                 125

Arg Asn Thr Asp Glu Thr Phe Phe Gly Val Gln Trp Val Arg Pro Gly
    130                 135                 140

Ser Gly Ser Gly Asn Gly Ser Glu Ser Leu Gly Trp Asp Val Ala Glu
145                 150                 155                 160

Leu Gln Leu Asn His Thr Gly Pro Gln Gln Asp Pro Arg Leu Tyr Trp
                165                 170                 175

Gln Gly Gly Pro Ala Leu Gly Arg Ser Phe Leu His Gly Pro Glu Leu
            180                 185                 190

Asp Lys Gly Gln Leu Arg Ile His Arg Asp Gly Ile Tyr Met Val His
        195                 200                 205

Ile Gln Val Thr Leu Ala Ile Cys Ser Ser Thr Thr Ala Ser Arg His
    210                 215                 220
```

-continued

His Pro Thr Thr Leu Ala Val Gly Ile Cys Ser Pro Ala Ser Arg Ser
225                 230                 235                 240

Ile Ser Leu Leu Arg Leu Ser Phe His Gln Gly Cys Thr Ile Ala Ser
                245                 250                 255

Gln Arg Leu Thr Pro Leu Ala Arg Gly Asp Thr Leu Cys Thr Asn Leu
            260                 265                 270

Thr Gly Thr Leu Leu Pro Ser Arg Asn Thr Asp Glu Thr Phe Phe Gly
        275                 280                 285

Val Gln Trp Val Arg Pro Gly Ser Gly Ser Gly Asn Gly Ser Glu Ser
    290                 295                 300

Leu Gly Trp Asp Val Ala Glu Leu Gln Leu Asn His Thr Gly Pro Gln
305                 310                 315                 320

Gln Asp Pro Arg Leu Tyr Trp Gln Gly Gly Pro Ala Leu Gly Arg Ser
                325                 330                 335

Phe Leu His Gly Pro Glu Leu Asp Lys Gly Gln Leu Arg Ile His Arg
            340                 345                 350

Asp Gly Ile Tyr Met Val His Ile Gln Val Thr Leu Ala Ile Cys Ser
        355                 360                 365

Ser Thr Thr Ala Ser Arg His His Pro Thr Thr Leu Ala Val Gly Ile
    370                 375                 380

Cys Ser Pro Ala Ser Arg Ser Ile Ser Leu Leu Arg Leu Ser Phe His
385                 390                 395                 400

Gln Gly Cys Thr Ile Ala Ser Gln Arg Leu Thr Pro Leu Ala Arg Gly
                405                 410                 415

Asp Thr Leu Cys Thr Asn Leu Thr Gly Thr Leu Leu Pro Ser Arg Asn
            420                 425                 430

Thr Asp Glu Thr Phe Phe Gly Val Gln Trp Val Arg Pro Gly Ser Ser
        435                 440                 445

Ser Ser Ser Ser Ser Gly Ser Cys Asp Lys Thr His Thr Cys Pro
    450                 455                 460

Pro Cys Pro Ala Pro Pro Val Ala Gly Pro Ser Val Phe Leu Phe Pro
465                 470                 475                 480

Pro Lys Pro Lys Asp Thr Leu Met Ile Ser Arg Thr Pro Glu Val Thr
                485                 490                 495

Cys Val Val Val Asp Val Ser His Glu Asp Pro Glu Val Lys Phe Asn
            500                 505                 510

Trp Tyr Val Asp Gly Val Glu Val His Asn Ala Lys Thr Lys Pro Arg
        515                 520                 525

Glu Glu Gln Tyr Asn Ser Thr Tyr Arg Val Val Ser Val Leu Thr Val
    530                 535                 540

Leu His Gln Asp Trp Leu Asn Gly Lys Glu Tyr Lys Cys Lys Val Ser
545                 550                 555                 560

Asn Lys Gly Leu Pro Ser Ser Ile Glu Lys Thr Ile Ser Lys Ala Lys
                565                 570                 575

Gly Gln Pro Arg Glu Pro Gln Val Tyr Thr Leu Pro Pro Ser Arg Glu
            580                 585                 590

Glu Met Thr Lys Asn Gln Val Ser Leu Thr Cys Leu Val Lys Gly Phe
        595                 600                 605

Tyr Pro Ser Asp Ile Ala Val Glu Trp Glu Ser Asn Gly Gln Pro Glu
    610                 615                 620

Asn Asn Tyr Lys Thr Thr Pro Pro Val Leu Asp Ser Asp Gly Ser Phe
625                 630                 635                 640

Phe Leu Tyr Ser Lys Leu Thr Val Asp Lys Ser Arg Trp Gln Gln Gly
                 645                 650                 655

Asn Val Phe Ser Cys Ser Val Met His Glu Ala Leu His Asn His Tyr
            660                 665                 670

Thr Gln Lys Ser Leu Ser Leu Ser Pro Gly Lys
        675                 680

<210> SEQ ID NO 30
<211> LENGTH: 684
<212> TYPE: PRT
<213> ORGANISM: Artificial Sequence
<220> FEATURE:
<223> OTHER INFORMATION: SEQ_27 with AA exchange (E51Q of SEQ_1)

<400> SEQUENCE: 30

Gln Ser Leu Gly Trp Asp Val Ala Glu Leu Gln Leu Asn His Thr Gly
1               5                   10                  15

Pro Gln Gln Asp Pro Arg Leu Tyr Trp Gln Gly Gly Pro Ala Leu Gly
            20                  25                  30

Arg Ser Phe Leu His Gly Pro Glu Leu Asp Lys Gly Gln Leu Arg Ile
        35                  40                  45

His Arg Asp Gly Ile Tyr Met Val His Ile Gln Val Thr Leu Ala Ile
    50                  55                  60

Cys Ser Ser Thr Thr Ala Ser Arg His Pro Thr Thr Leu Ala Val
65                  70                  75                  80

Gly Ile Cys Ser Pro Ala Ser Arg Ser Ile Ser Leu Leu Arg Leu Ser
                85                  90                  95

Phe His Gln Gly Cys Thr Ile Ala Ser Gln Arg Leu Thr Pro Leu Ala
            100                 105                 110

Arg Gly Asp Thr Leu Cys Thr Asn Leu Thr Gly Thr Leu Leu Pro Ser
        115                 120                 125

Arg Asn Thr Asp Glu Thr Phe Phe Gly Val Gln Trp Val Arg Pro Gly
    130                 135                 140

Ser Gly Ser Gly Asn Gly Ser Glu Ser Leu Gly Trp Asp Val Ala Glu
145                 150                 155                 160

Leu Gln Leu Asn His Thr Gly Pro Gln Gln Asp Pro Arg Leu Tyr Trp
                165                 170                 175

Gln Gly Gly Pro Ala Leu Gly Arg Ser Phe Leu His Gly Pro Glu Leu
            180                 185                 190

Asp Lys Gly Gln Leu Arg Ile His Arg Asp Gly Ile Tyr Met Val His
        195                 200                 205

Ile Gln Val Thr Leu Ala Ile Cys Ser Ser Thr Thr Ala Ser Arg His
    210                 215                 220

His Pro Thr Thr Leu Ala Val Gly Ile Cys Ser Pro Ala Ser Arg Ser
225                 230                 235                 240

Ile Ser Leu Leu Arg Leu Ser Phe His Gln Gly Cys Thr Ile Ala Ser
                245                 250                 255

Gln Arg Leu Thr Pro Leu Ala Arg Gly Asp Thr Leu Cys Thr Asn Leu
            260                 265                 270

Thr Gly Thr Leu Leu Pro Ser Arg Asn Thr Asp Glu Thr Phe Phe Gly
        275                 280                 285

Val Gln Trp Val Arg Pro Gly Ser Gly Ser Gly Asn Gly Ser Glu Ser
    290                 295                 300

Leu Gly Trp Asp Val Ala Glu Leu Gln Leu Asn His Thr Gly Pro Gln
305                 310                 315                 320

Gln Asp Pro Arg Leu Tyr Trp Gln Gly Gly Pro Ala Leu Gly Arg Ser
              325                 330                 335

Phe Leu His Gly Pro Glu Leu Asp Lys Gly Gln Leu Arg Ile His Arg
          340                 345                 350

Asp Gly Ile Tyr Met Val His Ile Gln Val Thr Leu Ala Ile Cys Ser
          355                 360                 365

Ser Thr Thr Ala Ser Arg His His Pro Thr Thr Leu Ala Val Gly Ile
      370                 375                 380

Cys Ser Pro Ala Ser Arg Ser Ile Ser Leu Leu Arg Leu Ser Phe His
385                 390                 395                 400

Gln Gly Cys Thr Ile Ala Ser Gln Arg Leu Thr Pro Leu Ala Arg Gly
                  405                 410                 415

Asp Thr Leu Cys Thr Asn Leu Thr Gly Thr Leu Leu Pro Ser Arg Asn
              420                 425                 430

Thr Asp Glu Thr Phe Phe Gly Val Gln Trp Val Arg Pro Gly Ser Ser
          435                 440                 445

Ser Ser Ser Ser Ser Gly Ser Cys Asp Lys Thr His Thr Cys Pro
      450                 455                 460

Pro Cys Pro Ala Pro Glu Leu Leu Gly Gly Pro Ser Val Phe Leu Phe
465                 470                 475                 480

Pro Pro Lys Pro Lys Asp Thr Leu Met Ile Ser Arg Thr Pro Glu Val
                  485                 490                 495

Thr Cys Val Val Val Asp Val Ser His Glu Asp Pro Glu Val Lys Phe
              500                 505                 510

Asn Trp Tyr Val Asp Gly Val Glu Val His Asn Ala Lys Thr Lys Pro
          515                 520                 525

Arg Glu Glu Gln Tyr Ser Ser Thr Tyr Arg Val Val Ser Val Leu Thr
530                 535                 540

Val Leu His Gln Asp Trp Leu Asn Gly Lys Glu Tyr Lys Cys Lys Val
545                 550                 555                 560

Ser Asn Lys Ala Leu Pro Ala Pro Ile Glu Lys Thr Ile Ser Lys Ala
                  565                 570                 575

Lys Gly Gln Pro Arg Glu Pro Gln Val Tyr Thr Leu Pro Pro Ser Arg
              580                 585                 590

Glu Glu Met Thr Lys Asn Gln Val Ser Leu Thr Cys Leu Val Lys Gly
          595                 600                 605

Phe Tyr Pro Ser Asp Ile Ala Val Glu Trp Glu Ser Asn Gly Gln Pro
      610                 615                 620

Glu Asn Asn Tyr Lys Thr Thr Pro Pro Val Leu Asp Ser Asp Gly Ser
625                 630                 635                 640

Phe Phe Leu Tyr Ser Lys Leu Thr Val Asp Lys Ser Arg Trp Gln Gln
                  645                 650                 655

Gly Asn Val Phe Ser Cys Ser Val Met His Glu Ala Leu His Asn His
              660                 665                 670

Tyr Thr Gln Lys Ser Leu Ser Leu Ser Pro Gly Lys
          675                 680

<210> SEQ ID NO 31
<211> LENGTH: 680
<212> TYPE: PRT
<213> ORGANISM: Artificial Sequence
<220> FEATURE:
<223> OTHER INFORMATION: Seq_30 with altered linker sequences

<400> SEQUENCE: 31

```
Gln Ser Leu Gly Trp Asp Val Ala Glu Leu Gln Leu Asn His Thr Gly
1               5                   10                  15

Pro Gln Gln Asp Pro Arg Leu Tyr Trp Gln Gly Gly Pro Ala Leu Gly
            20                  25                  30

Arg Ser Phe Leu His Gly Pro Glu Leu Asp Lys Gly Gln Leu Arg Ile
        35                  40                  45

His Arg Asp Gly Ile Tyr Met Val His Ile Gln Val Thr Leu Ala Ile
    50                  55                  60

Cys Ser Ser Thr Thr Ala Ser Arg His His Pro Thr Thr Leu Ala Val
65                  70                  75                  80

Gly Ile Cys Ser Pro Ala Ser Arg Ser Ile Ser Leu Leu Arg Leu Ser
                85                  90                  95

Phe His Gln Gly Cys Thr Ile Ala Ser Gln Arg Leu Thr Pro Leu Ala
            100                 105                 110

Arg Gly Asp Thr Leu Cys Thr Asn Leu Thr Gly Thr Leu Leu Pro Ser
        115                 120                 125

Arg Asn Thr Asp Glu Thr Phe Phe Gly Val Gln Trp Val Arg Pro Gly
    130                 135                 140

Ser Gly Ser Gly Asn Gly Ser Glu Ser Leu Gly Trp Asp Val Ala Glu
145                 150                 155                 160

Leu Gln Leu Asn His Thr Gly Pro Gln Gln Asp Pro Arg Leu Tyr Trp
            165                 170                 175

Gln Gly Gly Pro Ala Leu Gly Arg Ser Phe Leu His Gly Pro Glu Leu
        180                 185                 190

Asp Lys Gly Gln Leu Arg Ile His Arg Asp Gly Ile Tyr Met Val His
    195                 200                 205

Ile Gln Val Thr Leu Ala Ile Cys Ser Ser Thr Thr Ala Ser Arg His
210                 215                 220

His Pro Thr Thr Leu Ala Val Gly Ile Cys Ser Pro Ala Ser Arg Ser
225                 230                 235                 240

Ile Ser Leu Leu Arg Leu Ser Phe His Gln Gly Cys Thr Ile Ala Ser
            245                 250                 255

Gln Arg Leu Thr Pro Leu Ala Arg Gly Asp Thr Leu Cys Thr Asn Leu
        260                 265                 270

Thr Gly Thr Leu Leu Pro Ser Arg Asn Thr Asp Glu Thr Phe Phe Gly
    275                 280                 285

Val Gln Trp Val Arg Pro Gly Ser Gly Ser Glu Ser Leu Gly Trp Asp
290                 295                 300

Val Ala Glu Leu Gln Leu Asn His Thr Gly Pro Gln Gln Asp Pro Arg
305                 310                 315                 320

Leu Tyr Trp Gln Gly Gly Pro Ala Leu Gly Arg Ser Phe Leu His Gly
            325                 330                 335

Pro Glu Leu Asp Lys Gly Gln Leu Arg Ile His Arg Asp Gly Ile Tyr
        340                 345                 350

Met Val His Ile Gln Val Thr Leu Ala Ile Cys Ser Ser Thr Thr Ala
    355                 360                 365

Ser Arg His His Pro Thr Thr Leu Ala Val Gly Ile Cys Ser Pro Ala
370                 375                 380

Ser Arg Ser Ile Ser Leu Leu Arg Leu Ser Phe His Gln Gly Cys Thr
385                 390                 395                 400

Ile Ala Ser Gln Arg Leu Thr Pro Leu Ala Arg Gly Asp Thr Leu Cys
            405                 410                 415

Thr Asn Leu Thr Gly Thr Leu Leu Pro Ser Arg Asn Thr Asp Glu Thr
```

```
                420           425           430
Phe Phe Gly Val Gln Trp Val Arg Pro Gly Ser Ser Ser Ser Ser
            435                 440                 445

Ser Ser Gly Ser Cys Asp Lys Thr His Thr Cys Pro Pro Cys Pro Ala
        450                 455                 460

Pro Glu Leu Leu Gly Gly Pro Ser Val Phe Leu Phe Pro Pro Lys Pro
465                 470                 475                 480

Lys Asp Thr Leu Met Ile Ser Arg Thr Pro Glu Val Thr Cys Val Val
                485                 490                 495

Val Asp Val Ser His Glu Asp Pro Glu Val Lys Phe Asn Trp Tyr Val
            500                 505                 510

Asp Gly Val Glu Val His Asn Ala Lys Thr Lys Pro Arg Glu Glu Gln
        515                 520                 525

Tyr Ser Ser Thr Tyr Arg Val Val Ser Val Leu Thr Val Leu His Gln
    530                 535                 540

Asp Trp Leu Asn Gly Lys Glu Tyr Lys Cys Lys Val Ser Asn Lys Ala
545                 550                 555                 560

Leu Pro Ala Pro Ile Glu Lys Thr Ile Ser Lys Ala Lys Gly Gln Pro
                565                 570                 575

Arg Glu Pro Gln Val Tyr Thr Leu Pro Pro Ser Arg Glu Glu Met Thr
            580                 585                 590

Lys Asn Gln Val Ser Leu Thr Cys Leu Val Lys Gly Phe Tyr Pro Ser
        595                 600                 605

Asp Ile Ala Val Glu Trp Glu Ser Asn Gly Gln Pro Glu Asn Asn Tyr
    610                 615                 620

Lys Thr Thr Pro Pro Val Leu Asp Ser Asp Gly Ser Phe Phe Leu Tyr
625                 630                 635                 640

Ser Lys Leu Thr Val Asp Lys Ser Arg Trp Gln Gln Gly Asn Val Phe
                645                 650                 655

Ser Cys Ser Val Met His Glu Ala Leu His Asn His Tyr Thr Gln Lys
            660                 665                 670

Ser Leu Ser Leu Ser Pro Gly Lys
        675                 680

<210> SEQ ID NO 32
<211> LENGTH: 677
<212> TYPE: PRT
<213> ORGANISM: Artificial Sequence
<220> FEATURE:
<223> OTHER INFORMATION: Seq_31 with shorter hinge linker

<400> SEQUENCE: 32

Gln Ser Leu Gly Trp Asp Val Ala Glu Leu Gln Leu Asn His Thr Gly
1               5                   10                  15

Pro Gln Gln Asp Pro Arg Leu Tyr Trp Gln Gly Gly Pro Ala Leu Gly
            20                  25                  30

Arg Ser Phe Leu His Gly Pro Glu Leu Asp Lys Gly Gln Leu Arg Ile
        35                  40                  45

His Arg Asp Gly Ile Tyr Met Val His Ile Gln Val Thr Leu Ala Ile
    50                  55                  60

Cys Ser Ser Thr Thr Ala Ser Arg His His Pro Thr Thr Leu Ala Val
65                  70                  75                  80

Gly Ile Cys Ser Pro Ala Ser Arg Ser Ile Ser Leu Leu Arg Leu Ser
                85                  90                  95

Phe His Gln Gly Cys Thr Ile Ala Ser Gln Arg Leu Thr Pro Leu Ala
```

```
                100                 105                 110
Arg Gly Asp Thr Leu Cys Thr Asn Leu Thr Gly Thr Leu Leu Pro Ser
            115                 120                 125

Arg Asn Thr Asp Glu Thr Phe Phe Gly Val Gln Trp Val Arg Pro Gly
130                 135                 140

Ser Gly Ser Gly Asn Gly Ser Glu Ser Leu Gly Trp Asp Val Ala Glu
145                 150                 155                 160

Leu Gln Leu Asn His Thr Gly Pro Gln Gln Asp Pro Arg Leu Tyr Trp
                165                 170                 175

Gln Gly Gly Pro Ala Leu Gly Arg Ser Phe Leu His Gly Pro Glu Leu
            180                 185                 190

Asp Lys Gly Gln Leu Arg Ile His Arg Asp Gly Ile Tyr Met Val His
            195                 200                 205

Ile Gln Val Thr Leu Ala Ile Cys Ser Ser Thr Thr Ala Ser Arg His
210                 215                 220

His Pro Thr Thr Leu Ala Val Gly Ile Cys Ser Pro Ala Ser Arg Ser
225                 230                 235                 240

Ile Ser Leu Leu Arg Leu Ser Phe His Gln Gly Cys Thr Ile Ala Ser
                245                 250                 255

Gln Arg Leu Thr Pro Leu Ala Arg Gly Asp Thr Leu Cys Thr Asn Leu
            260                 265                 270

Thr Gly Thr Leu Leu Pro Ser Arg Asn Thr Asp Glu Thr Phe Phe Gly
            275                 280                 285

Val Gln Trp Val Arg Pro Gly Ser Gly Ser Glu Ser Leu Gly Trp Asp
    290                 295                 300

Val Ala Glu Leu Gln Leu Asn His Thr Gly Pro Gln Gln Asp Pro Arg
305                 310                 315                 320

Leu Tyr Trp Gln Gly Gly Pro Ala Leu Gly Arg Ser Phe Leu His Gly
                325                 330                 335

Pro Glu Leu Asp Lys Gly Gln Leu Arg Ile His Arg Asp Gly Ile Tyr
            340                 345                 350

Met Val His Ile Gln Val Thr Leu Ala Ile Cys Ser Ser Thr Thr Ala
            355                 360                 365

Ser Arg His His Pro Thr Thr Leu Ala Val Gly Ile Cys Ser Pro Ala
370                 375                 380

Ser Arg Ser Ile Ser Leu Leu Arg Leu Ser Phe His Gln Gly Cys Thr
385                 390                 395                 400

Ile Ala Ser Gln Arg Leu Thr Pro Leu Ala Arg Gly Asp Thr Leu Cys
                405                 410                 415

Thr Asn Leu Thr Gly Thr Leu Leu Pro Ser Arg Asn Thr Asp Glu Thr
            420                 425                 430

Phe Phe Gly Val Gln Trp Val Arg Pro Gly Ser Ser Ser Ser Ser Gly
            435                 440                 445

Ser Cys Asp Lys Thr His Thr Cys Pro Pro Cys Pro Ala Pro Glu Leu
450                 455                 460

Leu Gly Gly Pro Ser Val Phe Leu Phe Pro Pro Lys Pro Lys Asp Thr
465                 470                 475                 480

Leu Met Ile Ser Arg Thr Pro Glu Val Thr Cys Val Val Val Asp Val
                485                 490                 495

Ser His Glu Asp Pro Glu Val Lys Phe Asn Trp Tyr Val Asp Gly Val
            500                 505                 510

Glu Val His Asn Ala Lys Thr Lys Pro Arg Glu Glu Gln Tyr Ser Ser
            515                 520                 525
```

Thr Tyr Arg Val Val Ser Val Leu Thr Val Leu His Gln Asp Trp Leu
            530                 535                 540

Asn Gly Lys Glu Tyr Lys Cys Lys Val Ser Asn Lys Ala Leu Pro Ala
545                 550                 555                 560

Pro Ile Glu Lys Thr Ile Ser Lys Ala Lys Gly Gln Pro Arg Glu Pro
            565                 570                 575

Gln Val Tyr Thr Leu Pro Pro Ser Arg Glu Glu Met Thr Lys Asn Gln
            580                 585                 590

Val Ser Leu Thr Cys Leu Val Lys Gly Phe Tyr Pro Ser Asp Ile Ala
            595                 600                 605

Val Glu Trp Glu Ser Asn Gly Gln Pro Glu Asn Asn Tyr Lys Thr Thr
            610                 615                 620

Pro Pro Val Leu Asp Ser Asp Gly Ser Phe Phe Leu Tyr Ser Lys Leu
625                 630                 635                 640

Thr Val Asp Lys Ser Arg Trp Gln Gln Gly Asn Val Phe Ser Cys Ser
            645                 650                 655

Val Met His Glu Ala Leu His Asn His Tyr Thr Gln Lys Ser Leu Ser
            660                 665                 670

Leu Ser Pro Gly Lys
            675

<210> SEQ ID NO 33
<211> LENGTH: 663
<212> TYPE: PRT
<213> ORGANISM: Artificial Sequence
<220> FEATURE:
<223> OTHER INFORMATION: example with N-terminal shortened RBD modules

<400> SEQUENCE: 33

Gln Asp Val Ala Glu Leu Gln Leu Asn His Thr Gly Pro Gln Gln Asp
1               5                   10                  15

Pro Arg Leu Tyr Trp Gln Gly Gly Pro Ala Leu Gly Arg Ser Phe Leu
            20                  25                  30

His Gly Pro Glu Leu Asp Lys Gly Gln Leu Arg Ile His Arg Asp Gly
            35                  40                  45

Ile Tyr Met Val His Ile Gln Val Thr Leu Ala Ile Cys Ser Ser Thr
50                  55                  60

Thr Ala Ser Arg His His Pro Thr Thr Leu Ala Val Gly Ile Cys Ser
65                  70                  75                  80

Pro Ala Ser Arg Ser Ile Ser Leu Leu Arg Leu Ser Phe His Gln Gly
            85                  90                  95

Cys Thr Ile Ala Ser Gln Arg Leu Thr Pro Leu Ala Arg Gly Asp Thr
            100                 105                 110

Leu Cys Thr Asn Leu Thr Gly Thr Leu Leu Pro Ser Arg Asn Thr Asp
            115                 120                 125

Glu Thr Phe Phe Gly Val Gln Trp Val Arg Pro Gly Ser Gly Ser Gly
            130                 135                 140

Asn Gly Ser Asp Val Ala Glu Leu Gln Leu Asn His Thr Gly Pro Gln
145                 150                 155                 160

Gln Asp Pro Arg Leu Tyr Trp Gln Gly Gly Pro Ala Leu Gly Arg Ser
            165                 170                 175

Phe Leu His Gly Pro Glu Leu Asp Lys Gly Gln Leu Arg Ile His Arg
            180                 185                 190

Asp Gly Ile Tyr Met Val His Ile Gln Val Thr Leu Ala Ile Cys Ser
            195                 200                 205

```
Ser Thr Thr Ala Ser Arg His His Pro Thr Thr Leu Ala Val Gly Ile
    210                 215                 220

Cys Ser Pro Ala Ser Arg Ser Ile Ser Leu Leu Arg Leu Ser Phe His
225                 230                 235                 240

Gln Gly Cys Thr Ile Ala Ser Gln Arg Leu Thr Pro Leu Ala Arg Gly
                245                 250                 255

Asp Thr Leu Cys Thr Asn Leu Thr Gly Thr Leu Leu Pro Ser Arg Asn
                260                 265                 270

Thr Asp Glu Thr Phe Phe Gly Val Gln Trp Val Arg Pro Gly Ser Gly
            275                 280                 285

Ser Asp Val Ala Glu Leu Gln Leu Asn His Thr Gly Pro Gln Gln Asp
290                 295                 300

Pro Arg Leu Tyr Trp Gln Gly Pro Ala Leu Gly Arg Ser Phe Leu
305                 310                 315                 320

His Gly Pro Glu Leu Asp Lys Gly Gln Leu Arg Ile His Arg Asp Gly
                325                 330                 335

Ile Tyr Met Val His Ile Gln Val Thr Leu Ala Ile Cys Ser Ser Thr
                340                 345                 350

Thr Ala Ser Arg His His Pro Thr Thr Leu Ala Val Gly Ile Cys Ser
        355                 360                 365

Pro Ala Ser Arg Ser Ile Ser Leu Leu Arg Leu Ser Phe His Gln Gly
370                 375                 380

Cys Thr Ile Ala Ser Gln Arg Leu Thr Pro Leu Ala Arg Gly Asp Thr
385                 390                 395                 400

Leu Cys Thr Asn Leu Thr Gly Thr Leu Leu Pro Ser Arg Asn Thr Asp
                405                 410                 415

Glu Thr Phe Phe Gly Val Gln Trp Val Arg Pro Gly Ser Ser Ser Ser
            420                 425                 430

Ser Gly Ser Cys Asp Lys Thr His Thr Cys Pro Pro Cys Pro Ala Pro
            435                 440                 445

Glu Leu Leu Gly Gly Pro Ser Val Phe Leu Phe Pro Pro Lys Pro Lys
450                 455                 460

Asp Thr Leu Met Ile Ser Arg Thr Pro Glu Val Thr Cys Val Val Val
465                 470                 475                 480

Asp Val Ser His Glu Asp Pro Glu Val Lys Phe Asn Trp Tyr Val Asp
                485                 490                 495

Gly Val Glu Val His Asn Ala Lys Thr Lys Pro Arg Glu Glu Gln Tyr
            500                 505                 510

Ser Ser Thr Tyr Arg Val Val Ser Val Leu Thr Val Leu His Gln Asp
        515                 520                 525

Trp Leu Asn Gly Lys Glu Tyr Lys Cys Lys Val Ser Asn Lys Ala Leu
530                 535                 540

Pro Ala Pro Ile Glu Lys Thr Ile Ser Lys Ala Lys Gly Gln Pro Arg
545                 550                 555                 560

Glu Pro Gln Val Tyr Thr Leu Pro Pro Ser Arg Glu Glu Met Thr Lys
                565                 570                 575

Asn Gln Val Ser Leu Thr Cys Leu Val Lys Gly Phe Tyr Pro Ser Asp
            580                 585                 590

Ile Ala Val Glu Trp Glu Ser Asn Gly Gln Pro Glu Asn Asn Tyr Lys
        595                 600                 605

Thr Thr Pro Pro Val Leu Asp Ser Asp Gly Ser Phe Phe Leu Tyr Ser
    610                 615                 620
```

```
Lys Leu Thr Val Asp Lys Ser Arg Trp Gln Gln Gly Asn Val Phe Ser
625                 630                 635                 640

Cys Ser Val Met His Glu Ala Leu His Asn His Tyr Thr Gln Lys Ser
            645                 650                 655

Leu Ser Leu Ser Pro Gly Lys
            660

<210> SEQ ID NO 34
<211> LENGTH: 681
<212> TYPE: PRT
<213> ORGANISM: Artificial Sequence
<220> FEATURE:
<223> OTHER INFORMATION: example

<400> SEQUENCE: 34

Gln Ser Leu Gly Trp Asp Val Ala Glu Leu Gln Leu Asn His Thr Gly
1               5                   10                  15

Pro Gln Gln Asp Pro Arg Leu Tyr Trp Gln Gly Gly Pro Ala Leu Gly
            20                  25                  30

Arg Ser Phe Leu His Gly Pro Glu Leu Asp Lys Gly Gln Leu Arg Ile
        35                  40                  45

His Arg Asp Gly Ile Tyr Met Val His Ile Gln Val Thr Leu Ala Ile
50                  55                  60

Cys Ser Ser Thr Thr Ala Ser Arg His His Pro Thr Thr Leu Ala Val
65                  70                  75                  80

Gly Ile Cys Ser Pro Ala Ser Arg Ser Ile Ser Leu Leu Arg Leu Ser
                85                  90                  95

Phe His Gln Gly Cys Thr Ile Ala Ser Gln Arg Leu Thr Pro Leu Ala
            100                 105                 110

Arg Gly Asp Thr Leu Cys Thr Asn Leu Thr Gly Thr Leu Leu Pro Ser
        115                 120                 125

Arg Asn Thr Asp Glu Thr Phe Phe Gly Val Gln Trp Val Arg Pro Gly
130                 135                 140

Ser Gly Ser Gly Asn Gly Ser Glu Ser Leu Gly Trp Asp Val Ala Glu
145                 150                 155                 160

Leu Gln Leu Asn His Thr Gly Pro Gln Gln Asp Pro Arg Leu Tyr Trp
                165                 170                 175

Gln Gly Gly Pro Ala Leu Gly Arg Ser Phe Leu His Gly Pro Glu Leu
            180                 185                 190

Asp Lys Gly Gln Leu Arg Ile His Arg Asp Gly Ile Tyr Met Val His
        195                 200                 205

Ile Gln Val Thr Leu Ala Ile Cys Ser Ser Thr Thr Ala Ser Arg His
210                 215                 220

His Pro Thr Thr Leu Ala Val Gly Ile Cys Ser Pro Ala Ser Arg Ser
225                 230                 235                 240

Ile Ser Leu Leu Arg Leu Ser Phe His Gln Gly Cys Thr Ile Ala Ser
                245                 250                 255

Gln Arg Leu Thr Pro Leu Ala Arg Gly Asp Thr Leu Cys Thr Asn Leu
            260                 265                 270

Thr Gly Thr Leu Leu Pro Ser Arg Asn Thr Asp Glu Thr Phe Phe Gly
        275                 280                 285

Val Gln Trp Val Arg Pro Gly Ser Gly Ser Gly Asn Gly Ser Glu Ser
290                 295                 300

Leu Gly Trp Asp Val Ala Glu Leu Gln Leu Asn His Thr Gly Pro Gln
305                 310                 315                 320
```

Gln Asp Pro Arg Leu Tyr Trp Gln Gly Gly Pro Ala Leu Gly Arg Ser
            325                 330                 335

Phe Leu His Gly Pro Glu Leu Asp Lys Gly Gln Leu Arg Ile His Arg
        340                 345                 350

Asp Gly Ile Tyr Met Val His Ile Gln Val Thr Leu Ala Ile Cys Ser
        355                 360                 365

Ser Thr Thr Ala Ser Arg His His Pro Thr Thr Leu Ala Val Gly Ile
    370                 375                 380

Cys Ser Pro Ala Ser Ser Ile Ser Leu Leu Arg Leu Ser Phe His
385                 390                 395                 400

Gln Gly Cys Thr Ile Ala Ser Gln Arg Leu Thr Pro Leu Ala Arg Gly
                405                 410                 415

Asp Thr Leu Cys Thr Asn Leu Thr Gly Thr Leu Leu Pro Ser Arg Asn
                420                 425                 430

Thr Asp Glu Thr Phe Phe Gly Val Gln Trp Val Arg Pro Gly Ser Ser
            435                 440                 445

Ser Ser Ser Gly Ser Cys Asp Lys Thr His Thr Cys Pro Pro Cys Pro
    450                 455                 460

Ala Pro Glu Leu Leu Gly Gly Pro Ser Val Phe Leu Phe Pro Pro Lys
465                 470                 475                 480

Pro Lys Asp Thr Leu Met Ile Ser Arg Thr Pro Glu Val Thr Cys Val
                485                 490                 495

Val Val Asp Val Ser His Glu Asp Pro Glu Val Lys Phe Asn Trp Tyr
                500                 505                 510

Val Asp Gly Val Glu Val His Asn Ala Lys Thr Lys Pro Arg Glu Glu
            515                 520                 525

Gln Tyr Ser Ser Thr Tyr Arg Val Val Ser Val Leu Thr Val Leu His
    530                 535                 540

Gln Asp Trp Leu Asn Gly Lys Glu Tyr Lys Cys Lys Val Ser Asn Lys
545                 550                 555                 560

Ala Leu Pro Ala Pro Ile Glu Lys Thr Ile Ser Lys Ala Lys Gly Gln
                565                 570                 575

Pro Arg Glu Pro Gln Val Tyr Thr Leu Pro Pro Ser Arg Glu Glu Met
            580                 585                 590

Thr Lys Asn Gln Val Ser Leu Thr Cys Leu Val Lys Gly Phe Tyr Pro
    595                 600                 605

Ser Asp Ile Ala Val Glu Trp Glu Ser Asn Gly Gln Pro Glu Asn Asn
610                 615                 620

Tyr Lys Thr Thr Pro Pro Val Leu Asp Ser Asp Gly Ser Phe Phe Leu
                625                 630                 635                 640

Tyr Ser Lys Leu Thr Val Asp Lys Ser Arg Trp Gln Gln Gly Asn Val
            645                 650                 655

Phe Ser Cys Ser Val Met His Glu Ala Leu His Asn His Tyr Thr Gln
    660                 665                 670

Lys Ser Leu Ser Leu Ser Pro Gly Lys
675                 680

<210> SEQ ID NO 35
<211> LENGTH: 684
<212> TYPE: PRT
<213> ORGANISM: Artificial Sequence
<220> FEATURE:
<223> OTHER INFORMATION: SEQ39+SEQ16+SEQ13

<400> SEQUENCE: 35

-continued

```
Glu Ser Leu Gly Trp Asp Val Ala Glu Leu Gln Leu Asp His Thr Gly
1               5                   10                  15
Pro Gln Gln Asp Pro Arg Leu Tyr Trp Gln Gly Gly Pro Ala Leu Gly
                20                  25                  30
Arg Ser Phe Leu His Gly Pro Glu Leu Asp Lys Gly Gln Leu Arg Ile
            35                  40                  45
His Arg Asp Gly Ile Tyr Met Val His Ile Gln Val Thr Leu Ala Ile
        50                  55                  60
Cys Ser Ser Thr Thr Ala Ser Arg His His Pro Thr Thr Leu Ala Val
65                  70                  75                  80
Gly Ile Cys Ser Pro Ala Ser Arg Ser Ile Ser Leu Leu Arg Leu Ser
                85                  90                  95
Phe His Gln Gly Cys Thr Ile Ala Ser Gln Arg Leu Thr Pro Leu Ala
                100                 105                 110
Arg Gly Asp Thr Leu Cys Thr Asn Leu Thr Gly Thr Leu Leu Pro Ser
            115                 120                 125
Arg Asn Thr Asp Glu Thr Phe Phe Gly Val Gln Trp Val Arg Pro Gly
        130                 135                 140
Ser Gly Ser Gly Asn Gly Ser Glu Ser Leu Gly Trp Asp Val Ala Glu
145                 150                 155                 160
Leu Gln Leu Asp His Thr Gly Pro Gln Gln Asp Pro Arg Leu Tyr Trp
                165                 170                 175
Gln Gly Gly Pro Ala Leu Gly Arg Ser Phe Leu His Gly Pro Glu Leu
                180                 185                 190
Asp Lys Gly Gln Leu Arg Ile His Arg Asp Gly Ile Tyr Met Val His
            195                 200                 205
Ile Gln Val Thr Leu Ala Ile Cys Ser Ser Thr Thr Ala Ser Arg His
        210                 215                 220
His Pro Thr Thr Leu Ala Val Gly Ile Cys Ser Pro Ala Ser Arg Ser
225                 230                 235                 240
Ile Ser Leu Leu Arg Leu Ser Phe His Gln Gly Cys Thr Ile Ala Ser
                245                 250                 255
Gln Arg Leu Thr Pro Leu Ala Arg Gly Asp Thr Leu Cys Thr Asn Leu
                260                 265                 270
Thr Gly Thr Leu Leu Pro Ser Arg Asn Thr Asp Glu Thr Phe Phe Gly
            275                 280                 285
Val Gln Trp Val Arg Pro Gly Ser Gly Ser Gly Asn Gly Ser Glu Ser
        290                 295                 300
Leu Gly Trp Asp Val Ala Glu Leu Gln Leu Asp His Thr Gly Pro Gln
305                 310                 315                 320
Gln Asp Pro Arg Leu Tyr Trp Gln Gly Gly Pro Ala Leu Gly Arg Ser
                325                 330                 335
Phe Leu His Gly Pro Glu Leu Asp Lys Gly Gln Leu Arg Ile His Arg
                340                 345                 350
Asp Gly Ile Tyr Met Val His Ile Gln Val Thr Leu Ala Ile Cys Ser
            355                 360                 365
Ser Thr Thr Ala Ser Arg His His Pro Thr Thr Leu Ala Val Gly Ile
        370                 375                 380
Cys Ser Pro Ala Ser Arg Ser Ile Ser Leu Leu Arg Leu Ser Phe His
385                 390                 395                 400
Gln Gly Cys Thr Ile Ala Ser Gln Arg Leu Thr Pro Leu Ala Arg Gly
                405                 410                 415
Asp Thr Leu Cys Thr Asn Leu Thr Gly Thr Leu Leu Pro Ser Arg Asn
```

```
                    420              425                430
        Thr Asp Glu Thr Phe Phe Gly Val Gln Trp Val Arg Pro Gly Ser Ser
                    435              440                445

Ser Ser Ser Ser Ser Ser Gly Ser Cys Asp Lys Thr His Thr Cys Pro
            450              455                460

Pro Cys Pro Ala Pro Glu Leu Leu Gly Gly Pro Ser Val Phe Leu Phe
        465              470              475                480

Pro Pro Lys Pro Lys Asp Thr Leu Met Ile Ser Arg Thr Pro Glu Val
                    485              490                495

Thr Cys Val Val Val Asp Val Ser His Glu Asp Pro Glu Val Lys Phe
                500              505                510

Asn Trp Tyr Val Asp Gly Val Glu Val His Asn Ala Lys Thr Lys Pro
                    515              520                525

Arg Glu Glu Gln Tyr Ser Thr Tyr Arg Val Val Ser Val Leu Thr
                530              535              540

Val Leu His Gln Asp Trp Leu Asn Gly Lys Glu Tyr Lys Cys Lys Val
        545              550              555                560

Ser Asn Lys Ala Leu Pro Ala Pro Ile Glu Lys Thr Ile Ser Lys Ala
                    565              570                575

Lys Gly Gln Pro Arg Glu Pro Gln Val Tyr Thr Leu Pro Pro Ser Arg
                    580              585                590

Glu Glu Met Thr Lys Asn Gln Val Ser Leu Thr Cys Leu Val Lys Gly
                    595              600                605

Phe Tyr Pro Ser Asp Ile Ala Val Glu Trp Glu Ser Asn Gly Gln Pro
                    610              615                620

Glu Asn Asn Tyr Lys Thr Thr Pro Pro Val Leu Asp Ser Asp Gly Ser
        625              630              635                640

Phe Phe Leu Tyr Ser Lys Leu Thr Val Asp Lys Ser Arg Trp Gln Gln
                    645              650                655

Gly Asn Val Phe Ser Cys Ser Val Met His Glu Ala Leu His Asn His
                    660              665                670

Tyr Thr Gln Lys Ser Leu Ser Leu Ser Pro Gly Lys
                    675              680

<210> SEQ ID NO 36
<211> LENGTH: 446
<212> TYPE: PRT
<213> ORGANISM: Artificial Sequence
<220> FEATURE:
<223> OTHER INFORMATION: Exemplary scCD27L-RBD module

<400> SEQUENCE: 36

Gln Ser Leu Gly Trp Asp Val Ala Glu Leu Gln Leu Asn His Thr Gly
        1               5                  10                 15

Pro Gln Gln Asp Pro Arg Leu Tyr Trp Gln Gly Gly Pro Ala Leu Gly
                    20              25                30

Arg Ser Phe Leu His Gly Pro Glu Leu Asp Lys Gly G

```
                100             105             110
Arg Gly Asp Thr Leu Cys Thr Asn Leu Thr Gly Thr Leu Leu Pro Ser
            115                 120                 125

Arg Asn Thr Asp Glu Thr Phe Phe Gly Val Gln Trp Val Arg Pro Gly
            130                 135             140

Ser Gly Ser Gly Asn Gly Ser Glu Ser Leu Gly Trp Asp Val Ala Glu
145                 150                 155                 160

Leu Gln Leu Asn His Thr Gly Pro Gln Gln Asp Pro Arg Leu Tyr Trp
                165                 170                 175

Gln Gly Gly Pro Ala Leu Gly Arg Ser Phe Leu His Gly Pro Glu Leu
            180                 185                 190

Asp Lys Gly Gln Leu Arg Ile His Arg Asp Gly Ile Tyr Met Val His
            195                 200                 205

Ile Gln Val Thr Leu Ala Ile Cys Ser Ser Thr Ala Ser Arg His
210                 215                 220

His Pro Thr Thr Leu Ala Val Gly Ile Cys Ser Pro Ala Ser Arg Ser
225                 230                 235                 240

Ile Ser Leu Leu Arg Leu Ser Phe His Gln Gly Cys Thr Ile Ala Ser
                245                 250                 255

Gln Arg Leu Thr Pro Leu Ala Arg Gly Asp Thr Leu Cys Thr Asn Leu
            260                 265                 270

Thr Gly Thr Leu Leu Pro Ser Arg Asn Thr Asp Glu Thr Phe Phe Gly
            275                 280                 285

Val Gln Trp Val Arg Pro Gly Ser Gly Ser Gly Asn Gly Ser Glu Ser
            290                 295                 300

Leu Gly Trp Asp Val Ala Glu Leu Gln Leu Asn His Thr Gly Pro Gln
305                 310                 315                 320

Gln Asp Pro Arg Leu Tyr Trp Gln Gly Gly Pro Ala Leu Gly Arg Ser
                325                 330                 335

Phe Leu His Gly Pro Glu Leu Asp Lys Gly Gln Leu Arg Ile His Arg
            340                 345                 350

Asp Gly Ile Tyr Met Val His Ile Gln Val Thr Leu Ala Ile Cys Ser
            355                 360                 365

Ser Thr Ala Ser Arg His His Pro Thr Thr Leu Ala Val Gly Ile
370                 375                 380

Cys Ser Pro Ala Ser Arg Ser Ile Ser Leu Leu Arg Leu Ser Phe His
385                 390                 395                 400

Gln Gly Cys Thr Ile Ala Ser Gln Arg Leu Thr Pro Leu Ala Arg Gly
                405                 410                 415

Asp Thr Leu Cys Thr Asn Leu Thr Gly Thr Leu Leu Pro Ser Arg Asn
            420                 425                 430

Thr Asp Glu Thr Phe Phe Gly Val Gln Trp Val Arg Pro Gly
            435                 440                 445
```

<210> SEQ ID NO 37
<211> LENGTH: 2159
<212> TYPE: DNA
<213> ORGANISM: Artificial Sequence
<220> FEATURE:
<223> OTHER INFORMATION: DNA sequence encoding SEQ_25

<400> SEQUENCE: 37
aagctttagg gataacaggg taatagccgc caccatggag actgacaccc tgctggtgtt    60
cgtgctgctg gtctgggtgc ctgcaggaaa tggagagagc ctgggatggg atgtggccga   120

| | |
|---|---|
| actccagctg aaccacacag gccctcagca agaccctagg ctctactggc agggcggccc | 180 |
| tgctctggga aggagctttc tgcatggccc tgaactggat aaaggccaac tgcgtattca | 240 |
| tcgggatggc atttacatgg tccatatcca ggtgaccctc gccatctgct ccagcaccac | 300 |
| cgctagcagg catcatccca ccaccctggc cgtgggcatt tgttcccctg ccagccggtc | 360 |
| catctccctg ctgaggctga gctttcatca gggctgcacc atcgcctccc aaaggctgac | 420 |
| ccctctggcc aggggcgata cactgtgtac caatctgacc ggcaccctgc tcccagcag | 480 |
| gaacaccgat gaaaccttt tcggagtgca gtgggtgcgg cctggttccg aagcggcaa | 540 |
| tggctccgaa agcctcggct gggacgtggc cgagctccaa ctgaaccaca ccggccctca | 600 |
| acaagatcct cggctctatt ggcaaggcgg acctgctctc ggccggagct tcctgcatgg | 660 |
| ccctgagctg acaagggcc agctgcgtat catcgggat ggaatctata tggtgcacat | 720 |
| ccaagtgaca ctggccattt gcagcagcac caccgctagc cggcaccatc ctaccaccct | 780 |
| ggctgtgggc atctgttccc ccgctagccg gtccatctcc ctgctgaggc tgagcttcca | 840 |
| ccagggctgt accatcgcca gccagaggct gacccctctg ctaggggcg acaccctgtg | 900 |
| taccaacctg accggaaccc tgctgcctag caggaatacc gatgagacct tcttcggagt | 960 |
| gcaatgggtg aggcctggct ctggttctgg taacggttct gagagcctcg gctgggacgt | 1020 |
| cgctgaactg cagctgaatc acacaggccc cagcaggac cctaggctgt actggcaggg | 1080 |
| aggccctgct ctcggaagga gctttctgca cggccctgaa ctggataagg acagctccg | 1140 |
| tattcatcgg gatggcatct acatggtgca tatccaggtc accctggcca tctgcagctc | 1200 |
| caccaccgcc tccaggcacc accctaccac cctggctgtg gcatctgct cccctgcctc | 1260 |
| ccggagcatc agcctgctga ggctgtcctt ccaccaaggc tgcaccatcg ctagccaaag | 1320 |
| gctgaccct ctggctaggg gcgataccct gtgcaccaac ctgaccggaa ccctgctgcc | 1380 |
| ttcccggaac accgacgaga ccttttcgg cgtgcagtgg gtcaggcccg gatcctcgag | 1440 |
| ttcatcgtcc tcatccggct catgtgataa gacccacacc tgccctccct gtcctgcccc | 1500 |
| tgagctgctg gcggaccttt ctgtgttcct gttccccccc aagcctaagg acaccctgat | 1560 |
| gatctccagg acccctgagg tgacctgtgt ggtggtggac gtgtctcacg aagatccga | 1620 |
| ggtgaagttc aactggtacg tggacggcgt ggaggtccac aacgccaaga ccaagcctag | 1680 |
| ggaggagcag tacagctcca cctacccggg ggtgtctgtg ctgaccgtgc tgcaccagga | 1740 |
| ttggctgaac ggaaaggagt ataagtgtaa ggtctccaac aaggccctgc ctgcccccat | 1800 |
| cgagaaaacc atctccaagg ccaagggcca gcctcgggag cctcaggtgt acaccctgcc | 1860 |
| tcctagcagg gaggagatga ccaagaacca ggtgtccctg acctgtctgg tgaagggctt | 1920 |
| ctacccttcc gatatcgccg tggagtggga gtctaatggc cagccgaga caactacaa | 1980 |
| gaccacccct cctgtgctgg actctgacgg ctccttcttc ctgtactcca gctgaccgt | 2040 |
| ggacaagtcc agatggcagc agggcaacgt gttctcctgc tccgtgatgc acgaggccct | 2100 |
| gcacaatcac tacacccaga agtccctgtc tctgagtccg ggcaagtaat aggcgcgcc | 2159 |

<210> SEQ ID NO 38
<211> LENGTH: 220
<212> TYPE: PRT
<213> ORGANISM: Artificial Sequence
<220> FEATURE:
<223> OTHER INFORMATION: CD27L RBD fused to RB69-Foldon

<400> SEQUENCE: 38

Met Glu Thr Asp Thr Leu Leu Val Phe Val Leu Leu Val Trp Val Pro

```
                1               5                  10                 15
            Ala Gly Asn Gly Glu Ser Leu Gly Trp Asp Val Ala Glu Leu Gln Leu
                            20                 25                 30

Asn His Thr Gly Pro Gln Gln Asp Pro Arg Leu Tyr Trp Gln Gly Gly
                        35                 40                 45

Pro Ala Leu Gly Arg Ser Phe Leu His Gly Pro Glu Leu Asp Lys Gly
                    50                 55                 60

Gln Leu Arg Ile His Arg Asp Gly Ile Tyr Met Val His Ile Gln Val
            65                 70                 75                 80

Thr Leu Ala Ile Cys Ser Ser Thr Thr Ala Ser Arg His His Pro Thr
                                85                 90                 95

Thr Leu Ala Val Gly Ile Cys Ser Pro Ala Ser Arg Ser Ile Ser Leu
                            100                105                110

Leu Arg Leu Ser Phe His Gln Gly Cys Thr Ile Ala Ser Gln Arg Leu
                        115                120                125

Thr Pro Leu Ala Arg Gly Asp Thr Leu Cys Thr Asn Leu Thr Gly Thr
                    130                135                140

Leu Leu Pro Ser Arg Asn Thr Asp Glu Thr Phe Phe Gly Val Gln Trp
            145                150                155                160

Val Arg Pro Gly Ser Gly Ser Ser Gly Ser Gly Ser Ser Gly Ser
                                165                170                175

Gly Tyr Ile Glu Asp Ala Pro Ser Asp Gly Lys Phe Tyr Val Arg Lys
                            180                185                190

Asp Gly Ala Trp Val Glu Leu Pro Thr Ala Ser Gly Pro Ser Ser Ser
                        195                200                205

Ser Ser Ser Ala Trp Ser His Pro Gln Phe Glu Lys
                    210                215                220

<210> SEQ ID NO 39
<211> LENGTH: 445
<212> TYPE: PRT
<213> ORGANISM: Artificial Sequence
<220> FEATURE:
<223> OTHER INFORMATION: exemplary scCD27L-RBD module

<400> SEQUENCE: 39

Glu Ser Leu Gly Trp Asp Val Ala Glu Leu Gln Leu Asp His Thr Gly
            1               5                  10                 15

Pro Gln Gln Asp Pro Arg Leu Tyr Trp Gln Gly Gly P

```
145                 150                 155                 160

Leu Gln Leu Asp His Thr Gly Pro Gln Gln Asp Pro Arg Leu Tyr Trp
                165                 170                 175

Gln Gly Gly Pro Ala Leu Gly Arg Ser Phe Leu His Gly Pro Glu Leu
            180                 185                 190

Asp Lys Gly Gln Leu Arg Ile His Arg Asp Gly Ile Tyr Met Val His
        195                 200                 205

Ile Gln Val Thr Leu Ala Ile Cys Ser Ser Thr Thr Ala Ser Arg His
    210                 215                 220

His Pro Thr Thr Leu Ala Val Gly Ile Cys Ser Pro Ala Ser Arg Ser
225                 230                 235                 240

Ile Ser Leu Leu Arg Leu Ser Phe His Gln Gly Cys Thr Ile Ala Ser
                245                 250                 255

Gln Arg Leu Thr Pro Leu Ala Arg Gly Asp Thr Leu Cys Thr Asn Leu
            260                 265                 270

Thr Gly Thr Leu Leu Pro Ser Arg Asn Thr Asp Glu Thr Phe Phe Gly
        275                 280                 285

Val Gln Trp Val Arg Pro Gly Ser Gly Ser Gly Asn Gly Ser Glu Ser
    290                 295                 300

Leu Gly Trp Asp Val Ala Glu Leu Gln Leu Asp His Thr Gly Pro Gln
305                 310                 315                 320

Gln Asp Pro Arg Leu Tyr Trp Gln Gly Gly Pro Ala Leu Gly Arg Ser
                325                 330                 335

Phe Leu His Gly Pro Glu Leu Asp Lys Gly Gln Leu Arg Ile His Arg
            340                 345                 350

Asp Gly Ile Tyr Met Val His Ile Gln Val Thr Leu Ala Ile Cys Ser
        355                 360                 365

Ser Thr Thr Ala Ser Arg His His Pro Thr Thr Leu Ala Val Gly Ile
    370                 375                 380

Cys Ser Pro Ala Ser Arg Ser Ile Ser Leu Leu Arg Leu Ser Phe His
385                 390                 395                 400

Gln Gly Cys Thr Ile Ala Ser Gln Arg Leu Thr Pro Leu Ala Arg Gly
                405                 410                 415

Asp Thr Leu Cys Thr Asn Leu Thr Gly Thr Leu Leu Pro Ser Arg Asn
            420                 425                 430

Thr Asp Glu Thr Phe Phe Gly Val Gln Trp Val Arg Pro
        435                 440                 445

<210> SEQ ID NO 40
<211> LENGTH: 441
<212> TYPE: PRT
<213> ORGANISM: Artificial Sequence
<220> FEATURE:
<223> OTHER INFORMATION: exemplary scCD27L-RBD module

<400> SEQUENCE: 40

Glu Ser Leu Gly Trp Asp Val Ala Glu Leu Gln Leu Asp His Thr Gly
1               5                   10                  15

Pro Gln Gln Asp Pro Arg Leu Tyr Trp Gln Gly Gly Pro Ala Leu Gly
            20                  25                  30

Arg Ser Phe Leu His Gly Pro Glu Leu Asp Lys Gly Gln Leu Arg Ile
        35                  40                  45

His Arg Asp Gly Ile Tyr Met Val His Ile Gln Val Thr Leu Ala Ile
    50                  55                  60

Cys Ser Ser Thr Thr Ala Ser Arg His His Pro Thr Thr Leu Ala Val
```

```
                65                  70                  75                  80
Gly Ile Cys Ser Pro Ala Ser Arg Ser Ile Ser Leu Leu Arg Leu Ser
                    85                  90                  95

Phe His Gln Gly Cys Thr Ile Ala Ser Gln Arg Leu Thr Pro Leu Ala
                    100                 105                 110

Arg Gly Asp Thr Leu Cys Thr Asn Leu Thr Gly Thr Leu Leu Pro Ser
                    115                 120                 125

Arg Asn Thr Asp Glu Thr Phe Phe Gly Val Gln Trp Val Arg Pro Gly
                    130                 135                 140

Ser Gly Ser Gly Asn Gly Ser Glu Ser Leu Gly Trp Asp Val Ala Glu
145                 150                 155                 160

Leu Gln Leu Asp His Thr Gly Pro Gln Gln Asp Pro Arg Leu Tyr Trp
                    165                 170                 175

Gln Gly Gly Pro Ala Leu Gly Arg Ser Phe Leu His Gly Pro Glu Leu
                    180                 185                 190

Asp Lys Gly Gln Leu Arg Ile His Arg Asp Gly Ile Tyr Met Val His
                    195                 200                 205

Ile Gln Val Thr Leu Ala Ile Cys Ser Ser Thr Thr Ala Ser Arg His
                    210                 215                 220

His Pro Thr Thr Leu Ala Val Gly Ile Cys Ser Pro Ala Ser Arg Ser
225                 230                 235                 240

Ile Ser Leu Leu Arg Leu Ser Phe His Gln Gly Cys Thr Ile Ala Ser
                    245                 250                 255

Gln Arg Leu Thr Pro Leu Ala Arg Gly Asp Thr Leu Cys Thr Asn Leu
                    260                 265                 270

Thr Gly Thr Leu Leu Pro Ser Arg Asn Thr Asp Glu Thr Phe Phe Gly
                    275                 280                 285

Val Gln Trp Val Arg Pro Gly Ser Gly Ser Glu Ser Leu Gly Trp Asp
                    290                 295                 300

Val Ala Glu Leu Gln Leu Asp His Thr Gly Pro Gln Gln Asp Pro Arg
305                 310                 315                 320

Leu Tyr Trp Gln Gly Gly Pro Ala Leu Gly Arg Ser Phe Leu His Gly
                    325                 330                 335

Pro Glu Leu Asp Lys Gly Gln Leu Arg Ile His Arg Asp Gly Ile Tyr
                    340                 345                 350

Met Val His Ile Gln Val Thr Leu Ala Ile Cys Ser Ser Thr Thr Ala
                    355                 360                 365

Ser Arg His His Pro Thr Thr Leu Ala Val Gly Ile Cys Ser Pro Ala
370                 375                 380

Ser Arg Ser Ile Ser Leu Leu Arg Leu Ser Phe His Gln Gly Cys Thr
385                 390                 395                 400

Ile Ala Ser Gln Arg Leu Thr Pro Leu Ala Arg Gly Asp Thr Leu Cys
                    405                 410                 415

Thr Asn Leu Thr Gly Thr Leu Leu Pro Ser Arg Asn Thr Asp Glu Thr
                    420                 425                 430

Phe Phe Gly Val Gln Trp Val Arg Pro
                    435                 440

<210> SEQ ID NO 41
<211> LENGTH: 430
<212> TYPE: PRT
<213> ORGANISM: Artificial Sequence
<220> FEATURE:
<223> OTHER INFORMATION: exemplary scCD27L-RBD module
```

```
<400> SEQUENCE: 41

Asp Val Ala Glu Leu Gln Leu Asp His Thr Gly Pro Gln Gln Asp Pro
1               5                   10                  15

Arg Leu Tyr Trp Gln Gly Gly Pro Ala Leu Gly Arg Ser Phe Leu His
            20                  25                  30

Gly Pro Glu Leu Asp Lys Gly Gln Leu Arg Ile His Arg Asp Gly Ile
        35                  40                  45

Tyr Met Val His Ile Gln Val Thr Leu Ala Ile Cys Ser Ser Thr Thr
    50                  55                  60

Ala Ser Arg His His Pro Thr Thr Leu Ala Val Gly Ile Cys Ser Pro
65                  70                  75                  80

Ala Ser Arg Ser Ile Ser Leu Leu Arg Leu Ser Phe His Gln Gly Cys
                85                  90                  95

Thr Ile Ala Ser Gln Arg Leu Thr Pro Leu Ala Arg Gly Asp Thr Leu
            100                 105                 110

Cys Thr Asn Leu Thr Gly Thr Leu Leu Pro Ser Arg Asn Thr Asp Glu
        115                 120                 125

Thr Phe Phe Gly Val Gln Trp Val Arg Pro Gly Ser Gly Ser Gly Asn
    130                 135                 140

Gly Ser Asp Val Ala Glu Leu Gln Leu Asp His Thr Gly Pro Gln Gln
145                 150                 155                 160

Asp Pro Arg Leu Tyr Trp Gln Gly Gly Pro Ala Leu Gly Arg Ser Phe
                165                 170                 175

Leu His Gly Pro Glu Leu Asp Lys Gly Gln Leu Arg Ile His Arg Asp
            180                 185                 190

Gly Ile Tyr Met Val His Ile Gln Val Thr Leu Ala Ile Cys Ser Ser
        195                 200                 205

Thr Thr Ala Ser Arg His His Pro Thr Thr Leu Ala Val Gly Ile Cys
    210                 215                 220

Ser Pro Ala Ser Arg Ser Ile Ser Leu Leu Arg Leu Ser Phe His Gln
225                 230                 235                 240

Gly Cys Thr Ile Ala Ser Gln Arg Leu Thr Pro Leu Ala Arg Gly Asp
                245                 250                 255

Thr Leu Cys Thr Asn Leu Thr Gly Thr Leu Leu Pro Ser Arg Asn Thr
            260                 265                 270

Asp Glu Thr Phe Phe Gly Val Gln Trp Val Arg Pro Gly Ser Gly Ser
        275                 280                 285

Gly Asn Gly Ser Asp Val Ala Glu Leu Gln Leu Asp His Thr Gly Pro
    290                 295                 300

Gln Gln Asp Pro Arg Leu Tyr Trp Gln Gly Gly Pro Ala Leu Gly Arg
305                 310                 315                 320

Ser Phe Leu His Gly Pro Glu Leu Asp Lys Gly Gln Leu Arg Ile His
                325                 330                 335

Arg Asp Gly Ile Tyr Met Val His Ile Gln Val Thr Leu Ala Ile Cys
            340                 345                 350

Ser Ser Thr Thr Ala Ser Arg His His Pro Thr Thr Leu Ala Val Gly
        355                 360                 365

Ile Cys Ser Pro Ala Ser Arg Ser Ile Ser Leu Leu Arg Leu Ser Phe
    370                 375                 380

His Gln Gly Cys Thr Ile Ala Ser Gln Arg Leu Thr Pro Leu Ala Arg
385                 390                 395                 400

Gly Asp Thr Leu Cys Thr Asn Leu Thr Gly Thr Leu Leu Pro Ser Arg
                405                 410                 415
```

Asn Thr Asp Glu Thr Phe Phe Gly Val Gln Trp Val Arg Pro
                420                 425                 430

<210> SEQ ID NO 42
<211> LENGTH: 426
<212> TYPE: PRT
<213> ORGANISM: Artificial Sequence
<220> FEATURE:
<223> OTHER INFORMATION: exemplary scCD27L-RBD module

<400> SEQUENCE: 42

Asp Val Ala Glu Leu Gln Leu Asp His Thr Gly Pro Gln Gln Asp Pro
1               5                   10                  15

Arg Leu Tyr Trp Gln Gly Gly Pro Ala Leu Gly Arg Ser Phe Leu His
            20                  25                  30

Gly Pro Glu Leu Asp Lys Gly Gln Leu Arg Ile His Ar

```
Ala Ser Arg His His Pro Thr Thr Leu Ala Val Gly Ile Cys Ser Pro
        355                 360                 365
Ala Ser Arg Ser Ile Ser Leu Leu Arg Leu Ser Phe His Gln Gly Cys
    370                 375                 380
Thr Ile Ala Ser Gln Arg Leu Thr Pro Leu Ala Arg Gly Asp Thr Leu
385                 390                 395                 400
Cys Thr Asn Leu Thr Gly Thr Leu Leu Pro Ser Arg Asn Thr Asp Glu
            405                 410                 415
Thr Phe Phe Gly Val Gln Trp Val Arg Pro
            420                 425

<210> SEQ ID NO 43
<211> LENGTH: 680
<212> TYPE: PRT
<213> ORGANISM: Artificial Sequence
<220> FEATURE:
<223> OTHER INFORMATION: SEQ40+SEQ16+SEQ13

<400> SEQUENCE: 43

Glu Ser Leu Gly Trp Asp Val Ala Glu Leu Gln Leu Asp His Thr Gly
1               5                   10                  15
Pro Gln Gln Asp Pro Arg Leu Tyr Trp Gln Gly Gly Pro Ala Leu Gly
            20                  25                  30
Arg Ser Phe Leu His Gly Pro Glu Leu Asp Lys Gly Gln Leu Arg Ile
        35                  40                  45
His Arg Asp Gly Ile Tyr Met Val His Ile Gln Val Thr Leu Ala Ile
    50                  55                  60
Cys Ser Ser Thr Thr Ala Ser Arg His His Pro Thr Thr Leu Ala Val
65                  70                  75                  80
Gly Ile Cys Ser Pro Ala Ser Arg Ser Ile Ser Leu Leu Arg Leu Ser
                85                  90                  95
Phe His Gln Gly Cys Thr Ile Ala Ser Gln Arg Leu Thr Pro Leu Ala
            100                 105                 110
Arg Gly Asp Thr Leu Cys Thr Asn Leu Thr Gly Thr Leu Leu Pro Ser
        115                 120                 125
Arg Asn Thr Asp Glu Thr Phe Phe Gly Val Gln Trp Val Arg Pro Gly
    130                 135                 140
Ser Gly Ser Gly Asn Gly Ser Glu Ser Leu Gly Trp Asp Val Ala Glu
145                 150                 155                 160
Leu Gln Leu Asp His Thr Gly Pro Gln Gln Asp Pro Arg Leu Tyr Trp
                165                 170                 175
Gln Gly Gly Pro Ala Leu Gly Arg Ser Phe Leu His Gly Pro Glu Leu
            180                 185                 190
Asp Lys Gly Gln Leu Arg Ile His Arg Asp Gly Ile Tyr Met Val His
        195                 200                 205
Ile Gln Val Thr Leu Ala Ile Cys Ser Ser Thr Thr Ala Ser Arg His
    210                 215                 220
His Pro Thr Thr Leu Ala Val Gly Ile Cys Ser Pro Ala Ser Arg Ser
225                 230                 235                 240
Ile Ser Leu Leu Arg Leu Ser Phe His Gln Gly Cys Thr Ile Ala Ser
                245                 250                 255
Gln Arg Leu Thr Pro Leu Ala Arg Gly Asp Thr Leu Cys Thr Asn Leu
            260                 265                 270
Thr Gly Thr Leu Leu Pro Ser Arg Asn Thr Asp Glu Thr Phe Phe Gly
        275                 280                 285
```

```
Val Gln Trp Val Arg Pro Gly Ser Gly Ser Glu Ser Leu Gly Trp Asp
    290                 295                 300

Val Ala Glu Leu Gln Leu Asp His Thr Gly Pro Gln Gln Asp Pro Arg
305                 310                 315                 320

Leu Tyr Trp Gln Gly Gly Pro Ala Leu Gly Arg Ser Phe Leu His Gly
                    325                 330                 335

Pro Glu Leu Asp Lys Gly Gln Leu Arg Ile His Arg Asp Gly Ile Tyr
                340                 345                 350

Met Val His Ile Gln Val Thr Leu Ala Ile Cys Ser Ser Thr Thr Ala
            355                 360                 365

Ser Arg His His Pro Thr Thr Leu Ala Val Gly Ile Cys Ser Pro Ala
    370                 375                 380

Ser Arg Ser Ile Ser Leu Leu Arg Leu Ser Phe His Gln Gly Cys Thr
385                 390                 395                 400

Ile Ala Ser Gln Arg Leu Thr Pro Leu Ala Arg Gly Asp Thr Leu Cys
                405                 410                 415

Thr Asn Leu Thr Gly Thr Leu Leu Pro Ser Arg Asn Thr Asp Glu Thr
                420                 425                 430

Phe Phe Gly Val Gln Trp Val Arg Pro Gly Ser Ser Ser Ser Ser Ser
            435                 440                 445

Ser Ser Gly Ser Cys Asp Lys Thr His Thr Cys Pro Pro Cys Pro Ala
    450                 455                 460

Pro Glu Leu Leu Gly Gly Pro Ser Val Phe Leu Phe Pro Pro Lys Pro
465                 470                 475                 480

Lys Asp Thr Leu Met Ile Ser Arg Thr Pro Glu Val Thr Cys Val Val
                485                 490                 495

Val Asp Val Ser His Glu Asp Pro Glu Val Lys Phe Asn Trp Tyr Val
            500                 505                 510

Asp Gly Val Glu Val His Asn Ala Lys Thr Lys Pro Arg Glu Glu Gln
        515                 520                 525

Tyr Ser Ser Thr Tyr Arg Val Val Ser Val Leu Thr Val Leu His Gln
    530                 535                 540

Asp Trp Leu Asn Gly Lys Glu Tyr Lys Cys Lys Val Ser Asn Lys Ala
545                 550                 555                 560

Leu Pro Ala Pro Ile Glu Lys Thr Ile Ser Lys Ala Lys Gly Gln Pro
                565                 570                 575

Arg Glu Pro Gln Val Tyr Thr Leu Pro Pro Ser Arg Glu Glu Met Thr
            580                 585                 590

Lys Asn Gln Val Ser Leu Thr Cys Leu Val Lys Gly Phe Tyr Pro Ser
        595                 600                 605

Asp Ile Ala Val Glu Trp Glu Ser Asn Gly Gln Pro Glu Asn Asn Tyr
    610                 615                 620

Lys Thr Thr Pro Pro Val Leu Asp Ser Asp Gly Ser Phe Phe Leu Tyr
625                 630                 635                 640

Ser Lys Leu Thr Val Asp Lys Ser Arg Trp Gln Gln Gly Asn Val Phe
                645                 650                 655

Ser Cys Ser Val Met His Glu Ala Leu His Asn His Tyr Thr Gln Lys
            660                 665                 670

Ser Leu Ser Leu Ser Pro Gly Lys
    675                 680

<210> SEQ ID NO 44
<211> LENGTH: 669
```

```
<212> TYPE: PRT
<213> ORGANISM: Artificial Sequence
<220> FEATURE:
<223> OTHER INFORMATION: Seq41 +Seq16 +Seq13

<400> SEQUENCE: 44

Asp Val Ala Glu Leu Gln Leu Asp His Thr Gly Pro Gln Gln Asp Pro
1               5                   10                  15

Arg Leu Tyr Trp Gln Gly Gly Pro Ala Leu Gly Arg Ser Phe Leu His
            20                  25                  30

Gly Pro Glu Leu Asp Lys Gly Gln Leu Arg Ile His Arg Asp Gly Ile
        35                  40                  45

Tyr Met Val His Ile Gln Val Thr Leu Ala Ile Cys Ser Ser Thr Thr
    50                  55                  60

Ala Ser Arg His His Pro Thr Thr Leu Ala Val Gly Ile Cys Ser Pro
65                  70                  75                  80

Ala Ser Arg Ser Ile Ser Leu Leu Arg Leu Ser Phe His Gln Gly Cys
                85                  90                  95

Thr Ile Ala Ser Gln Arg Leu Thr Pro Leu Ala Arg Gly Asp Thr Leu
            100                 105                 110

Cys Thr Asn Leu Thr Gly Thr Leu Leu Pro Ser Arg Asn Thr Asp Glu
        115                 120                 125

Thr Phe Phe Gly Val Gln Trp Val Arg Pro Gly Ser Gly Ser Gly Asn
    130                 135                 140

Gly Ser Asp Val Ala Glu Leu Gln Leu Asp His Thr Gly Pro Gln Gln
145                 150                 155                 160

Asp Pro Arg Leu Tyr Trp Gln Gly Gly Pro Ala Leu Gly Arg Ser Phe
                165                 170                 175

Leu His Gly Pro Glu Leu Asp Lys Gly Gln Leu Arg Ile His Arg Asp
            180                 185                 190

Gly Ile Tyr Met Val His Ile Gln Val Thr Leu Ala Ile Cys Ser Ser
        195                 200                 205

Thr Thr Ala Ser Arg His His Pro Thr Thr Leu Ala Val Gly Ile Cys
    210                 215                 220

Ser Pro Ala Ser Arg Ser Ile Ser Leu Leu Arg Leu Ser Phe His Gln
225                 230                 235                 240

Gly Cys Thr Ile Ala Ser Gln Arg Leu Thr Pro Leu Ala Arg Gly Asp
                245                 250                 255

Thr Leu Cys Thr Asn Leu Thr Gly Thr Leu Leu Pro Ser Arg Asn Thr
            260                 265                 270

Asp Glu Thr Phe Phe Gly Val Gln Trp Val Arg Pro Gly Ser Gly Ser
        275                 280                 285

Gly Asn Gly Ser Asp Val Ala Glu Leu Gln Leu Asp His Thr Gly Pro
    290                 295                 300

Gln Gln Asp Pro Arg Leu Tyr Trp Gln Gly Gly Pro Ala Leu Gly Arg
305                 310                 315                 320

Ser Phe Leu His Gly Pro Glu Leu Asp Lys Gly Gln Leu Arg Ile His
                325                 330                 335

Arg Asp Gly Ile Tyr Met Val His Ile Gln Val Thr Leu Ala Ile Cys
            340                 345                 350

Ser Ser Thr Thr Ala Ser Arg His His Pro Thr Thr Leu Ala Val Gly
        355                 360                 365

Ile Cys Ser Pro Ala Ser Arg Ser Ile Ser Leu Leu Arg Leu Ser Phe
    370                 375                 380
```

```
His Gln Gly Cys Thr Ile Ala Ser Gln Arg Leu Thr Pro Leu Ala Arg
385                 390                 395                 400

Gly Asp Thr Leu Cys Thr Asn Leu Thr Gly Thr Leu Leu Pro Ser Arg
            405                 410                 415

Asn Thr Asp Glu Thr Phe Phe Gly Val Gln Trp Val Arg Pro Gly Ser
        420                 425                 430

Ser Ser Ser Ser Ser Ser Ser Gly Ser Cys Asp Lys Thr His Thr Cys
            435                 440                 445

Pro Pro Cys Pro Ala Pro Glu Leu Leu Gly Gly Pro Ser Val Phe Leu
        450                 455                 460

Phe Pro Pro Lys Pro Lys Asp Thr Leu Met Ile Ser Arg Thr Pro Glu
465                 470                 475                 480

Val Thr Cys Val Val Val Asp Val Ser His Glu Asp Pro Glu Val Lys
            485                 490                 495

Phe Asn Trp Tyr Val Asp Gly Val Glu Val His Asn Ala Lys Thr Lys
        500                 505                 510

Pro Arg Glu Glu Gln Tyr Ser Ser Thr Tyr Arg Val Val Ser Val Leu
            515                 520                 525

Thr Val Leu His Gln Asp Trp Leu Asn Gly Lys Glu Tyr Lys Cys Lys
530                 535                 540

Val Ser Asn Lys Ala Leu Pro Ala Pro Ile Glu Lys Thr Ile Ser Lys
545                 550                 555                 560

Ala Lys Gly Gln Pro Arg Glu Pro Gln Val Tyr Thr Leu Pro Pro Ser
            565                 570                 575

Arg Glu Glu Met Thr Lys Asn Gln Val Ser Leu Thr Cys Leu Val Lys
        580                 585                 590

Gly Phe Tyr Pro Ser Asp Ile Ala Val Glu Trp Glu Ser Asn Gly Gln
            595                 600                 605

Pro Glu Asn Asn Tyr Lys Thr Thr Pro Pro Val Leu Asp Ser Asp Gly
        610                 615                 620

Ser Phe Phe Leu Tyr Ser Lys Leu Thr Val Asp Lys Ser Arg Trp Gln
625                 630                 635                 640

Gln Gly Asn Val Phe Ser Cys Ser Val Met His Glu Ala Leu His Asn
            645                 650                 655

His Tyr Thr Gln Lys Ser Leu Ser Leu Ser Pro Gly Lys
            660                 665

<210> SEQ ID NO 45
<211> LENGTH: 665
<212> TYPE: PRT
<213> ORGANISM: Artificial Sequence
<220> FEATURE:
<223> OTHER INFORMATION: Seq41 + Seq16 + Seq13

<400> SEQUENCE: 45

Asp Val Ala Glu Leu Gln Leu Asp His Thr Gly Pro Gln Gln Asp Pro
1               5                   10                  15

Arg Leu Tyr Trp Gln Gly Gly Pro Ala Leu Gly Arg Ser Phe Leu His
            20                  25                  30

Gly Pro Glu Leu Asp Lys Gly Gln Leu Arg Ile His Arg Asp Gly Ile
        35                  40                  45

Tyr Met Val His Ile Gln Val Thr Leu Ala Ile Cys Ser Ser Thr Thr
    50                  55                  60

Ala Ser Arg His His Pro Thr Thr Leu Ala Val Gly Ile Cys Ser Pro
65                  70                  75                  80
```

```
Ala Ser Arg Ser Ile Ser Leu Leu Arg Leu Ser Phe His Gln Gly Cys
             85                  90                  95

Thr Ile Ala Ser Gln Arg Leu Thr Pro Leu Ala Arg Gly Asp Thr Leu
        100                 105                 110

Cys Thr Asn Leu Thr Gly Thr Leu Leu Pro Ser Arg Asn Thr Asp Glu
            115                 120                 125

Thr Phe Phe Gly Val Gln Trp Val Arg Pro Gly Ser Gly Ser Gly Asn
        130                 135                 140

Gly Ser Asp Val Ala Glu Leu Gln Leu Asp His Thr Gly Pro Gln Gln
145                 150                 155                 160

Asp Pro Arg Leu Tyr Trp Gln Gly Pro Ala Leu Gly Arg Ser Phe
                165                 170                 175

Leu His Gly Pro Glu Leu Asp Lys Gly Gln Leu Arg Ile His Arg Asp
            180                 185                 190

Gly Ile Tyr Met Val His Ile Gln Val Thr Leu Ala Ile Cys Ser Ser
        195                 200                 205

Thr Thr Ala Ser Arg His His Pro Thr Thr Leu Ala Val Gly Ile Cys
    210                 215                 220

Ser Pro Ala Ser Arg Ser Ile Ser Leu Leu Arg Leu Ser Phe His Gln
225                 230                 235                 240

Gly Cys Thr Ile Ala Ser Gln Arg Leu Thr Pro Leu Ala Arg Gly Asp
                245                 250                 255

Thr Leu Cys Thr Asn Leu Thr Gly Thr Leu Leu Pro Ser Arg Asn Thr
            260                 265                 270

Asp Glu Thr Phe Phe Gly Val Gln Trp Val Arg Pro Gly Ser Gly Ser
        275                 280                 285

Asp Val Ala Glu Leu Gln Leu Asp His Thr Gly Pro Gln Gln Asp Pro
290                 295                 300

Arg Leu Tyr Trp Gln Gly Pro Ala Leu Gly Arg Ser Phe Leu His
305                 310                 315                 320

Gly Pro Glu Leu Asp Lys Gly Gln Leu Arg Ile His Arg Asp Gly Ile
                325                 330                 335

Tyr Met Val His Ile Gln Val Thr Leu Ala Ile Cys Ser Ser Thr Thr
            340                 345                 350

Ala Ser Arg His His Pro Thr Thr Leu Ala Val Gly Ile Cys Ser Pro
        355                 360                 365

Ala Ser Arg Ser Ile Ser Leu Leu Arg Leu Ser Phe His Gln Gly Cys
        370                 375                 380

Thr Ile Ala Ser Gln Arg Leu Thr Pro Leu Ala Arg Gly Asp Thr Leu
385                 390                 395                 400

Cys Thr Asn Leu Thr Gly Thr Leu Leu Pro Ser Arg Asn Thr Asp Glu
                405                 410                 415

Thr Phe Phe Gly Val Gln Trp Val Arg Pro Gly Ser Ser Ser Ser Ser
            420                 425                 430

Ser Ser Ser Gly Ser Cys Asp Lys Thr His Thr Cys Pro Pro Cys Pro
        435                 440                 445

Ala Pro Glu Leu Leu Gly Gly Pro Ser Val Phe Leu Phe Pro Pro Lys
    450                 455                 460

Pro Lys Asp Thr Leu Met Ile Ser Arg Thr Pro Glu Val Thr Cys Val
465                 470                 475                 480

Val Val Asp Val Ser His Glu Asp Pro Glu Val Lys Phe Asn Trp Tyr
                485                 490                 495

Val Asp Gly Val Glu Val His Asn Ala Lys Thr Lys Pro Arg Glu Glu
```

```
            500                 505                 510
Gln Tyr Ser Ser Thr Tyr Arg Val Ser Val Leu Thr Val Leu His
        515                 520                 525

Gln Asp Trp Leu Asn Gly Lys Glu Tyr Lys Cys Lys Val Ser Asn Lys
        530                 535                 540

Ala Leu Pro Ala Pro Ile Glu Lys Thr Ile Ser Lys Ala Lys Gly Gln
545                 550                 555                 560

Pro Arg Glu Pro Gln Val Tyr Thr Leu Pro Pro Ser Arg Glu Glu Met
                565                 570                 575

Thr Lys Asn Gln Val Ser Leu Thr Cys Leu Val Lys Gly Phe Tyr Pro
            580                 585                 590

Ser Asp Ile Ala Val Glu Trp Glu Ser Asn Gly Gln Pro Glu Asn Asn
        595                 600                 605

Tyr Lys Thr Thr Pro Pro Val Leu Asp Ser Asp Gly Ser Phe Phe Leu
        610                 615                 620

Tyr Ser Lys Leu Thr Val Asp Lys Ser Arg Trp Gln Gln Gly Asn Val
625                 630                 635                 640

Phe Ser Cys Ser Val Met His Glu Ala Leu His Asn His Tyr Thr Gln
                645                 650                 655

Lys Ser Leu Ser Leu Ser Pro Gly Lys
            660                 665

<210> SEQ ID NO 46
<211> LENGTH: 669
<212> TYPE: PRT
<213> ORGANISM: Artificial Sequence
<220> FEATURE:
<223> OTHER INFORMATION: Seq44 with N170D mutein

<400> SEQUENCE: 46

Asp Val Ala Glu Leu Gln Leu Asp His Thr Gly Pro Gln Gln Asp Pro
1               5                   10                  15

Arg Leu Tyr Trp Gln Gly Gly Pro Ala Leu Gly Arg Ser Phe Leu His
            20                  25                  30

Gly Pro Glu Leu Asp Lys Gly Gln Leu Arg Ile His Arg Asp Gly Ile
        35                  40                  45

Tyr Met Val His Ile Gln Val Thr Leu Ala Ile Cys Ser Ser Thr Thr
    50                  55                  60

Ala Ser Arg His His Pro Thr Thr Leu Ala Val Gly Ile Cys Ser Pro
65                  70                  75                  80

Ala Ser Arg Ser Ile Ser Leu Leu Arg Leu Ser Phe His Gln Gly Cys
                85                  90                  95

Thr Ile Ala Ser Gln Arg Leu Thr Pro Leu Ala Arg Gly Asp Thr Leu
            100                 105                 110

Cys Thr Asp Leu Thr Gly Thr Leu Leu Pro Ser Arg Asn Thr Asp Glu
        115                 120                 125

Thr Phe Phe Gly Val Gln Trp Val Arg Pro Gly Ser Gly Ser Gly Asn
        130                 135                 140

Gly Ser Asp Val Ala Glu Leu Gln Leu Asp His Thr Gly Pro Gln Gln
145                 150                 155                 160

Asp Pro Arg Leu Tyr Trp Gln Gly Gly Pro Ala Leu Gly Arg Ser Phe
                165                 170                 175

Leu His Gly Pro Glu Leu Asp Lys Gly Gln Leu Arg Ile His Arg Asp
            180                 185                 190

Gly Ile Tyr Met Val His Ile Gln Val Thr Leu Ala Ile Cys Ser Ser
```

```
            195                 200                 205
Thr Thr Ala Ser Arg His His Pro Thr Thr Leu Ala Val Gly Ile Cys
210                 215                 220

Ser Pro Ala Ser Arg Ser Ile Ser Leu Leu Arg Leu Ser Phe His Gln
225                 230                 235                 240

Gly Cys Thr Ile Ala Ser Gln Arg Leu Thr Pro Leu Ala Arg Gly Asp
                    245                 250                 255

Thr Leu Cys Thr Asp Leu Thr Gly Thr Leu Pro Ser Arg Asn Thr
                260                 265                 270

Asp Glu Thr Phe Phe Gly Val Gln Trp Val Arg Pro Gly Ser Gly Ser
            275                 280                 285

Gly Asn Gly Ser Asp Val Ala Glu Leu Gln Leu Asp His Thr Gly Pro
        290                 295                 300

Gln Gln Asp Pro Arg Leu Tyr Trp Gln Gly Pro Ala Leu Gly Arg
305                 310                 315                 320

Ser Phe Leu His Gly Pro Glu Leu Asp Lys Gly Gln Leu Arg Ile His
                    325                 330                 335

Arg Asp Gly Ile Tyr Met Val His Ile Gln Val Thr Leu Ala Ile Cys
                340                 345                 350

Ser Ser Thr Thr Ala Ser Arg His His Pro Thr Thr Leu Ala Val Gly
        355                 360                 365

Ile Cys Ser Pro Ala Ser Arg Ser Ile Ser Leu Leu Arg Leu Ser Phe
370                 375                 380

His Gln Gly Cys Thr Ile Ala Ser Gln Arg Leu Thr Pro Leu Ala Arg
385                 390                 395                 400

Gly Asp Thr Leu Cys Thr Asp Leu Thr Gly Thr Leu Pro Ser Arg
                    405                 410                 415

Asn Thr Asp Glu Thr Phe Phe Gly Val Gln Trp Val Arg Pro Gly Ser
                420                 425                 430

Ser Ser Ser Ser Ser Ser Gly Ser Cys Asp Lys Thr His Thr Cys
435                 440                 445

Pro Pro Cys Pro Ala Pro Glu Leu Leu Gly Gly Pro Ser Val Phe Leu
450                 455                 460

Phe Pro Pro Lys Pro Lys Asp Thr Leu Met Ile Ser Arg Thr Pro Glu
465                 470                 475                 480

Val Thr Cys Val Val Val Asp Val Ser His Glu Asp Pro Glu Val Lys
                485                 490                 495

Phe Asn Trp Tyr Val Asp Gly Val Glu Val His Asn Ala Lys Thr Lys
                500                 505                 510

Pro Arg Glu Glu Gln Tyr Ser Ser Thr Tyr Arg Val Val Ser Val Leu
            515                 520                 525

Thr Val Leu His Gln Asp Trp Leu Asn Gly Lys Glu Tyr Lys Cys Lys
        530                 535                 540

Val Ser Asn Lys Ala Leu Pro Ala Pro Ile Glu Lys Thr Ile Ser Lys
545                 550                 555                 560

Ala Lys Gly Gln Pro Arg Glu Pro Gln Val Tyr Thr Leu Pro Pro Ser
                    565                 570                 575

Arg Glu Glu Met Thr Lys Asn Gln Val Ser Leu Thr Cys Leu Val Lys
                580                 585                 590

Gly Phe Tyr Pro Ser Asp Ile Ala Val Glu Trp Glu Ser Asn Gly Gln
            595                 600                 605

Pro Glu Asn Asn Tyr Lys Thr Thr Pro Pro Val Leu Asp Ser Asp Gly
        610                 615                 620
```

Ser Phe Leu Tyr Ser Lys Leu Thr Val Asp Lys Ser Arg Trp Gln
625                 630                 635                 640

Gln Gly Asn Val Phe Ser Cys Ser Val Met His Glu Ala Leu His Asn
                645                 650                 655

His Tyr Thr Gln Lys Ser Leu Ser Leu Ser Pro Gly Lys
            660                 665

<210> SEQ ID NO 47
<211> LENGTH: 680
<212> TYPE: PRT
<213> ORGANISM: Artificial Sequence
<220> FEATURE:
<223> OTHER INFORMATION: Seq31 without E51Q mutation in module (i)

<400> SEQUENCE: 47

Glu Ser Leu Gly Trp Asp Val Ala Glu Leu Gln Leu Asn His Thr Gly
1               5                   10                  15

Pro Gln Gln Asp Pro Arg Leu Tyr Trp Gln Gly Gly Pro Ala Leu Gly
                20                  25                  30

Arg Ser Phe Leu His Gly Pro Glu Leu Asp Lys Gly Gln Leu Arg Ile
            35                  40                  45

His Arg Asp Gly Ile Tyr Met Val His Ile Gln Val Thr Leu Ala Ile
        50                  55                  60

Cys Ser Ser Thr Thr Ala Ser Arg His His Pro Thr Thr Leu Ala Val
65                  70                  75                  80

Gly Ile Cys Ser Pro Ala Ser Arg Ser Ile Ser Leu Leu Arg Leu Ser
                85                  90                  95

Phe His Gln Gly Cys Thr Ile Ala Ser Gln Arg Leu Thr Pro Leu Ala
            100                 105                 110

Arg Gly Asp Thr Leu Cys Thr Asn Leu Thr Gly Thr Leu Leu Pro Ser
        115                 120                 125

Arg Asn Thr Asp Glu Thr Phe Phe Gly Val Gln Trp Val Arg Pro Gly
    130                 135                 140

Ser Gly Ser Gly Asn Gly Ser Glu Ser Leu Gly Trp Asp Val Ala Glu
145                 150                 155                 160

Leu Gln Leu Asn His Thr Gly Pro Gln Gln Asp Pro Arg Leu Tyr Trp
                165                 170                 175

Gln Gly Gly Pro Ala Leu Gly Arg Ser Phe Leu His Gly Pro Glu Leu
            180                 185                 190

Asp Lys Gly Gln Leu Arg Ile His Arg Asp Gly Ile Tyr Met Val His
        195                 200                 205

Ile Gln Val Thr Leu Ala Ile Cys Ser Ser Thr Thr Ala Ser Arg His
    210                 215                 220

His Pro Thr Thr Leu Ala Val Gly Ile Cys Ser Pro Ala Ser Arg Ser
225                 230                 235                 240

Ile Ser Leu Leu Arg Leu Ser Phe His Gln Gly Cys Thr Ile Ala Ser
                245                 250                 255

Gln Arg Leu Thr Pro Leu Ala Arg Gly Asp Thr Leu Cys Thr Asn Leu
            260                 265                 270

Thr Gly Thr Leu Leu Pro Ser Arg Asn Thr Asp Glu Thr Phe Phe Gly
        275                 280                 285

Val Gln Trp Val Arg Pro Gly Ser Gly Ser Glu Ser Leu Gly Trp Asp
    290                 295                 300

Val Ala Glu Leu Gln Leu Asn His Thr Gly Pro Gln Gln Asp Pro Arg
305                 310                 315                 320

-continued

```
Leu Tyr Trp Gln Gly Gly Pro Ala Leu Gly Arg Ser Phe Leu His Gly
                325                 330                 335

Pro Glu Leu Asp Lys Gly Gln Leu Arg Ile His Arg Asp Gly Ile Tyr
            340                 345                 350

Met Val His Ile Gln Val Thr Leu Ala Ile Cys Ser Thr Thr Ala
        355                 360                 365

Ser Arg His His Pro Thr Thr Leu Ala Val Gly Ile Cys Ser Pro Ala
    370                 375                 380

Ser Arg Ser Ile Ser Leu Leu Arg Leu Ser Phe His Gln Gly Cys Thr
385                 390                 395                 400

Ile Ala Ser Gln Arg Leu Thr Pro Leu Ala Arg Gly Asp Thr Leu Cys
                405                 410                 415

Thr Asn Leu Thr Gly Thr Leu Leu Pro Ser Arg Asn Thr Asp Glu Thr
            420                 425                 430

Phe Phe Gly Val Gln Trp Val Arg Pro Gly Ser Ser Ser Ser Ser
        435                 440                 445

Ser Ser Gly Ser Cys Asp Lys Thr His Thr Cys Pro Pro Cys Pro Ala
450                 455                 460

Pro Glu Leu Leu Gly Gly Pro Ser Val Phe Leu Phe Pro Pro Lys Pro
465                 470                 475                 480

Lys Asp Thr Leu Met Ile Ser Arg Thr Pro Glu Val Thr Cys Val Val
                485                 490                 495

Val Asp Val Ser His Glu Asp Pro Glu Val Lys Phe Asn Trp Tyr Val
            500                 505                 510

Asp Gly Val Glu Val His Asn Ala Lys Thr Lys Pro Arg Glu Glu Gln
        515                 520                 525

Tyr Ser Ser Thr Tyr Arg Val Val Ser Val Leu Thr Val Leu His Gln
    530                 535                 540

Asp Trp Leu Asn Gly Lys Glu Tyr Lys Cys Lys Val Ser Asn Lys Ala
545                 550                 555                 560

Leu Pro Ala Pro Ile Glu Lys Thr Ile Ser Lys Ala Lys Gly Gln Pro
                565                 570                 575

Arg Glu Pro Gln Val Tyr Thr Leu Pro Pro Ser Arg Glu Glu Met Thr
            580                 585                 590

Lys Asn Gln Val Ser Leu Thr Cys Leu Val Lys Gly Phe Tyr Pro Ser
        595                 600                 605

Asp Ile Ala Val Glu Trp Glu Ser Asn Gly Gln Pro Glu Asn Asn Tyr
    610                 615                 620

Lys Thr Thr Pro Pro Val Leu Asp Ser Asp Gly Ser Phe Phe Leu Tyr
625                 630                 635                 640

Ser Lys Leu Thr Val Asp Lys Ser Arg Trp Gln Gln Gly Asn Val Phe
                645                 650                 655

Ser Cys Ser Val Met His Glu Ala Leu His Asn His Tyr Thr Gln Lys
            660                 665                 670

Ser Leu Ser Leu Ser Pro Gly Lys
        675                 680
```

SINGLE-CHAIN CD27-RECEPTOR AGONIST PROTEINS

This application is a continuation of PCT/EP2016/075579, filed Oct. 24, 2016; which claims priority to U.S. Provisional Application No. 62/245,689, filed Oct. 23, 2015. The contents of the above applications are incorporated herein by reference in their entirety.

REFERENCE TO SEQUENCE LISTING, TABLE OR COMPUTER PROGRAM

The Sequence Listing is concurrently submitted herewith with the specification as an ASCII formatted text file via EFS-Web with a file name of Sequence_Listing.txt with a creation date of Apr. 13, 2018, and a size of 128 kilobytes. The Sequence Listing filed via EFS-Web is part of the specification and is hereby incorporated in its entirety by reference herein.

FIELD OF THE INVENTION

The present invention provides specific CD27 receptor agonist proteins comprising three soluble CD27L domains and an Fc fragment, nucleic acid molecules encoding the CD27 receptor agonist proteins, and uses thereof. The CD27 receptor agonist proteins are substantially non-aggregating and suitable for therapeutic, diagnostic and/or research applications.

BACKGROUND OF THE INVENTION

It is known that trimerization of TNF superfamily (TNFSF) cytokines is required for efficient receptor binding and activation. Trimeric complexes of TNF superfamily cytokines, however, are difficult to prepare from recombinant monomeric units.

WO 01/49866 and WO 02/09055 disclose recombinant fusion proteins comprising a TNF cytokine and a multimerization component, particularly a protein from the C1q protein family or a collectin. A disadvantage of these fusion proteins is, however, that the trimerization domain usually has a large molecular weight and/or that the trimerization is rather inefficient.

Schneider et al. (J Exp Med 187 (1989), 1205-1213) describe that trimers of TNF cytokines are stabilized by N-terminally positioned stabilization motifs. In CD95L, the stabilization of the receptor binding domain trimer is presumably caused by N-terminal amino acid domains which are located near the cytoplasmic membrane.

Shiraishi et al. (Biochem Biophys Res Commun 322 (2004), 197-202) describe that the receptor binding domain of CD95L may be stabilized by N-terminally positioned artificial α-helical coiled-coil (leucine zipper) motifs. It was found, however, that the orientation of the polypeptide chains to each other, e.g. parallel or antiparallel orientation, can hardly be predicted. Further, the optimal number of heptad-repeats in the coiled-coil zipper motif are difficult to determine. In addition, coiled-coil structures have the tendency to form macromolecular aggregates after alteration of pH and/or ionic strength.

WO 01/25277 relates to single-chain oligomeric polypeptides which bind to an extracellular ligand binding domain of a cellular receptor, wherein the polypeptide comprises at least three receptor binding sites of which at least one is capable of binding to a ligand binding domain of the cellular receptor and at least one is incapable of effectively binding to a ligand binding domain of the cellular receptor, whereby the single-chain oligomeric polypeptides are capable of binding to the receptor, but incapable of activating the receptor. For example, the monomers are derived from cytokine ligands of the TNF family, particularly from TNF-α.

WO 2005/103077 discloses single-chain fusion polypeptides comprising at least three monomers of a TNF family ligand member and at least two peptide linkers that link the monomers of the TNF ligand family members to one another. Recent experiments, however, have shown that these single-chain fusion polypeptides show undesired aggregation.

WO 2010/010051 discloses single-chain fusion polypeptides comprising three soluble TNF family cytokine domains and at least two peptide linkers. The described fusion polypeptides are substantially non-aggregating.

Recent studies have shown that the in vivo agonistic activity of the anti-CD27-mAb currently explored in the clinic is dependent on Fc-gamma-R crosslinking [He, L. Z., N. Prostak, L. J. Thomas, L. Vitale, J. Weidlick, A. Crocker, C. D. Pilsmaker, S. M. Round, A. Tutt, M. J. Glennie, H. Marsh and T. Keler (2013). "Agonist anti-human CD27 monoclonal antibody induces T cell activation and tumor immunity in human CD27-transgenic mice." J Immunol 191(8): 4174-4183]

There is a need in the art for novel CD27 receptor agonists that exhibit high biological activity independent of Fc-gamma-R based crosslinking in vivo, high stability, and allow for efficient recombinant manufacturing.

SUMMARY OF THE INVENTION

The present invention provides specific CD27 receptor agonist proteins that mimic the CD27:CD27L interaction in vivo, exhibit low proteolytic degradation and a shorter in vivo half-life as compared to agonistic monoclonal antibodies.

The CD27 receptor agonist proteins of the instant invention generally comprise: (i) a first soluble CD27L cytokine domain; (ii) a first peptide linker; (iii) a second soluble CD27L domain; (iv) a second peptide linker; (v) a third soluble CD27L domain; (vi) a third peptide linker (e.g., a hinge-linker) and (vii) an antibody Fc fragment.

In one embodiment, the antibody Fc fragment (vii) is located N terminal to the first CD27L domain (i) and/or C-terminal to the third CD27L domain (v). In another embodiment the antibody Fc fragment is located C-terminally to the third CD27L domain (v). In one embodiment, the polypeptide is substantially non-aggregating. In another embodiment, the second and/or third soluble CD27L domain is an N-terminally shortened domain which optionally comprises amino acid sequence mutations.

In one embodiment, at least one of the soluble CD27L domains, particularly at least one of the soluble CD27L domains (iii) and (v), is a soluble CD27L domain with an N-terminal sequence which starts at amino acid Glu51 or Asp56 of human CD27L and wherein Glu51 may be replaced by a neutral amino acid, e.g., Ser or Gly. In another embodiment, at least one of the soluble CD27L domains, particularly at least one of the soluble CD27L domains (iii) and (v), is a soluble CD27L domain with an N-terminal sequences selected from (a) Glu51—Asp56 and (b) (Gly/Ser)51—Glu56. In one embodiment, the soluble CD27L domain ends with amino acid Pro193 of human CD27L and/or optionally comprises one or more mutation at positions W55, N63, R83, R122, R138, R144, H123, H124, H148, N170, R179, D182, E183. In one embodiment, the soluble CD27L domains (i), (iii) and (v) comprise amino acids Glu51—Pro193 of human CD27L according to SEQ ID NO:1.

In one embodiment, at least one of the soluble CD27L domains, particularly at least the soluble CD27L domains (i), is a soluble CD27L domain with an N-terminal sequence which starts at amino acid Glu51 and wherein Glu51 may be replaced by Gln. In one embodiment, the first and second peptide linkers (ii) and (iv) independently have a length of 3-8 amino acids, particularly a length of 3, 4, 5, 6, 7, or 8 amino acids, and preferably are glycine/serine linkers, optionally comprising an asparagine residue which may be glycosylated. In one embodiment, the first and the second peptide linkers (ii) and (iv) consist of the amino acid sequence according to SEQ ID NO:2. In another embodiment, the polypeptide additionally comprises an N-terminal signal peptide domain, e.g., of SEQ ID NO: 17, which may comprise a protease cleavage site, and/or which additionally comprises a C-terminal element which may comprise and/or connect to a recognition/purification domain, e.g., a Strep-tag attached to a serine linker according to SEQ ID NO: 18.

In one embodiment, the antibody Fc fragment (vii) is fused to the soluble CD27L domain (i) and/or (v) via a hinge-linker, preferably of SEQ ID NO: 16. In another embodiment, the antibody Fc fragment (vii) consists of the amino acid sequence as shown in SEQ ID NO: 13 or 14.

In one embodiment, the single-chain fusion polypeptide of the present invention comprises the amino acid sequence selected from the group consisting of SEQ ID NO: 15, 25-35 and 43-47.

In one embodiment, the present invention provides a CD27 receptor agonist protein comprising a dimer of two single-chain fusion polypeptides each having the amino acid sequence set forth in SEQ ID NO: 27. In one embodiment, the two polypeptides are covalently linked through three interchain disulfide bonds formed between cysteine residues 457, 463, and 466 of each polypeptide.

In one embodiment, one or more of the asparagine residues at positions 149 and 300 of the mature polypeptide(s) SEQ ID NO: 27, 28, 29, 30, 34 or 35_are N-glycosylated. In another embodiment, the asparagine residues at positions 149 and 300 of the polypeptide(s) are both N-glycosylated.

In another embodiment, only the asparagine residue at position 149 of the mature polypeptides SEQ ID NO: 31, 32, 43 or 47 is glycosylated as the asparagine 300 is not present in those proteins.

In another embodiment, only the asparagine residue at position 145 of mature polypeptide SEQ ID NO: 33 is glycosylated.

In another embodiment, one or more of the asparagine residue at position 144 and 290 of mature polypeptide of SEQ ID NO: 44 or 46 are N-glycosylated.

In another embodiment, only the asparagine residue at position 144 of the mature polypeptide(s) of SEQ ID NO: 45 is N-glycosylated.

In another embodiment, the polypeptide(s) are further post-translationally modified. In another embodiment, the post-translational modification comprises the N-terminal glutamine of the E51Q mutein modified to pyroglutamate.

PROTEIN A, administered at either 1 mg/kg (Group 2) or 10 mg/kg (Group 3) is displayed versus it's corresponding vehicle control PBS (Group 1). Data are displayed as means±SEM. P-values calculated compared to the vehicle control (group 1) using the Mann Whitney test.

Figure 10:
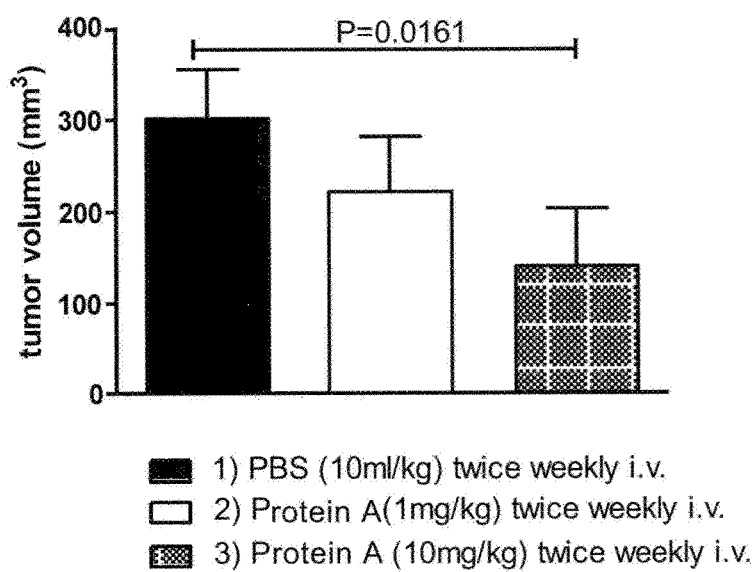

FIG. 10 Effect of PROTEIN A on subcutaneous syngeneic colon carcinoma model MC38-CEA female in female C57Bl/6N mice. Figure depicts anti-tumor efficacy (tumor volume) at necropsy. PROTEIN A, administered at either 1 mg/kg (Group 2) or 10 mg/kg (Group 3) is displayed versus it's corresponding vehicle control PBS (Group 1). Data are displayed as means±SEM. P-values calculated compared to the vehicle control (group 1) using the Mann Whitney test.

Figure 11:
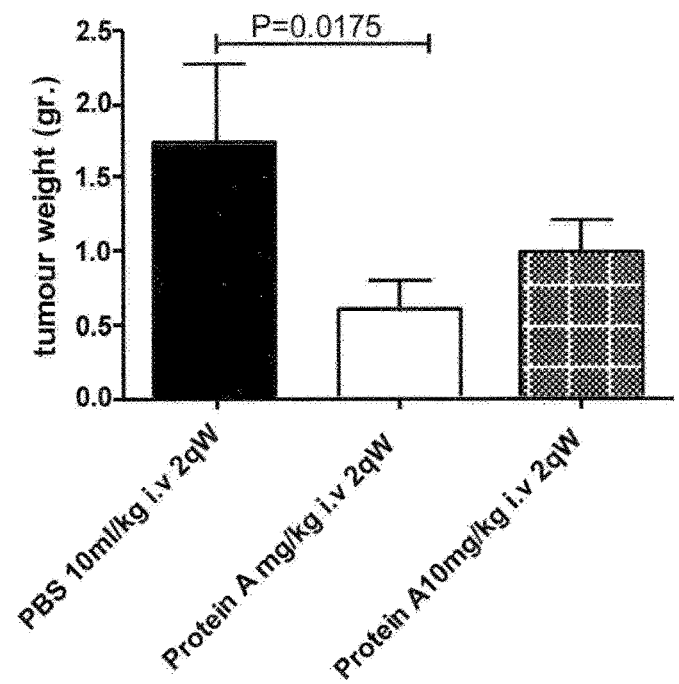

FIG. 11 Effect of PROTEIN A on subcutaneous syngeneic colon carcinoma model CT26 female in female BALB/c mice. Figure depicts wet tumor weight at necropsy (end of study). PROTEIN A, administered at either 1 mg/kg (Group 2) or 10 mg/kg (Group 3) is displayed versus it's corresponding vehicle control PBS (Group 1). Data are displayed as means±SEM. P-values calculated compared to the vehicle control (group 1) using the Mann Whitney test FIG. 12 Effect of PROTEIN A on subcutaneous syngeneic colon carcinoma model CT26 female in female BALB/c mice. Figure depicts tumor volume at the end of the study on day 21 (day 10) of. PROTEIN A, administered at either 1 mg/kg (Group 2) or 10 mg/kg (Group 3) is displayed versus it's corresponding vehicle control PBS (Group 1). Data are displayed as means±SEM. P-values calculated compared to the vehicle control (group 1) using the Mann Whitney test

DETAILED DESCRIPTION OF THE INVENTION

The present invention provides a single-chain fusion polypeptide comprising at least three soluble CD27L domains connected by two peptide linkers and N-terminally and/or C-terminally an antibody-derived dimerization domain. The inventors have discovered that dimerization of the two single-chain fusion polypeptides through the dimerization domain results in a hexavalent CD27 receptor agonist, which provides high biological activity and good stability.

Preferably, the single-chain fusion polypeptide is non-aggregating. The term "non-aggregating" refers to a monomer content of the preparation of ≥50%, preferably ≥70% and more preferably ≥90%. The ratio of monomer content to aggregate content may be determined by examining the amount of aggregate formation using size-exclusion chromatography (SEC). The stability concerning aggregation may be determined by SEC after defined time periods, e.g. from a few to several days, to weeks and months under different storage conditions, e.g. at 4° C. or 25° C. For the fusion protein, in order to be classified as substantially non-aggregating, it is preferred that the "monomer" content is as defined above after a time period of several days, e.g. 10 days, more preferably after several weeks, e.g. 2, 3 or 4 weeks, and most preferably after several months, e.g. 2 or 3 months of storage at 4° C., or 25° C. With regard to the definition of "monomer" in the case of FC-fusion proteins, the assembly of two polypeptide chains is driven by the FC-part and the functional unit of the resulting assembled protein consists of two chains. This unit is defined as "monomer" in the case of Fc-fusion proteins regardless of being a dimerized single-chain fusion polypeptide.

The single-chain fusion polypeptide may comprise additional domains which may be located at the N- and/or C-termini thereof. Examples for additional fusion domains are e.g. an N-terminal signal peptide domain which may comprise a protease cleave site or a C-terminal element which may comprise and/or connect to a recognition/purification domain. According to a preferred embodiment, the fusion polypeptide comprises a Strep-tag at its C-terminus that is fused via a linker. An exemplary Strep-tag including a short serine linker is shown in SEQ ID NO: 18.

The CD27 receptor agonist protein of the present invention comprises three soluble domains derived from CD27L. Preferably, those soluble domains are derived from a mammalian, particularly human CD27L including allelic variants and/or derivatives thereof. The soluble domains comprise the extracellular portion of CD27L including the receptor binding domain without membrane located domains. Like other proteins of the TNF superfamily, CD27L is anchored to the membrane via an N-terminal portion of 15-30 amino acids, the so-called stalk-region. The stalk region contributes to trimerization and provides a certain distance to the cell membrane. However, the stalk region is not part of the receptor binding domain (RBD).

Figure 2:
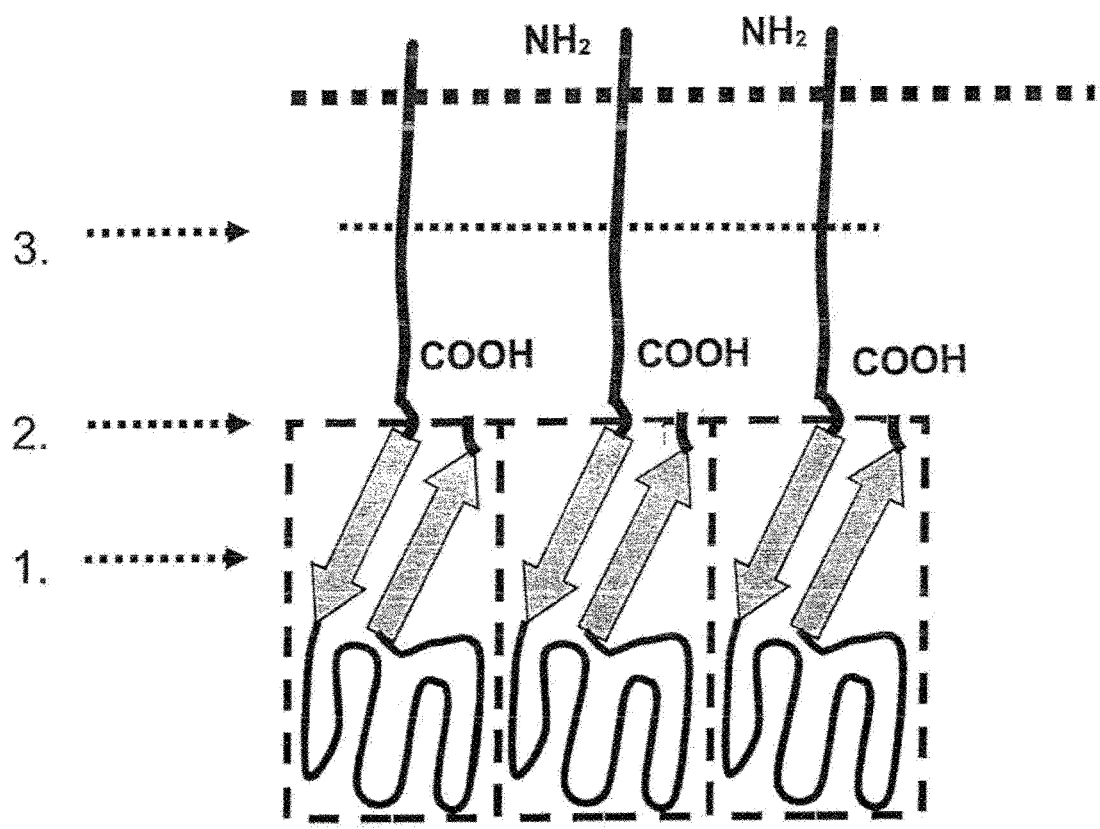
FIG. 2 Schematic picture representing the general structure of CD27L. ■ ■ ■ Cell membrane, N-terminus located within the cell, 1. anti-parallel β-fold of receptor-binding domain (RBD), 2. interface of RBD and cell membrane, 3. protease cleavage site.
Figure 3:
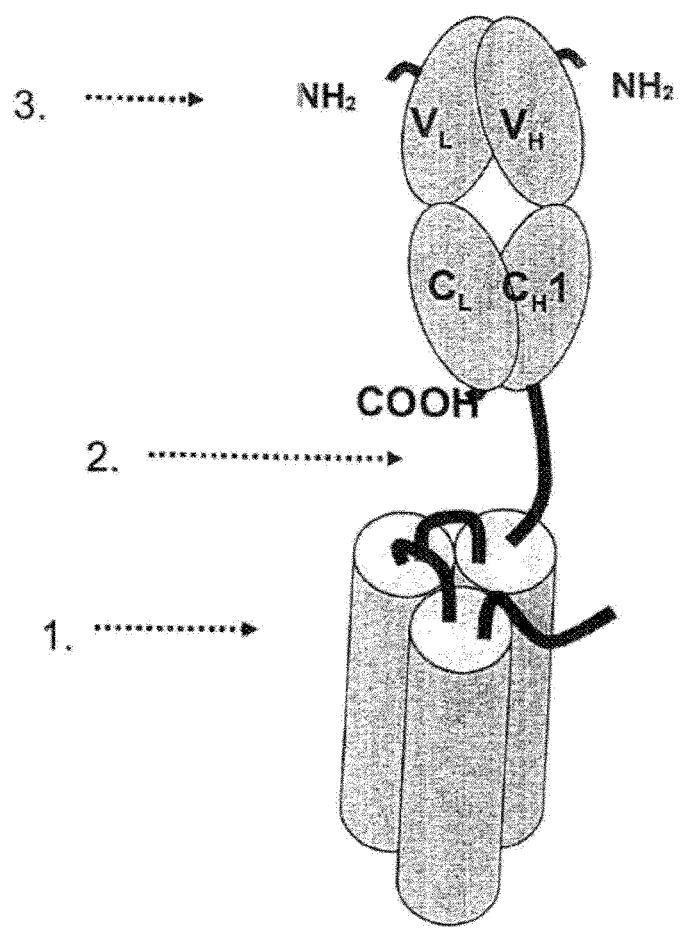
FIG. 3 Single-chain fusion polypeptide comprising an additional Fab antibody fragment.
Figure 4:
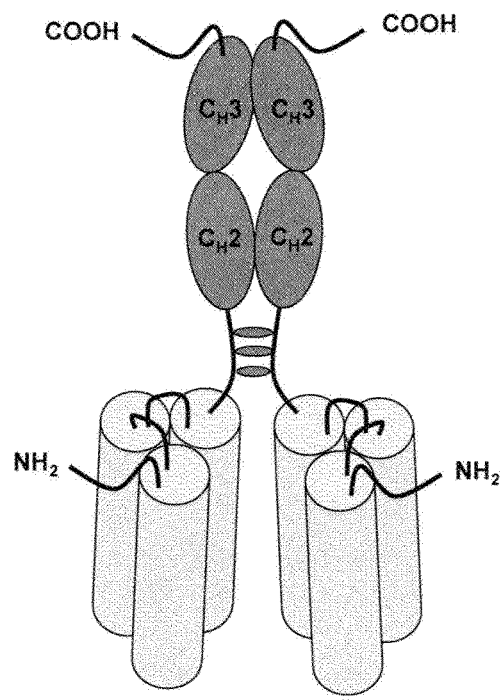
FIG. 4 Dimerization of two C-terminally fused scFc fusion polypeptides via three disulfide bridges.

Importantly, the RBD is characterized by a particular localization of its N- and C-terminal amino acids. Said amino acids are immediately adjacent and are located centrally to the axis of the trimer. The first N-terminal amino acids of the RBD form an anti-parallel beta-strand with the C-terminal amino acids of the RBD (FIG. 2).

Thus, the anti-parallel beta-strand of the RBD forms an interface with the cell membrane, which is connected to and anchored within the cell membrane via the amino acids of the stalk region. It is highly preferred that the soluble CD27L domains of the CD27 receptor agonist protein comprise a receptor binding domain of the CD27L lacking any amino acids from the stalk region. Otherwise, a long linker connecting the C-terminus of one of the soluble domains with the N-terminus of the next soluble domain would be required to compensate for the N-terminal stalk-region of the next soluble domain, which might result in instability and/or formation of aggregates.

A further advantage of such soluble domains is that the N-terminal amino acids of the RBD are not accessible for any anti-drug antibodies. Preferably, the single-chain fusion polypeptide consisting of (i) a first soluble CD27L cytokine domain; (ii) a first peptide linker; (iii) a second soluble CD27L domain; (iv) a second peptide linker; (v) a third soluble CD27L domain is capable of forming an ordered structure mimicking the trimeric organization of its natural counterpart thereby comprising at least one functional binding site for the respective CD27L receptor. The single-chain fusion polypeptide comprising components (i)-(v) is therefore also termed single-chain-CD27L-receptor-binding-domain (scCD27L-RBD).

The CD27 receptor agonist protein comprises three functional CD27 receptor binding sites, i.e. amino acid sequences capable of forming a complex with a CD27 receptor. Thus, the soluble domains are capable of binding to the corresponding CD27 receptor. In one embodiment, at least one of the soluble domains is capable of receptor activation, whereby apoptotic and/or proliferative activity may be affected. In a further embodiment, one or more of the soluble domains are selected as not being capable of receptor activation.

The soluble CD27L domain may be derived from human CD27L as shown in SEQ ID NO: 1. Preferably, the soluble CD27L domains are derived from human CD27L, particularly starting from amino acids 51 or 56 and comprise particularly amino acids 51-193 or 56-193 of SEQ ID NO:

1. Optionally, amino acid Glu51 of SEQ ID NO: 1 may be replaced by a non-charged amino acid, e.g. Ser or Gly or is replaced by Glutamine.

TABLE 1

Sequence of Wild-Type Human CD27L Protein

| SEQ ID NO | Sequence |
|---|---|
| 1 | MPEEGSGCSVRRRPYGCVLRAALVPLVAGLVICLVVCIQRFAQAQQQLPL<u>E</u><u>S</u><br>LGWDVAELQL<u>N</u>HTGPQQDPRLYWQGGPALGRSFLHGPELDKGQLRIHRDGIY<br>MVHIQVTLAICSSTTASRHHPTTLAVGICSPASRSISLLRLSFHQGCTIASQ<br>RLTPLARGDTLCT<u>N</u>LTGTLLPSRNTDETFFGVQWVRP |

As indicated above, the soluble CD27L domains may comprise the wild-type sequences as indicated in SEQ ID NO: 1. It should be noted, however, that it is possible to introduce mutations in one or more of these soluble domains, e.g. mutations which alter (e.g. increase or decrease) the binding properties of the soluble domains. In one embodiment, soluble domains that cannot bind to the corresponding cytokine receptor can be selected.

In a further embodiment of the invention, the soluble CD27L domain (i) comprises a mutant of CD27L or a receptor binding domain thereof resulting in reduced affinity and/or reduced activation of CD27 receptor.

CD27L-Muteins Affecting Receptor Binding and/or Activity

The mutant may be generated by any technique known by a skilled person. The substitution may affect at least one amino acid of CD27L, e.g., human CD27L (e.g., SEQ ID NO: 1) or a receptor binding domain thereof as described herein. Preferred substitutions in this regard affect at least one of the following amino acids of human CD27L of SEQ ID NO: 1: R83, .R122, R138, R144, H123, H124, H148, R179, D182, E183. In a preferred embodiment R138 and/or R179 are mutated to S or D.

The amino acid substitution(s) may affect the binding and/or activity of CD27L, e.g., human CD27L, to or on either the CD27 binding or the CD27 induced signaling. The binding and/or activity of the CD27 may be affected positively, i.e., stronger, more selective or more specific binding and/or more activation of the receptor. Alternatively, the binding and/or activity of the CD27 may be affected negatively, i.e., weaker, less selective or less specific binding and/or less or no activation of the receptor.

Thus one embodiment is a CD27 receptor agonist protein as described herein wherein at least one of the soluble domains comprises a mutant of CD27L or a receptor binding domain thereof which binds and/or activates CD27 to a lesser extent than the wildtype-CD27L.

Further examples of mutants of CD27L, which show reduced CD27L induced receptor aggregation/and or reduced signaling are R144N and D182S.

CD27L-Muteins with Enhanced Stability/solubility

One embodiment is a CD27 receptor agonist protein as described herein, wherein at least one artificial N-glycosylation consensus site is introduced into the sequence area defined by T172-F185 of human CD27L (SEQ ID NO:1) resulting in reduced receptor aggregation/and or reduced signaling. Examples of mutants of CD27L resulting in an artificial N-glycosylation consensus site in this region is D182S.

In a further embodiment of the invention, one or more of the soluble domains (i), (iii), and (v) may comprise a mutant of CD27L or a receptor binding domain thereof resulting in reduced self-aggregation and/or prolonged in vivo stability.

Preferred substitutions in this regard are S117N, T119N, S137N and R144N. The mutation(s) of each CD27L domain may be the same or different.

The single-chain fusion molecule of the present invention comprises three soluble CD27L domains, namely components (i), (iii) and (v). The stability of a single-chain CD27L fusion polypeptide against aggregation is enhanced, if the second and/or third soluble CD27L domain is an N-terminally shortened domain which optionally comprises amino acid sequence mutations. Thus, preferably, both the second and the third soluble CD27L domain are N-terminally shortened domains which optionally comprise amino acid sequence mutations in the N-terminal regions, preferably within the first five amino acids of the N-terminus of the soluble CD27L domain. These mutations may comprise replacement of basic amino acids, by neutral amino acids, particularly serine or glycine.

In contrast thereto, the selection of the first soluble CD27L domain is not as critical. Here, a soluble domain having a full-length N-terminal sequence may be used. It should be noted, however, that also the first soluble CD27L domain may have an N-terminally shortened and optionally mutated sequence.

In a further preferred embodiment of the present invention, the soluble CD27L domains (i), (iii) and (v) are soluble human CD27L domains. The first soluble CD27L domain (i) may be selected from native, shortened and/or mutated sequences. Thus, the first soluble CD27L domain (i) has an N-terminal sequence which may start at amino acid Glu51 or Asp56 of human CD27L, and wherein Glu51 may be replaced by a neutral amino acid, e.g. by Ser or Gly or by Gln to enable pyroglutamate formation during expression. The second and third soluble CD27L domains (iii) and (v) have a shortened N-terminal sequence which preferably starts with amino acid Ser52 or Gly54 of human CD27L (SEQ D NO:1) and wherein Glu51 may be replaced by another amino acid, e.g. Ser or Gly.

Preferably, the N-terminal sequence of the soluble CD27L domains (iii) and (v) is selected from:
(a) Glu51-Asp56
(b) (Gly/Ser)51-Asp56.

The soluble CD27L domain preferably ends with amino acid P193 of human CD27L. In certain embodiments, the CD27L domain may comprise internal mutations as described above.

Components (ii) and (iv) of the CD27 receptor agonist protein are peptide linker elements located between components (i) and (iii) or (iii) and (v), respectively. The flexible linker elements have a length of 3-8 amino acids, particularly a length of 3, 4, 5, 6, 7, or 8 amino acids. The linker elements are preferably glycine/serine linkers, i.e. peptide linkers substantially consisting of the amino acids glycine and serine. In cases in in which the soluble cytokine domain starts with S or G (N-terminus), the linker ends before this S or G.

It should be noted that linker (ii) and linker (iv) do not need to be of the same length. In order to decrease potential immunogenicity, it may be preferred to use shorter linkers. In addition it turned out that shorter linkers lead to single chain molecules with reduced tendency to form aggregates. Whereas linkers that are substantially longer than the ones disclosed here may exhibit unfavorable aggregations properties.

If desired, the linker may comprise an asparagine residue which may form a glycosylate site Asn-Xaa-Ser. In certain embodiments, one of the linkers, e.g. linker (ii) or linker (iv) comprises a glycosylation site. In other embodiments, both linkers (iv) comprise glycosylation sites. In order to increase the solubility of the CD27L agonist proteins and/or in order to reduce the potential immunogenicity, it may be preferred that linker (ii) or linker (iv) or both comprise a glycosylation site.

Preferred linker sequences are shown in Table 2. A preferred linker is GSGSGNGS (SEQ ID NO: 2).

TABLE 2

Example Linker Sequences

| SEQ ID NO | Sequence |
|---|---|
| 2 | GSGSGNGS |
| 3 | GSGSGSGS |
| 4 | GGSGSGSG |
| 5 | GGSGSG |
| 6 | GGSG |
| 7 | GGSGNGSG |
| 8 | GGNGSGSG |
| 9 | GGNGSG |
| 10 | GSGSGS |
| 11 | GSGS |
| 12 | GSG |

The CD27 receptor agonist protein additionally comprises an antibody Fc fragment domain which may be located N-terminal to the first CD27L domain (i) and/or C-terminal to the third CD27L domain (v). Preferably, the antibody Fc fragment domain comprises a reduced capability to interact with Fc-gamma-R receptors in vivo. Preferably, the antibody Fc fragment domain comprises or consists of an amino acid sequence as shown in SEQ ID NO: 13 or 14 (see Table 3). Sequence ID NO: 13 has N297S mutation compared to wildtype human IGG1-Fc and does not bind to Fc-gamma-R receptors. Sequence ID NO: 14 is a glycosylated (N297 wildtype) human IGG1 Fc mutein with reduced Fc-gamma-R binding capability.

TABLE 3

Examples of Fc Fragment Domains

| SEQ ID NO | Sequence |
|---|---|
| 13 | PAPELLGGPSVFLFPPKPKDTLMISRTPEVTCVVVDVSHEDPEVKFN WYVDGVEVHNAKTKPREEQYSSTYRVVSVLTVLHQDVVLNGKEYKCK VSNKALPAPIEKTISKAKGQPREPQVYTLPPSREEMTKNQVSLTCLVK GFYPSDIAVEWESNGQPENNYKTTPPVLDSDGSFFLYSKLTVDKSR WQQGNVFSCSVMHEALHNHYTQKSLSLSPGK |
| 14 | PAPPVAGPSVFLFPPKPKDTLMISRTPEVTCVVVDVSHEDPEVKFMN YVDGVEVHNAKTKPREEQYNSTYRVVSVLTVLHQDWLNGKEYKCKV SNKGLPSSIEKTISKAKGQPREPQVYTLPPSREEMTKNQVSLTCLVKG FYPSDIAVEWESNGQPENNYKTTPPVLDSDGSFFLYSKLTVDKSRW QQGNVFSCSVMHEALHNHYTQKSLSLSPGK |

Number of Glycosylation Sites and in Vivo Stability

The total number of glycosylation sites and the individual position of the carbohydrates in three dimensions impacts the in-vivo stability of CD27 receptor agonist proteins. Further, carbohydrate recognition depends on local density of the terminal saccharides, the branching of the carbohydrate tree and the relative position of the carbohydrates to each other matter.

Further, partially degraded carbohydrates reduce the in vivo half-life of CD27 receptor agonist proteins through lectin-driven mechanisms. By reducing the total number of glycosylation sites on the molecule, the resulting compound is less accessible to these mechanisms, increasing half-life.

Depletion of antibody CH2-domain carbohydrates is necessary in order to avoid Fc-receptor based crosslinking in vivo and potential CD27L-receptor superclustering-based toxicity. Also, unwanted Fc-driven mechanisms like ADCC could lead to toxic events. Accordingly, in one embodiment, the overall number of glycosylation sites on the CD27 receptor agonist proteins of the instant invention is reduced through the depletion of CH2 glycosylation sites, particularly the N-glycosylation site, resulting in CD27 receptor agonist proteins comprising N297S equivalent mutations of SEQ ID NO: 15 (PROTEIN A) (according to the EU numbering system) creating aglycosl-CH2 domains. In another embodiment of the invention, one or more of the soluble CD27L domains (i), (iii), and (v) may comprise a N63 and/or N170 exchanged to aspartate, serine or glycine resulting in CD27 receptor agonistic fusion proteins with a reduced number of glycosylation sites. In a preferred embodiment, the N63[D,S,G] and N170[D,S,G] mutations are restricted to the soluble CD27L domains (iii) and (v) of the agonistic CD27 receptor agonist fusion proteins of the present invention.

CH2-Domain Destabilization is Compensated by an Additional Hinge-Cysteine

Figure 6:
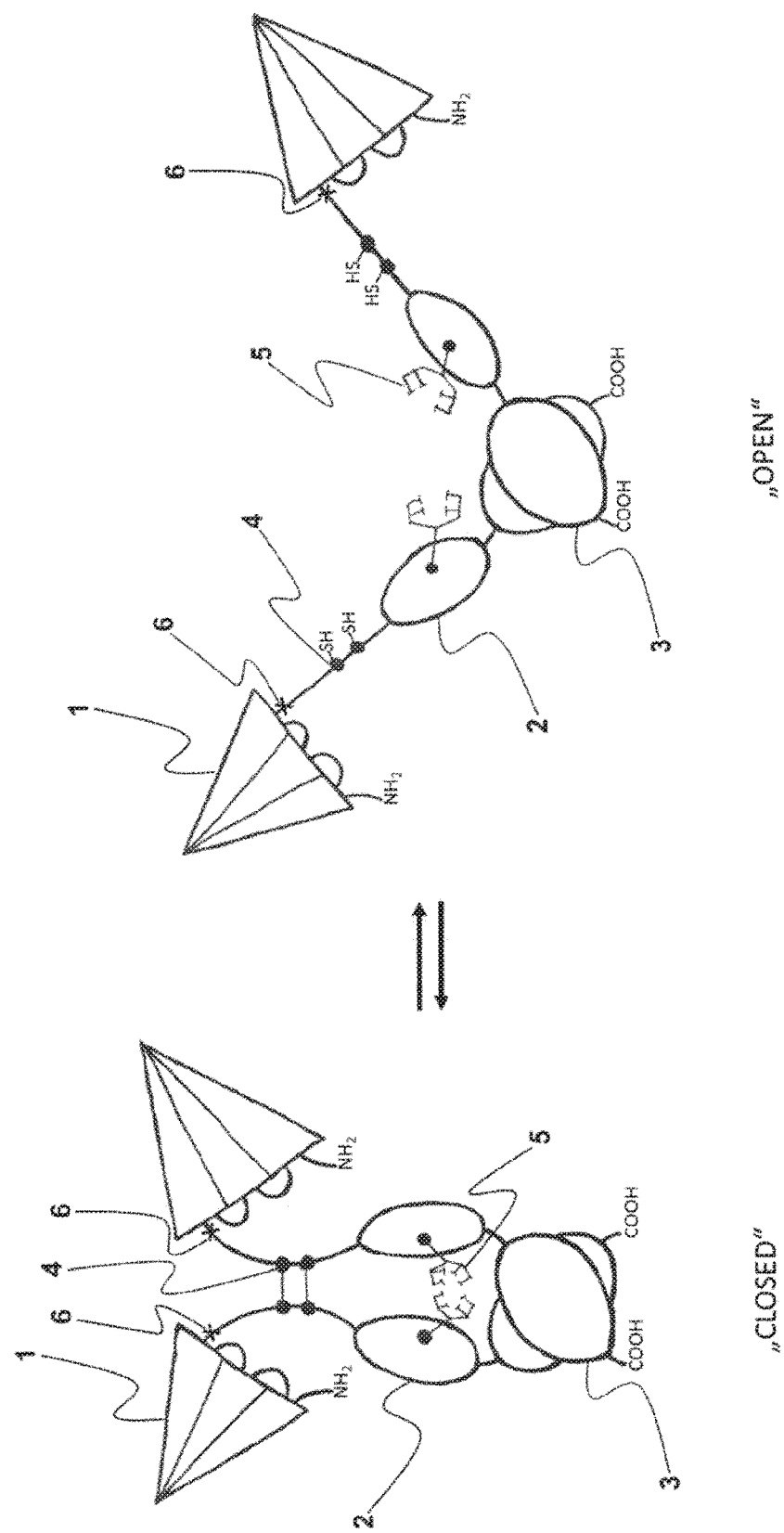
FIG. 6 Schematic representation of the hexavalent single chain CD27 receptor agonist fusion protein of the invention. CH2-Carbohydrates (5) present on the inner surface areas normally shield the CH2-subdomain sterically (2) from proteases during "open Fc-conformation transits" wherein hinge-interchain disulfide bonds (4) are reduced and the covalent interchain linkage is disrupted. This enables CH2-dissociation and exposure of the inner surface areas and the upper hinge lysine K223 (6) towards proteases. Dimer assoziation in the "open stage" remains intact due to the high affinity of the CH3 domains (3) to each other. (1) scCD27L-RBD; (2) CH2 domain; (3) CH3 domain; (4) Hinge-Cysteines (left side: oxidized to disulfidbridges; right side reduced stage with free thiols); (5) CH2-Carbohydrates attached to N297 position (EU-numbering); (6) Upper Hinge Lysine (K223)

CH2 (Heavy chain constant domain 2)-glycosylation present on the inner surface areas normally shields the subdomain from proteases during "open Fc-conformation transits" wherein hinge-interchain disulfide bonds are reduced and the covalent interchain linkage is disrupted (FIG. 6). This enables CH2-dissociation and exposure of the inner surface area towards proteases. CD27 receptor agonist proteins comprising an Fc-domain with a N297S equivalent mutation of SEQ ID NO: 15 (PROTEIN A) (according to the EU numbering system) creates an aglycosylated-CH2 and are therefore likely to be subject to protease digestion and less stable than equivalent structures with wild-type CH2 glycosylation. This would impact the compound's stability during USP/DSP/storage, where host cell proteases are present and have long-term access to the structure. Accordingly, in certain embodiments, the CD27 receptor agonist lacks CH2 glycosylation sites, but comprises glycosylation sites in the linker sequences of each polypeptide chain (e.g., GSGSGNGS, SEQ ID NO: 2).

According to a preferred embodiment of the invention, the antibody Fc fragment domain is fused via a hinge-linker element. The hinge-linker element has a length of 10-30 amino acids, particularly a length of 15-25 amino acids, e.g. 22 amino acids. The term "hinge-linker" includes any linker long enough to allow the domains attached by the hinge-linker element to attain a biologically active confirmation. The hinge-linker element preferably comprises the hinge-region sequence of an immunoglobulin, herein referred to as "Ig hinge-region". The term "Ig hinge-region" means any polypeptide comprising an amino acid sequence that shares sequence identity or similarity with a portion of a naturally occurring Ig hinge-region sequence which includes one or more cysteine residues, e.g., two cysteine residues, at which the disulfide bonds link the two heavy chains of the immunoglobulin.

Derivatives and analogues of the hinge-region can be obtained by mutations. A derivative or analogue as referred to herein is a polypeptide comprising an amino acid sequence that shares sequence identity or similarity with the full length sequence of the wild type (or naturally occurring protein) except that it has one or more amino acid sequence differences attributable to a deletion, insertion and/or substitution.

The number of molecules with open Fc-conformation in an individual CD27 receptor agonist protein depends on the number of interchain-disulfide bonds present in the hinge region. Accordingly, in one embodiment a third cysteine (C225 according to the EU numbering system) was introduced into the hinge region of the CD27 receptor agonist proteins of the instant invention in order to ameliorate the effect of depleting the CH2-glycosites.

Exchange of a Lysine to Glycine in the Hinge Region Results in Enhanced Proteolytic Stability In one embodiment, the CD27 receptor agonist proteins of the invention additionally comprise a mutation of the upper-hinge lysine (K223, according to the EU numbering system) to a glycine to reduce proteolytic processing at this site, thereby enhancing the overall stability of the fusion protein. Combining aforementioned introduction of a third cysteine (C225, according to the EU numbering system) with the aforementioned lysine to glycine mutation (K223G, according to the EU numbering system) within the hinge region results in an overall stabilized CD27 receptor agonist protein of the instant invention.

A particularly preferred hinge-linker element including the aforementioned cysteine (C225) and the lysine to glycine mutation (K223G) comprises or consists of the amino acid sequence as shown in SEQ ID NO: 16 (Table 4).

Endogenous Cysteines Interfere with Hinge-Disulfide Formation

The interchain-disulfide connectivity of the hinge region stabilizing the homodimer of the hexavalent CD27 receptor agonist protein is also affected by the free thiol groups of the CD27L subsequences. Free thiol groups can be created through reduction of surface exposed disulfide-bridges, e.g. by reduction of the C115-C151 disulfide of CD27L. This also leads to the aforementioned open FC-conformation due to self-reduction of the hinge disulfide-bridges of the structure by the endogenous free thiols of the preparation at high protein concentrations. In consequence, single-chain CD27L-FC fusion proteins comprising free thiols are expected to be less stable during manufacture and storage, when longtime exposure to oxygen and proteases occurs.

Therefore, to enable manufacture of a hexavalent CD27 receptor agonist at technical scale, the C115 and C151 residues are preferably mutated simultaneously to a different amino-acid (e.g. S, A or G).

The CD27 receptor agonist protein may additionally comprise an N-terminal signal peptide domain, which allows processing, e.g. extracellular secretion, in a suitable host cell. Preferably, the N-terminal signal peptide domain comprises a protease cleavage site, e.g. a signal peptidase cleavage site and thus may be removed after or during expression to obtain the mature protein. A particularly preferred N-terminal signal peptide domain comprises the amino acid sequence as shown in SEQ ID NO: 17 (Table 4).

Further, the CD27 receptor agonist protein may additionally comprise a C-terminal element, having a length of e.g. 1-50, preferably 10-30 amino acids which may include or connect to a recognition/purification domain, e.g. a FLAG domain, a Strep-tag or Strep-tag II domain and/or a poly-His domain. According to a preferred embodiment, the fusion polypeptide comprises a Strep-tag fused to the C-terminus via a short serine linker as shown in SEQ ID NO: 18 (Table 4).

Preferred hinge-linker elements (SEQ ID NO: 16, 19-24), a preferred N-terminal signal peptide domain (SEQ ID NO: 17) and serine linker-strep tag (SEQ ID NO: 18) are shown in Table 4.

TABLE 4

Exemplary domains and linkers

| SEQ ID NO | Sequence |
|---|---|
| 16 | GSSSSSSSSGSCDKTHTCPPC |
| 17 | METDTLLVFVLLVWVPAGNG |
| 18 | SSSSSSAWSHPQFEK |
| 19 | GSSSSSSSGSCDKTHTCPPC |
| 20 | GSSSSSGSCDKTHTCPPC |
| 21 | GSSSSSGSCDKTHTCPPC |
| 22 | GSSSGSCDKTHTCPPC |
| 23 | GSSSGSCDKTHTCPPCGS |
| 24 | GSSSGSCDKTHTCPPCGSGS |

Utilizing the hinge linkers (SEQ ID NO: 16 and 19-24) to fuse receptor binding modules of the invention to one of the preferred Fc domains (Seq ID NO: 13 and 14) allows for formation of covalently linked dimers of single chain receptor binding polypetides. Thus, one embodiment of the present invention provides a CD27 receptor agonist protein comprising a dimer of two single-chain fusion polypeptides each having the amino acid sequence set forth in SEQ ID NO: 27, wherein the two polypeptides are covalently linked through three interchain disulfide bonds formed between cysteine residues 457, 463, and 466 of each polypeptide. As non-limiting example, further polypeptide dimers of the same kind can be formed by covalently linking of cysteins at positions (457, 463 and 456) of SEQ ID Nos: 28, 29, 30 and 35.

It is obvious for a person skilled in the art that all of the non-limiting examples of CD27 receptor agonist proteins of table 5 will allow for the formation of dimers. Further embodiments of the invention are therefore covalently linked dimers of two single-chain fusion proteins. For instance dimers of SEQ ID NOs 31, 43, 47 linked at cysteine positions 453, 459 and 462, or dimers of polypeptides of SEQ ID NO: 32 (linked at positions 450, 456 and 459), or dimers of polypeptides of SEQ ID NO:33 (linked at positions 436, 442, 445), or dimers of polypeptides of SEQ ID NO:34 (linked at positions 454, 460 and 463), or dimers of polypeptides of SEQ ID NO:49 (linked at positions 438, 444 and 447), or dimers of polypeptides of SEQ ID NOs:44 or 46 (linked at positions 442, 448 and 451).

In one embodiment of the invention, the fusion polypeptide comprises three soluble CD27L domains fused by peptide linker elements of SEQ ID NO: 2. The first soluble CD27L domain (i) consists of amino acids 51-193 of human CD27L according to SEQ ID NO: 1 and the soluble CD27L domains (iii) and (v) consist of amino acids 51-193 of human CD27L according to SEQ ID NO: 1.

Preferred Configuration CD27L-Fc

Additionally, the fusion polypeptide comprises an antibody Fc fragment domain according to SEQ ID NO: 13 that is fused C-terminally to the soluble CD27L domain (v) via a hinge-linker according to SEQ ID NO: 16. The inventors surprisingly found that this particular fusion polypeptide provides improved biological activity as compared to bivalent agonistic anti-CD27-mAB and has a prolonged stability as compared to similar fusion proteins comprising a lysine in position 223 and a N2975 mutation in the CH2 domain (according to the EU numbering). The amino acid sequence of an exemplary embodiment of a CD27 receptor agonist protein of the invention is set forth in SEQ ID NO: 27.

Further, the fusion polypeptide may comprise an N-terminal signal peptide domain e.g. according to SEQ ID NO: 17. A specific example of a CD27 receptor agonist protein of the invention is shown in SEQ ID NO: 25.

According to another preferred embodiment, the fusion polypeptide may additionally comprise a C-terminal Strep-tag that is fused to the polypeptide of the invention via a short serine linker as shown in SEQ ID NO: 18. According to this aspect of the invention, the Fc fragment preferably consists of the amino acid sequence as shown in SEQ ID NO: 13 or 14. Further, the Fc fragment may consist of a shorter Fc fragment, for example including amino acids 1-217 of SEQ ID NO: 13. Particularly preferred examples of fusion polypeptides comprising a C-terminal Strep-tag are shown in SEQ ID NO: 15 (PROTEIN A).

The exemplary CD27 receptor agonist proteins as shown in SEQ ID NOs: 15, 25, and 26, each comprises an N-terminal signal peptide domain, at amino acids 1-20 of each sequence. In each case, the mature protein starts with amino acid 21. Mature exemplary CD27 receptor agonist proteins (without a signal peptide) of the instant invention are set forth in SEQ ID NO: 27-35 and 43-46. Exemplary CD27 receptor agonist proteins described above are shown in Table 5.

According to one embodiment of the invention, the single-chain CD27L fusion polypeptide domain comprises three soluble CD27L domains fused by peptide linker elements of SEQ ID NO: 2. The soluble CD27L domains (i), (iii) and (v) each consists of amino acids 51-193 of human CD27L according to SEQ ID NO: 1 optionally with the soluble domain (i) comprising the E51Q mutation. The single-chain-CD27L polypeptide comprising aforementioned CD27L E51Q mutein in domain (i) is shown in SEQ ID: 36 (Table 5B), which is well suited to generate fusion proteins with additional domains fused to either N-or C-terminal end with enhanced stability compared to wild type.

According to another embodiment of the invention, the single-chain CD27L fusion polypeptide domain comprises three soluble CD27L domains fused by peptide linker elements of SEQ ID NO: 2. The soluble CD27L domains (i), (iii) and (v) each consists of amino acids 51-193 of human CD27L according to SEQ ID NO: 1 optionally with the soluble domain (i), (iii) and (v) comprising the N63D and/or N170D mutation. Exemplarily, a single-chain-CD27L polypeptide comprising aforementioned CD27L N63D mutation in domain (i), (ii) and (v) is shown in SEQ ID: 39 (Table 5B). In a preferred embodiment, the linker (iv) of SEQ ID: 39 is exchanged to SEQ ID NO: 11 resulting in SEQ ID: 40 (Table 5B).

According to still another embodiment of the invention, the single-chain CD27L fusion polypeptide domain comprises three soluble CD27L domains fused by peptide linker elements of SEQ ID NO: 2. The soluble CD27L domains (i), (iii) and (v) each consists of amino acids 56-193 of human CD27L according to SEQ ID NO: 1 optionally with the soluble domain (i), (iii) and (v) comprising the N63D and/or N170D mutation.

Exemplarily, a single-chain-CD27L polypeptide a comprising aforementioned CD27L N63D mutation in domain (i), (ii) and (v) is shown in SEQ ID: 41 (Table 5B).). In a preferred embodiment, the linker (iv) of SEQ ID: 41 is exchanged to SEQ ID NO: 11 resulting in SEQ ID: 42 (Table 5B).

In a preferred embodiment, an antibody Fc fragment domain according to SEQ ID NO: 13 is fused C-terminally to the soluble CD27L domain (v) of SEQ ID:36 via a hinge linker according to SEQ ID NO:16 16. A specific example of a CD27 receptor agonist protein of the invention comprising the E51Q mutein in domain (i), the hinge linker of SEQ ID NO: 16 and an antibody Fc fragment according to SEQ ID NO: 13 is shown in SEQ ID NO:30 (Table 5):

The CD27 receptor agonist as set forth in SEQ ID NO: 27 27 has a reduced total number of glycosylation sites (the N297S mutation in the CH2 region providing an aglycosylated CH2 domain, according to the EU numbering system), an increased number of inter-chain disulfide bonds in the hinge region, and the mutation of an upper-hinge lysine to a glycine (K223G, according to the EU numbering system). These alterations provide a decrease in potential degradation and CD27L receptor superclustering (along with concomitant toxicity).

The CD27 receptor agonist as set forth in SEQ ID NO: 47 comprises the same layout as SEQ ID NO: 27 but with the second peptide linker (iv) shortened thereby reducing protomer dissociation and enhancing the proteins stability towards proteases.

The CD27 receptor agonist as set forth in SEQ ID NO: 30 comprises the same layout as SEQ ID NO: 27 but with the E51Q mutation in the soluble CD27L domains (i) thereby enabling formation of pyroglutamate leading to protection of the N-terminus against aminopeptidases and subsequently enhancing the overall stability of the protein during manufacture and storage. The CD27 receptor agonist as set forth in SEQ ID NO: 31 comprises the same layout as SEQ ID NO: 30 but with the second peptide linker (iv) shortened, thereby reducing protomer dissociation and enhancing the proteins stability towards proteases. The CD27 receptor agonist as set forth in SEQ ID NO: 32 comprises the same layout as SEQ ID NO: 31 but with the third peptide linker (vi) shortened to reduce the interdomain distance between the soluble CD27L domain (v) and the Fc-domain (Vii) thereby enhancing the proteins stability towards proteases. The CD27 receptor agonist as set forth in SEQ ID NO: 33 comprises:(i) a first soluble CD27L cytokine domain comprising amino acids 55-193 from SEQ ID NO: 1 with the W55Q mutation; (ii) a first peptide linker being SEQ ID NO: 2; (iii) a second soluble CD27L domain comprising amino acids 55-193 from SEQ ID NO: 1; (iv) a second peptide linker with SEQ ID NO: 11; (v) a third soluble CD27L domain comprising amino acids 55-193 from SEQ ID NO: 1; (vi) a third peptide linker with SEQ ID NO: 21 and (vii) an antibody Fc fragment with SEQ ID NO: 13. The CD27 receptor agonist as set forth in SEQ ID NO: 34 comprises the same layout as SEQ ID NO: 30 but but with the third peptide linker (vi) shortened to reduce the interdomain distance between the soluble CD27L domain (v) and the Fc-domain (vii) thereby enhancing the proteins stability towards proteases.

The CD27 receptor agonist as set forth in SEQ ID NO: 35 comprises the same layout as SEQ ID NO: 27 but with the N63D mutation in the soluble CD27L domains (i), (iii) and (v) in order to reduce the total number of N-linked carbohydrates on the proteins surface thereby reducing carbohydrate driven in vivo elimination of the compound. The CD27 receptor agonists as set forth in SEQ ID NO: 43 combines the N63D mutation strategy presented in SEQ ID 35 with a shorter linker (iv). As the shorter linker (SEQ ID 11) lacks a glycosylation consensus sequence, the total number of N-linked carbohydrates is further reduced. Additional specific CD27 receptor agonist fusion proteins of the invention with a reduced number of N-linked carbohydrates based on the N63D mutation and are set forth in SEQ ID NO: 44 and SEQ ID NO: 45 (table 5). In SEQ ID 46, each of the soluble CD27L domains (i), (iii) and (v) comprise the N63D and the N170D mutation depleting further N-linked carbohydrates from CD27 receptor agonist fusion protein

TABLE 5

Exemplary CD27 receptor agonist Proteins

| SEQ ID NO | Sequence |
|---|---|
| 25<br>PROTEIN A<br>without Strep | METDTLLVFVLLVWVPAGNGESLGWDVAELQLNHTGPQQDPRLYWQGGPALGRSFLHG<br>PELDKGQLRIHRDGIYMVHIQVTLAICSSTTASRHHPTTLAVGICSPASRSISLLRLS<br>FHQGCTIASQRLTPLARGDTLCTNLTGTLLPSRNTDETFFGVQKVRPGSGSGNGSESL<br>GMDVAELQLNHTGPQQDPRLYWQGGPALGRSFLHGPELDKGQLRIHRDGIYMVHIQVT<br>LAICSSTTASRHHPTTLAVGICSPASRSISLLRLSFHQGCTIASQRLTPLARGDTLCT<br>NLTGTLLPSRNTDETFFGVQWVRPGSGSGNGSESLGWDVAELQINHTGPQQDPRLYWQ<br>GGPALGRSFLHGPELDKGQLRIHRDGIYMVHIQVTLAICSSTTASRHHPTTLAVGICS<br>PASRSISLLRLSFHQGCTIASQRLTPLARGDTLCTNLTGTLLPSRNTDETFFGVQWVR<br>PGSSSSSSSSGSCDKTHTCPPCPAPELLGGPSVFLFPPKPKDTLMISRTPEVTCVVVD<br>VSHEDPEVKFMWYVDGVEVHNAKTKPREEQYSSTYRVVSVLTVLHQDWLNGKEYKCKV<br>SNKALPAPIEKTISKAKGQPREPQVYTLPPSREEMTKNQVSLTCLVKGFYPSDIAVEW<br>ESNGQPENNYKTTPPVLDSDGSFFLYSKLTVDKSRWQQGNVFSCSVMHEALHNHYTQK<br>SLSLSPGK |
| 15<br>PROTEIN A<br>CD27L-wt<br>+SEQ13 (FC)<br>+ Signal<br>+ Strep | KETDTLLVFVLLVWVPAGNGESLGWDVAELQLKHTGPQQDPRLYWQGGPALGRSFLHG<br>PELDKGQLRIHRDGIYMVHIQVTLAICSSTTASRHHPTTLAVGICSPASRSISLLRLS<br>FHQGCTIASQRLTPLARGDTLCTNLTGTLLPSRNTDETFFGVQWVRPGSGSGNGSESL<br>GWDVAELQLNHTGPQQDPRLYWQGGPALGRSFLHGPELDKGQLRIHRDGIYMVHIQVT<br>LAICSSTTASRHHPTTLAVGICSPASRSISLLRLSFHQGCTIASQRLTPLARGDTLCT<br>NLTGTLLPSRNTDETFFGVQWVRPGSGSGNGSESLGWDVAELQLNHTGPQQDPRLYWQ<br>GGPALGRSFLHGPELDKGQLRIHRDGIYMVHIQVTLAICSSTTASRHHPTTLAVGICS<br>PASRSISLLRLSFHQGCTIASQRLTPLARGDTLCTNLTGTLLPSRNTDETFFGVQWVR<br>PGSSSSSSSSGSCDKTHTCPPCPAPELLGGPSVFLFPPKPKDTLMISRTPEVTCVVVD<br>VSHEDPEVKFNWYVDGVEVRNAKTKPREEQYSSTYRVVSVLTVLHQDWLNGKEYKCKV<br>SNKALPAPIEKTISKAKGQPREPQVYTLPPSREEMTKNQVSLTCLVKGFYPSDIAVEW<br>ESNGQPENNYKTTPPVLDSDGSFFLYSKLTVDKSRWQQGNVFSCSVMHEALHNHYTQK<br>SLSLSPGSSSSSSAWSHPQFEK |
| 26<br>CD27L-wt<br>+SEQ14 (FC) | METDTLLVFVLLVWVPAGNGESLGWDVAELQLNHTGPQQDPRLYWQGGPALGRSFLHG<br>PELDKGQLRIHRDGIYMVHIQVTLAICSSTTASRHHPTTLAVGICSPASRSISLLRLS<br>FHQGCTIASQRLTPLARGDTLCTNLTGTLLPSRNTDETFFGVQWVRPGSGSGNGSESL<br>GWDVAELQLNHTGPQQDPRLYWQGGPALGRSFLHGPELDKGQLRIHRDGIYMVHIQVT<br>LAICSSTTASRHHPTTLAVGICSPASRSISLLRLSFHQGCTIASQRLTPLARGDTLCT<br>NLTGTLLPSRNTDETFFGVQWVRPGSGSGNGSESLGWDVAELQLNHTGPQQDPRLYWQ<br>GGPALGRSFLHGPELDKGQLRIHRDGIYMVHIQVTLAICSSTTASRHHPTTLAVGICS<br>PASRSISLLRLSFHQGCTIASQRLTPLARGDTLCTNLTGTLLPSRNTDETFFGVQWVR<br>PGSSSSSSSSGSCDKTHTCPPCPAPPVAGPSVFLFPPKPKDTLMISRTPEVTCVVVDV<br>SHEDPEVKFNWYVDGVEVHNAKTKPREEQYNSTYRVVSVLTVLHQDWLNGKEYKCKVS<br>NKGLPSSIEKTISKAKGQPREPQVYTLPPSREEMTKNQVSLTCLVKGFYPSDIAVEWE<br>SNGQPENKYKTTPPVLDSDGSFFLYSKLTVDKSRWQQGNVFSCSVMHEALHNHYTQKS<br>LSLSPGK |

TABLE 5-continued

Exemplary CD27 receptor agonist Proteins

| SEQ ID NO | Sequence |
|---|---|
| 27<br>CD27L-wt<br>+SEQ13 (FC)<br>No Signal<br>No Strep<br>No Glyco | ESLGWDVAELQLNHTGPQQDPRLYWQGGPALGRSFLHGPELDKGQLRIHRDGIYMVKI<br>QVTLAICSSTTASRKHPTTLAVGICSPASRSISLLRLSFHQGCTIASQRLTPLARGDT<br>LCTNLTGTLLPSRNTDETFFGVQWVRPGSGSGNGSESLGWDVAELQLNHTGPQQDPRL<br>YWQGGPALGRSFLHGPELDKGQLRIHRDGIYMVHIQVTLAICSSTTASRHHPTTLAVG<br>ICSPASRSISLLRLSFHQGCTIASQRLTPLARGDTLCTNLTGTLLPSRNTDETFFGVQ<br>WVRPGSGSGNGSESLGWDVAELQLNHTGPQQDPRLYWQGGPALGRSFLHGPELDKGQL<br>RIHRDGIYMVHIQVTLAICSSTTASRHHPTTLAVGICSPASRSISLLRLSFHQGCTIA<br>SQRLTPLARGDTLCTNLTGTLLPSRNTDETFFGVQWVRPGSSSSSSSSGSCDKTHTCP<br>PCPAPELLGGPSVFLFPPKPKDTLMISRTPEVTCVWDVGIIEDPEVKFNWYVDGVEVH<br>NAKTKPREEQYSSTYRVVSVLTVLHQDWLNGKEYKCKVSNKALPAPIEKTISKAKGQP<br>REPQVYTLPPSREEMTKNQVSLTCLVKGFYPSDIAVEWESNGQPENNYKTTPPVLDSD<br>GSFFLYSKLTVDKSRWQQGNVFSCSVMHEALHNHYTQKSLSLSPGK |
| 28<br>CD27L-wt<br>+SEQ13 (FC)<br>No Signal<br>+StrepTag<br>No Glyco | ESLGWDVAELQLNHTGPQQDPRLYWQGGPALGRSFLHGPELDKGQLRIHRDGIYMVHI<br>QVTLAICSSTTASRHHPTTLAVGICSPASRSISLLRLSFHQGCTIASQRLTPLARGDT<br>LCTNLTGTLLPSRNTDETFFGVQWVRPGSGSGNGSESLGWDVAELQLNHTGPQQDPRL<br>YWQGGPALGRSFLKGPELDKGQLRIHRDGIYMVHIQVTLAICSSTTASRHHPTTLAVG<br>ICSPASRSISLLRLSFHQGCTIASQRLTPLARGDTLCTNLTGTLLPSRNTDETFFGVQ<br>WVRPGSGSGNGSESLGWDVAELQLNHTGPQQDPRLYWQGGPALGRSFLHGPELDKGQL<br>RIHRDGIYMVHIQVTLAICSSTTASRHHPTTLAVGICSPASRSISLLRLSFHQGCTIA<br>SQRLTPLARGDTLCTNLTGTLLPSRNTDETFFGVQWVRPGSSSSSSSSGSCDKTHTCP<br>PCPAPELLGGPSVFLFPPKPKDTLMISRTPEVTCVVVDVSHEDPEVKFNWYVDGVEVH<br>NAKTKPREEQYSSTYRVVSVLTVLHQDWLNGKEYKCKVSNKALPAPIEKTISKAKGQP<br>REPQVYTLPPSREEMTKNQVSLTCLVKGFYPSDIAVEWESNGQPENNYKTTPPVLDSD<br>GSFFLYSKLTVDKSRWQQGNVFSCSVHHEALHNHYTQKSLSLSPGSSSSSSAWSHPQF<br>EK |
| 29<br>CD27L-wt<br>+SEQ14 (FC)<br>No Signal<br>No strep<br>Glyco FC | ESLGWDVAELQLNHTGPQQDPRLYWQGGPALGRSFLHGPELDKGQLRIHROGIYMVHI<br>QVTLAICSSTTASRHHPTTLAVGICSPASRSISLLRLSFHQGCTIASQRLTPLARGDT<br>LCTNLTGTLLPSRNTDETFFGVQWVRPGSGSGNGSESLGWDVAELQLNHTGPQQDPRL<br>YWQGGPALGRSFLHGPELDKGQLRIHRDGIYMVHIQVTLAICSSTTASRHHPTTLAVG<br>ICSPASRSISLLRLSFHQGCTIASQRLTPLARGDTLCTNLTGTLLPSRNTDETFFGVQ<br>WVRPGSGSGNGSESLGWDVAELQLNHTGPQQDPRLYWQGGPALGRSFLHGPELDKGQL<br>RIHRDGIYMVHIQVTLAICSSTTASRHHPTTLAVGICSPASRSISLLRLSFHQGCTIA<br>SQRLTPLARGDTLCTNLTGTLLPSRNTDETFFGVQWVRPGSSSSSSSSGSCDKTHTCP<br>PCPAPPVAGPSVFLFPPKPKDTLMISRTPEVTCVVVDVSHEDPEVKFNWYVDGVEVRN<br>AKTKPREEQYNSTYRVVSVLTVLHQDWLNGKEYKCKVSNKGLPSSIEKTISKAKGQPR<br>EPQVYTLPPSREEMTKNQVSLTCLVKGFYPSDIAVEWESNGQPENNYKTTPPVLDSDG<br>SFFLYSKLTVDKSRWQQGNVFSCSVMHEALHNHYTQKSLSLSPGK |
| 30<br>Same as 27<br>with E51Q<br>in module1 | QSLGWDVAELQLnHTGPQQDPRLYWQGGPALGRSFLHGPELDKGQLRIHRDGlYMVHI<br>QVTLAICSSTTASRKHPTTLAVGICSPASRSISLLRLSFHQGCTIASQRLTPLARGDT<br>LCTnLTGTLLPSRNTDETFFGVQWVRPGSGSGNGSESLGWDVAELQLnHTGPQQDPRL<br>YWQGGPALGRSFLHGPELDKGQLRIHRDGIYMVHIQVTLAICSSTTASRHHPTTLAVG<br>ICSPASRSISLLRLSFHQGCTIASQRLTPLARGDTLCTNLTGTLLPSRNTDETFFGVQ<br>WVRPGSGSGNGSESLGWDVAELQLnHTGPQQDPRLYWQGGPALGRSFLHGPELDKGQL<br>RIHRDGIYMVHIQVTLAICSSTTASRHHPTTLAVGICSPASRSISLLRLSFHQGCTIA<br>SQRLTPLARGDTLCTnLTGTLLPSRNTDETFFGVQWVRPGSSSSSSSSGSCDKTHTCP<br>PCPAPELLGGPSVFLFPPKPKDTLMISRTPEVTCVVVDVSHEDPEVKFNWYVDGVEVH<br>NAKTKPREEQYSSTYRVVSVLTVLHQDWLNGKEYKCKVSNKALPAPIEKTISKAKGQP<br>REPQVYTLPPSREEMTKNQVSLTCLVKGFYPSDIAVEWESNGQPENNYKTTPPVLDSD<br>GSFFLYSKLTVDKSRWQQGNVFSCSVMHBALHNHYTQKSLSLSPGK |
| 31 Same as<br>30 With E51Q<br>With L1 8 mer<br>glyco L2:<br>4 mer deglyco | QSLGWDVAELQLnHTGPQQDPRLYWQGGPALGRSFLHGPELDKGQLRIHRDGIYMVHI<br>QVTLAICSSTTASRHHPTTLAVGICSPASRSISLLRLSFHQGCTIASQRLTPLARGDT<br>LCTnLTGTLLPSRNTDETFFGVQWVRPGSGSGNGSESLGWDVAELQLnHTGPQQDPRL<br>YWQGGPALGRSFLHGPELDKGQLRIHRDGIYMVHIQVTLAICSSTTASRHHPTTLAVG<br>ICSPASRSISLLRLSFHQGCTIASQRLTPLARGDTLCTnLTGTLLPSRNTDETFFGVQ<br>WVRPGSGSESLGWDVAELQLnHTGPQQDPRLYWQGGPALGRSFLHGPELDKGQLRIHR<br>DGIYMVHIQVTLAICSSTTASRHHPTTLAVGICSPASRSISLLRLSFHQGCTIASQRL<br>TPLARGDTLCTnLTGTLLPSRNTDETFFGVQWVRPGSSSSSSSSGSCDKTHTCPPCPA<br>PELLGGPSVFLFPPKPKDTLMISRTPEVTCVVVDVSHEDPEVKFNWYVDGVEVHNAKT<br>KPREEQYSSTYRVVSVLTVLHQDWLNGKEYKCKVSNKALPAPIEKTISKAKGQPREPQ<br>VYTLPPSREEMTKNQVSLTCLVKGFYPSDIAVEWESNGQPENNYKTTPPVLDSDGSFF<br>LYSKLTVDKSRWQQGNVFSCSVMHEALHNHYTQKSLSLSPGEC |
| 32<br>Same as 31,<br>shortened hinge | QSLGWDVAELQLnHTGPQQDPRLYWQGGPALGRSFLHGPELDKGQLRIHRDGIYMVHI<br>QVTLAICSSTTASRHHPTTLAVGICSPASRSISLLRLSFHQGCTIASQRLTPLARGDT<br>LCTnLTGTLLPSRNTDETFFGVQWVRPgsgsgngsESLGWDVAELQLnHTGPQQDPRL<br>YWQGGPALGRSFLHGPELDKGQLRIHRDGIYMVHIQVTLAICSSTTASRHHPTTLAVG<br>ICSPASRSISLLRLSFHQGCTIASQRLTPLARGDTLCTnLTGTLLPSRNTDETFFGVQ<br>WVRPgsgsESLGWDVAELQLnHTGPQQDPRLYWQGGPALGRSFLHGPELDKGQLRIHR<br>DGIYMVHIQVTLAICSSTTASRHHPTTLAVGICSPASRSISLLRLSFHQGCTIASQRL<br>TPLARGDTLCTnLTGTLLPSRNTDETFFGVQWVRPgssssSQSCDKTHTCPPCPAPEL<br>LGGPSVFLFPPKPKDTLMISRTPEVTCVVVDVSHEDPEVKFNWYVDGVEVHNAKTKPR<br>EEQYSSTYRVVSVLTVLHQDWLNGKEYKCKVSNKALPAPIEKTISKAKGQPREPQVYT |

TABLE 5-continued

Exemplary CD27 receptor agonist Proteins

| SEQ ID NO | Sequence |
|---|---|
| | LPPSREEMTKNQVSLTCLVKGFYPSDIAVEWESNGQPENNYKTTPPVLDSEGSFFLYS<br>KLTVDKSRWQQGNVFSCSVMHEALHNHYTQKSLSLSPGK |
| 33<br>N-terminal<br>shortened<br>modules | QDVAELQLnHTGPQQDPRLYWQGGPALGRSFLHGPELDKGQLRIHRDGIYMVH<br>IQVTLAICSSTTASRHHPTTLAVGICSPASRSISLLRLSFHQGCTIASQRLTP<br>LARGDTLCTnLTGTLLPSRNTDETFFGVQWVRPgsgsgngsDVAELQLnHTGP<br>QQDPRLYWQGGPALGRSFLHGPELDKGQLRIHRDGIYMVHIQVTLAICSSTTA<br>SRHHPTTLAVGICSPASRSISLLRLSFHQGCTIASQRLTPLARGDTLCTnLTG<br>TLLPSRNTDETFFGVQWVRPgsgsgDVAELQLnHTGPQQDPRLYWQGGPALGRS<br>FLHGPELDKGQLRIHRDGIYMVHIQVTLAICSSTTASRHHPTTLAVGICSPAS<br>RSISLLRLSFHQGCTIASQRLTPLARGDTLCTnLTGTLLPSRNTDETFFGVQW<br>VRPgssssgsCDKTHTCPPCPAPELLGGPSVFLFPPPKPKDTLMISRTPEVTC<br>VVVDVSHEDPEVKFNWYVDGVEVHNAKTKPREEQYSSTYRVVSVLTVLHQDWL<br>NGKEYKCKVSNKALPAPIEKTISKAKGQPREPQVYTLPPSREEMTKNQVSLTC<br>LVKGFYPSDIAVEWESNGQPENNYKTTPPVLDSDGSFFLYSKLTVDKSRWQQG<br>NVFSCSVMHEALHNHYTQKSLSLSPGK |
| 34 | QSLGWDVAELQLnHTGPQQDPRLYWQGGPALGRSFLHGPELDKGQLRIHRDGI<br>YMVHIQVTLAICSSTTASRHHPTTLAVGICSPASRSISLLRLSFHQGCTIASQ<br>HLTPLARGDTLCTnLTGTLLPSRNTDETFFGVQWVRPGSGSGNGSESLGWDVA<br>ELQLnHTGPQQDPRLYWQGGPALGRSFLHGPELDKGQLRIHRDGIYMVHIQVT<br>LAICSSTTASRHHPTTLAVGICSPASRSISLLRLSFHQGCTIASQRLTPLARG<br>DTLCTnLTGTLLPSRNTDETFFGVQWVRPGSGSGNGSESLGWDVAELQLnHTG<br>PQQDPRLYWQGGPALGRSFLHGPELDKGQLRIHRDGIYMVHIQVTLAICSSTT<br>ASRHHPTTLAVGICSPASRSISLLRLSFHQGCTIASQRLTPLARGDTLCTnLT<br>GTLLPSRNTDETFFGVQWVRPGSSSSSGSCDKTHTCPPCPAPELLGGPSVFLF<br>PPPKPKDTLMISRTPEVTCVVVDVSHEDPEVKFNWYVDGVEVHNAKTKPREEQY<br>SSTYRVVSVLTVLHQDWINGKEYKCKVSNKALPAPIEKTISKAKGQPREPQVY<br>TLPPSREEMTKNQVSLTCIVKGFYPSDIAVEWESNGQPENNYKTTPPVLDSDG<br>SFFLYSKLTVDKSRWQQGNVFSCSVMHEALHNHYTQKSLSLSPGK |
| 35<br>(SEQ39 + SEQ<br>16 + SEQ13) | ESLGWDVAELQLDHTGPQQDPRLYWQGGPALGRSFLHGPELDKGQLRIHRDGI<br>YMVHIQVTLAICSSTTASRHHPTTLAVGICSPASRSISLLRLSFHQGCTIASQ<br>RLTPLARGDTLCTNLTGTLLPSRNTDETFFGVQWVRPGSGSGNGSESLGWDVA<br>ELQLDHTGPQQDPRLYWQGGPALGRSFLHGPELDKGQLRIHRDGIYMVHIQVT<br>LAICSSTTASRHHPTTLAVGICSPASRSISLLRLSFHQGCTIASQRLTPLARG<br>DTLCTNLTGTLLPSRNTDETFFGVQWVRPGSGSGNGSESLGWDVAELQLDHTG<br>PQQDPRLYWQGGPALGRSFLHGPELDKGQLRIHRDGIYMVHIQVTLAICSSTT<br>ASRHHPTTLAVGICSPASRSISLLRLSFHQGCTIASQRLTPLARGDTLCTNLT<br>GTLLPSRNTDETFFGVQWVRPGSSSSSSSGSCDKTHTCPPCPAPELLGGPSV<br>FLFPPPKPKDTLMISRTPEVTCVVVDVSHEDPEVKFNWYVDGVEVHNAKTKPRE<br>EQYSSTYRVVSVLTVLHQDWLNGKEYKCKVSNKALPAPIEKTISKAKGQPREP<br>QVYTLPPSREEMTKNQVSLTCLVKGFYPSDIAVEWESKGQPENNYKTTPPVLD<br>SDGSFFLYSKLTVDKSRWQQGNVFSCSVMHEALHNHYTQKSLSLSPGK |
| 43<br>PROTEIN-C<br>(SEQ40 + SEQ<br>16 + SEQ13) | ESLGWDVAELQLDHTGPQQDPRLYWQGGPALGRSFLHGPELDKGQLRIHRDGIYMVHI<br>QVTLAICSSTTASRHHPTTLAVGICSPASRSISLLRLSFHQGCTIASQRLTPLARGDT<br>LCTNLTGTLLPSRNTDETFFGVQWVRPGSGSGNGSESLGWDVAELQLDHTGPQQDPRL<br>YWQGGPALGRSFLHGPELDKGQLRIHRDGIYMVHIQVTLAICSSTTASRHHPTTLAVG<br>ICSPASRSISLLRLSFHQGCTIASQRLTPLARGDTLCTNLTGTLLPSRNTDETFFGVQ<br>WVRPGSGSESLGWDVAELQLDHTGPQQDPRLYWQGGPALGRSFLHGPELDKGQLRIHR<br>DGIYMVHIQVTLAICSSTTASRHHPTTLAVGICSPASRSISLLRLSFHQGCTIASQRL<br>TPLARGDTLCTNLTGTLLPSRNTDETFFGVQWVRPGSSSSSSSGSCDKTHTCPPCPA<br>PELLGGPSVFLFPPPKPKDTLMISRTPEVTCVVVDVSHEDPEVKFNWYVDGVEVHMAKT<br>KPREEQYSSTYRVVSVLTVLHQDWLNGKEYKCKVSNKALPAPIEKTISKAKGQPREPQ<br>VYTLPPSREEMTKNQVSLTCLVKGFYPSDIAVEWESNGQPENNYKTTPPVLDSDGSFF<br>LYSKLTVDKSRWQQGNVFSCSVMHEALHNHYTQKSLSLSPGK |
| 44<br>(SEQ41 + SEQ16<br>+ SEQ13) | DVAELQLDHTGPQQDPRLYWQGGPALGRSFLHGPELDKGQLRIHRDGIYMVHI<br>QVTLAICSSTTASRHHPTTLAVGICSPASRSISLLRLSFHQGCTIASQRLTPL<br>ARGDTLCTNLTGTLLPSRNTDETFFGVQWVRPGSGSGNGSDVAELQLDHTGPQ<br>QDPRLYWQGGPALGRSFLHGPELDKGQLRIHRDGIYMVHIQVTLAICSSTTAS<br>RHHPTTLAVGICSPASRSISLLRLSFHQGCTIASQRLTPLARGDTLCTNLTGT<br>LLPSRNTDETFFGVQWVRPGSGSGNGSDVAELQ1DHTGPQQDPRLYWQGGPAL<br>GRSFLHGPELDKGQLRIHRDGIYMVHIQVTLAICSSTTASRHHPTTLAVGICS<br>PASRSISLLRLSFHQGCTIASQRLTPLARGDTLCTNLTGTLLPSRNTDETFFG<br>VQWVRPGSSSSSSSGSCDKTHTCPPCPAPELLGGPSVFLFPPPKPKDTLMISR<br>TPEVTCVVVDVSHEDPEVKFNWYVDGVEVHKAKTKPREEQYSSTYRVVSVLTV<br>LHQDWLNGKEYKCKVSNKALPAPIEKTISKAKGQPREPQVYTLPPSREEMTKN<br>QVSLTCLVKGFYPSDIAVEWESNGQPENNYKTTPPVLDSDGSFFLYSKLTVDK<br>SRWQQGNVFSCSVMHEALHNHYTQKSLSLSPGK |
| 45<br>(SEQ41 + SEQ16<br>+ SEQ13) | DVAELQLDHTGPQQDPRLYWQGGPALGRSFLHGPELDKGQLRIHRDGIYMVHI<br>QVTLAICSSTTASRHHPTTLAVGICSPASRSISLLRLSFHQGCTIASQRLTPL<br>ARGDTLCTNLTGTLLPSRNTDETFFGVQWVRPGSGSGNGSDVAELQLDHTGPQ<br>QDPRLYWQGGPALGRSFLHGPELDKGQLRIHRDGIYMVHIQVTLAICSSTTAS |

TABLE 5-continued

Exemplary CD27 receptor agonist Proteins

| SEQ ID NO | Sequence |
|---|---|
| | RHHPTTLAVGICSPASRSISLLRLSFHQGCTIASQRLTPLARGDTLCTNLTGT<br>LLPSRNTDETFFGVQWVRPGSGSDVAELQLDHTGPQQDPRLYWQGGPALGRSF<br>LHGPELDKGQLRIHRDGIYMVHIQVTLAICSSTTASRHHPTTLAVGICSPASR<br>SISLLRLSFHQGCTIASQRLTPLARGDTLCTNLTGTLLPSRNTDETFFGVQWV<br>RPGSSSSSSSGSCDKTHTCPPCPAPELLGGPSVFLFPPKPKDTLMISRTPEV<br>TCVVVDVSHEDPEVKFNWYVDGVEVHNAKTKPREEQYSSTYRVVSVLTVLHQD<br>WLNGKEYKCKVSNKALPAPIEKTISKAKGQPREPQVYTLPPSREEMTKNQVSL<br>TCLVKGFYPSDIAVEWESNGQPENNYKTTPPVLDSDGSFFLYSKLTVDKSRWQ<br>QGNVFSCSVMHEALHNHYTQKSLSLSPGK |
| 46<br>(SEQ44 +<br>N170D) | DVAELQLDHTGPQQDPRLYWQGGPALGRSFLHGPELDKGQLRIHRDGIYMVHI<br>QVTLAICSSTTASRHHPTTLAVGICSPASRSISLLRLSFHQGCTIASQRLTPL<br>ARGDTLCTDLTGTLLPSRNTDETFFGVQWVRPGSGSGNGSDVAELQLDHTGPQ<br>QDPRLYWQGGPALGRSFLHGPELDKGQLRIHRDGIYMVHIQVTLAICSSTTAS<br>RHHPTTLAVGICSPASRSISLLRLSFHQGCTIASQRLTPLARGDTLCTDLTGT<br>LLPSRNTDETFFGVQWVRPGSGSGNGSDVAELQLDHTGPQQDPRLYWQGGPAL<br>GRSFLHGPELDKGQLRIHRDGIYMVHIQVTLAICSSTTASRHHPTTLAVGICS<br>PASRSISLLRLSFHQGCTIASQRLTPLARGDTLCTDLTGTLLPSRNTDETFFG<br>VQWVRPGSSSSSSSSGSCDKTHTCPPCPAPELLGGPSVFLFPPKPKDTLMISR<br>TPEVTCVVVDVSHEDPEVKFNWYVDGVEVHNAKTKPREEQYSSTYRVVSVLTV<br>LHQDWLNGKEYKCKVSNKALPAPIEKTISKAKGQPREPQVYTLPPSREEMTKN<br>QVSLTCLVKGFYPSDIAVEWESNGQPENNYKTTPPVLDSDGSFFLYSKLTVDK<br>SRWQQGNVFSCSVMHEALHNHYTQKSLSLSPGK |
| 47<br>PROTEIN-B<br>(Same as SEQ31,<br>without E51Q<br>in module (i)) | ESLGWDVAELQLNHTGPQQDPRLYWQGGPALGRSFLHGPELDKGQLRIHRDGI<br>YMVHIQVTLAICSSTTASRHHPTTLAVGICSPASRSISLLRLSFHQGCTIASQ<br>RLTPLARGDTLCTNLTGTLLPSRNTDETFFGVQWVRPGSGSGNGSESLGWDVA<br>ELQLNHTGPQQDPRLYWQGGPALGRSFLHGPELDKGQLRIHRDGIYMVHIQVT<br>LAICSSTTASRHHPTTLAVGICSPASRSISLLRLSFHQGCTIASQRLTPLARG<br>DTLCTNLTGTLLPSRNTDETFFGVQWVRPGSGSESLGWDVAELQLNHTGPQQD<br>PRLYWQGGPALGRSFLHGPELDKGQLRIHRDGIYMVHIQVTLAICSSTTASRH<br>HPTTLAVGICSPASRSISLLRLSFHQGCTIASQRLTPLARGDTLCTNLTGTLL<br>PSRNTDETFFGVQWVRPGSSSSSSSGSCDKTHTCPPCPAPELLGGPSVFLFP<br>PKPKDTLMISRTPEVTCVVVDVSHEDPEVKFNWYVDGVEVHNAKTKPREEQYS<br>STYRVVSVLTVLHQDWLNGKEYKCKVSNKALPAPIEKTISKAKGQPREPQVYT<br>LPPSREEMTKNQVSLTCLVKGFYPSDIAVEWESNGQPENNYKTTPPVLDSDGS<br>FFLYSKLTVDKSRWQQGNVFSCSVMHEALHNHYTQKSLSLSPGK |

TABLE 5B

Exemplary scCD27L-RBD modules

| | |
|---|---|
| 36<br>E51Q in M1 | QSLGWDVAELQLNHTGPQQDPRLYWQGGPALGRSFLHGPELDKGQLRIHRDGIYMVHI<br>QVTLAICSSTTASRHHPTTLAVGICSPASRSISLLRLSFHQGCTIASQRLTPLARGDT<br>LCTNLTGTLLPSRNTDETFFGVQWVRPGSGSGNGSESLGWDVAELQLNHTGPQQDPRL<br>YWQGGPALGRSFLHGPELDKGQLRIHRDGIYMVHIQVTLAICSSTTASRHHPTTLAVG<br>ICSPASRSISLLRLSFHQGCTIASQRLTPLARGDTLCTNLTGTLLPSRNTDETFFGVQ<br>WVRPGSGSGNGSESLGWDVAELQLNHTGPQQDPRLYWQGGPALGRSFLHGPELDKGQL<br>RIHRDGIYMVHIQVTLAICSSTTASRHHPTTLAVGICSPASRSISLLRLSFHQGCTIA<br>SQRLTPLARGDTLCTNLTGTLLPSRNTDETFFGVQWVRFG |
| 39<br>51-193 (i),<br>(iii). (v)<br>with N63D (ii)<br>8 mer (iv)<br>8 mer | ESLGWDVAELQLDHTGPQQDPRLYWQGGPALGRSFLHGPELDKGQLRIHRDGIYMVHI<br>QVTLAICSSTTASRHHPTTLAVGICSPASRSISLLRLSFHQGCTIASQRLTPLARGDT<br>LCTNLTGTLLPSRNTDETFFGVQWVRPGSGSGNGSESLGWDVAELQLDHTGPQQDPRL<br>YWQGGPALGRSFLHGPELDKGQLRIHRDGIYMVHIQVTLAICSSTTASRHHPTTLAVG<br>ICSPASRSISLLRLSFHQGCTIASQRLTPLARGDTLCTNLTGTLLPSRNTDETFFGVQ<br>WVRPGSGSGNGSESLGWDVAELQLDHTGPQQDPRLYWQGGPALGRSFLHGPELDKGQL<br>RIHRDGIYMVHIQVTLAICSSTTASRHHPTTLAVGICSPASRSISLLRLSFHQGCTIA<br>SQRLTPLARGDTLCTNLTGTLLPSRNTDETFFGVQWVRP |
| 40<br>51-193 (i),<br>(iii), (v)<br>with N63D (ii)<br>8 mer (iv):<br>4 mer | ESLGWDVAELQLDHTGPQQDPRLYWQGGPALGRSFLHGPELDKGQLRIHRDGIYMVHI<br>QVTLAICSSTTASRHHPTTLAVGICSPASRSISLLRLSFHQGCTIASQRLTPLARGDT<br>LCTNLTGTLLPSRNTDETFFGVQWVRPGSGSGNGSESLGWDVAELQLDHTGPQQDPRL<br>YWQGGPALGRSFLHGPELDKGQLRIHRDGIYMVHIQVTLAICSSTTASRHHPTTLAVG<br>ICSPASRSISLLRLSFHQGCTIASQRLTPLARGDTLCTNLTGTLLPSRNTDETFFGVQ<br>WVRPGSGSESLGWDVAELQLDHTGPQQDPRLYWQGGPALGRSFLHGPELDKGQLRIHR<br>DGIYMVHIQVTLAICSSTTASRHHPTTLAVGICSPASRSISLLRLSFHQGCTIASQRL<br>TPLARGDTLCTNLTGTLLPSRNTDETFFGVQWVRP |

TABLE 5B-continued

Exemplary scCD27L-RBD modules

| | |
|---|---|
| 41<br>56-193 (i).<br>(iii), (v)<br>with N63D (ii)<br>8 mer (iv)L2:<br>8mer | DVAELQLDHTGPQQDPRLYWQGGPALGRSFLHGPELDKGQLRIHRDGIYMVHIQVTLA<br>ICSSTTASRHHPTTLAVGICSPASRSISLLRLSFHQGCTIASQRLTPLARGDTLCTNL<br>TGTLLPSRNTDETFFGVQWVRPGSGSGNGSDVAELQLDHTGPQQDPRLYWQGGPALGR<br>SFLHGPELDKGQLRIHRDGIYMVHIQVTLAICSSTTASRHHPTTLAVGICSPASRSIS<br>LLRLSFHQGCTIASQRLTPLARGDTLCTNLTGTLLPSRNTDETFFGVQWVRPGSGSGN<br>GSDVAELQLDHTGPQQDPRLYWQGGPALGRSFLHGPELDKGQLRIHRDGIYMVHIQVT<br>LAICSSTTASRHHPTTLAVGICSPASRSISLLRLSFHQGCTIASQRLTPLARGDTLCT<br>NLTGTLLPSRNTDETFFGVQWVRP |
| 42<br>56-193<br>(v) with N63D<br>(ii) 8 mer<br>(iv) 4mer | DVAELQLDHTGPQQDPRLYWQGGPALGRSFLHGPELDKGQLRIHRDGIYMVHIQVTLA<br>ICSSTTASRHHPTTLAVGICSPASRSISLLRLSFHQGCTIASQRLTPLARGDTLCTNL<br>TGTLLPSRNTDETFFGVQWVRPGSGSGNGSDVAELQLDHTGPQQDPRLYWQGGPALGR<br>SFLHGPELDKGQLRIHRDGIYMVHIQVTLAICSSTTASRHHPTTLAVGICSPASRSIS<br>LLRLSFHQGCTIASQRLTPLARGDTLCTNLTGTLLPSRNTDETFFGVQWVRPGSGSDV<br>AELQLDHTGPQQDPRLYWQGGPALGRSFLHGPELDKGQLRIHRDGIYMVHIQVTLAIC<br>SSTTASRHHPTTLAVGICSPASRSISLLRLSFHQGCTIASQRLTPLARGDTLCTNLTG<br>TLLPSRNTDETFFGVQWVRP |

Furthermore, it has to be noted that the scCD27L-RBD module (SEQ ID NO: 36 and 39-42) are well suited to generate fusion proteins with additional domains fused to either N- or C-terminal end employing the linkers described in Table 2 (SEQ ID NO: 2-12).

Above presented embodiments of the CD27 receptor agonist proteins of the invention either address stability influencing construction principles or aggregation resistance of soluble receptor agonist proteins of the invention or modulate receptor binding and activity of the receptor agonist proteins.

A further important property for describing suitability of a substance as an active agent in medical preparations is its pharmacokinetic profile (PK profile) Pharmacokinetics is the study of drug disposition in the body and focuses on the changes in drug plasma concentration. For any given drug and dose, the plasma concentration will vary depending on the processes of absorption, distribution and elimination. The time dependent decline of plasma drug concentration and its final elimination from the body mainly depends on biotransformation and excretion of the drug and is generally measured as in vivo half-life time (Pharmacology, 4th Edition; Elesevier 2013).

Understanding the course of events that make up the immune response against a pathogen or a tumor allows to determine advantageous PK profiles of the CD27 receptor agonist proteins of the invention. The immune response against a pathogen or indeed a tumor carrying antigens can be divided into several phases. Each phase shows a characteristic duration and events usually take place in specialized tissues. In particular, the priming phase describes early events in an immune response when lymphocytes are being presented with tumor-associated antigens in secondary lymphoid organs. In order to recognize antigens through their T cell or B cell receptor, T cells and B cells, respectively, need to form cell-cell conjugates with antigen-presenting cells (APC). In case of successful antigen-recognition, lymphocytes are also being presented with co-stimulatory molecules such as CD27L by the APC. As both presentation of antigen and co-stimulatory molecules occurs at the interface of the APC/lymphocyte conjugate, this interaction is rather short lived as the conjugate falls apart after several minutes or very few hours. Following antigen recognition and co-stimulation with molecules such as CD27L lymphocytes become activated and enter the expansion phase during which they proliferate in order to mount an immune response against the tumor.

In light of the short physical interaction of APCs and lymphocytes in secondary lymphoid organs, one could speculate that the co-stimulatory signal elicited by recombinant biologics targeting the CD27 pathway is desired to be short-lived. In fact, long exposition to co-stimulatory signals might push lymphocytes into a hyper-activated state possibly leading to systemic toxic effects. Consequently, a favorable PK profile for biologics targeting co-stimulatory pathways of the immune system would show a comparably short terminal half-life in the range of hours or possibly one day. This would be in contrast to antibodies targeting the same pathways, which usually show a terminal half-life of multiple days or even more than one week. In summary, biologics activating co-stimulatory pathways of the immune system having a half-life in the range of several hours are closer to the natural ligand in term of their temporal activity in comparison to stimulating antibodies. This could also make a positive contribution to possible toxicity effects observed during the treatment with some immune-stimulating antibodies. Thus, in a further embodiment the CD27 receptor agonist proteins of the invention have a short terminal half live such as less than 4 days, less than three days, less than two days, less than one day.

A further aspect of the present invention relates to a nucleic acid molecule encoding a CD27 receptor agonist protein as described herein. The nucleic acid molecule may be a DNA molecule, e.g. a double-stranded or single-stranded DNA molecule, or an RNA molecule. The nucleic acid molecule may encode the CD27 receptor agonist protein or a precursor thereof, e.g. a pro- or pre-proform of the CD27 receptor agonist protein which may comprise a signal sequence or other heterologous amino acid portions for secretion or purification which are preferably located at the N- and/or C-terminus of the CD27 receptor agonist protein. The heterologous amino acid portions may be linked to the first and/or second domain via a protease cleavage site, e.g. a Factor X3, thrombin or IgA protease cleavage site. A specific example of a nucleic acid sequence of the invention is shown in Table 6 as SEQ ID NO: 37. This nucleic acid molecule comprises the open reading frame encoding the fusion polypeptide of SEQ ID NO: 25.

TABLE 6

Nucleic Acid Sequence of Exemplary CD27 receptor agonist Protein

| SEQ ID NO | Sequence |
|---|---|
| 37 | AAGCTTTAGGGATAACAGGGTAATAGCCGCCACCATGGAGACTGACACCCTGCTGGTGTCG<br>TGCTGCTGGTCTGGGTGCCTGCAGGAAATGGAGAGAGCCTGGGATGGGATGTGGCCGAACTC<br>CAGCTGAACCACACAGGCCCTCAGCAAGACCCTAGGCTCTACTGGCAGGGCGGCCCTGCTCT<br>GGGAAGGAGCTTTCTGCATGGCCCTGAACTGGATAAAGGCCAACTGCGTATTCATCGGGATG<br>GCATTTACATGGTCCATATCCAGGTGACCCTCGCCATCTGCTCCAGCACCACCGGTAGCAGG<br>CATCATCCCACCACCCTGGCCGTGGGCATTTGTTCCCCTGCCAGCCGGTCCATCTCCCTGCT<br>GAGGCTGAGCTTTCATCAGGGCTGCACCATCGCCTCCCAAAGGCTGACCCCTCTGGCCAGGG<br>GCGATACACTGTGTACCAATCTGACCGGCACCCTGCTCCCTAGCAGGAACACCGATGAAACC<br>TTTTTCGGAGTGCAGTGGGTGCGGCCTGGTTCCGGAAGCGGCAATGGCTCCGAAAGCCTCGG<br>CTGGGACGTGGCCGAGCTCCAACTGAACCACACCGGCCCTCAACAAGATCCTCGGCTCTATT<br>GGCAAGGCGGACCTGCTCTCGGCCGGAGCTTCCTGCATGGCCCTGAGCTGGACAAGGGCCAG<br>CTGCGTATTCATCGGGATGGAATCTATATGGTGCACATCCAAGTGACACTGGCCATTTGCAG<br>CAGCACCACCGCTAGCCGGCACCATCCTACCACCCTGGCTGTGGGCATCTGTTCCCCCGCTA<br>GCCGGTCCATCTCCCTGCTGAGGCTGAGCTTCCACCAGGGCTGTACCATCGCCAGCCAGAGG<br>CTGACCCCTCTGGCTAGGGGCGACACCCTGTGTACCAACCTGACCGGAACCCTGCTGCCTAG<br>CAGGAATACCGATGAGACCTTCTTCGGAGTGCAATGGGTGAGGCCTGGCTCTGGTTCTGGTA<br>ACGGTTCTGAGAGCCTCGGCTGGGACGTCGCTGAACTGCAGCTGAATCACACAGGCCCCCAG<br>CAGGACCCTAGGCTGTACTGGCAGGGAGGCCCTGCTCTCGGAAGGAGCTTTCTGCACGGCCC<br>TGAACTGGATAAGGGACAGCTCCGTATTCATCGGGATGGCATCTACATGGTGCATATCCAGG<br>TCACCCTGGCCATCTGCAGCTCCACCACCGCCTCCAGGCACCACCCTACCACCCTGGCTGTG<br>GGCATCTGCTCCCCTGCCTCCCGGAGCATCAGCCTGCTGAGGCTGTCCTTCCACCAAGGCTG<br>CACCATCGCTAGCCAAAGGCTGACCCCTCTGGCTAGGGGCGATACCCTGTGCACCAACCTGA<br>CCGGAACCCTGCTGCCTTCCCGGAACACCGACGAGACCTTTTTCGGCGTGCAGTGGGTCAGG<br>CCCGGATCctcgagTTCATCGTCCTCATCCGGCTCATGTGATAAGACCCACACCTGCCCTCC<br>CTGTCCTGCCCCTGAGCTGCTGGGCGGACCTTCTGTGTTCCTGTTCCCCCCCAAGCCTAAGG<br>ACACCCTGATGATCTCCAGGACCCCTGAGGTGACCTGTGTGGTGGTGGACGTGTCTCACGAA<br>GATCCCGAGGTGAAGTTCAACTGGTACGTGGACGGCGTGGAGGTCCACAACGCCAAGACCAA<br>GCCTAGGGAGGAGCAGTACAGCTCCACCTACCGGGTGGTGTCTGTGCTGACCGTGCTGCACC |

The nucleic acid molecule may be operatively linked to an expression control sequence, e.g. an expression control sequence which allows expression of the nucleic acid molecule in a desired host cell. The nucleic acid molecule may be located on a vector, e.g. a plasmid, a bacteriophage, a viral vector, a chromosomal integration vector, etc. Examples of suitable expression control sequences and vectors are described for example by Sambrook et al. (1989) Molecular Cloning, A Laboratory Manual, Cold Spring Harbor Press, and Ausubel et al. (1989), Current Protocols in Molecular Biology, John Wiley & Sons or more recent editions thereof.

Various expression vector/host cell systems may be used to express the nucleic acid sequences encoding the CD27 receptor agonist proteins of the present invention. Suitable host cells include, but are not limited to, prokaryotic cells such as bacteria, e.g. *E.coli*, eukaryotic host cells such as yeast cells, insect cells, plant cells or animal cells, is preferably mammalian cells and, more preferably, human cells. Further, the invention relates to a non-human organism transformed or transfected with a nucleic acid molecule as described above. Such transgenic organisms may be generated by known methods of genetic transfer including homologous recombination.

A further aspect of the present invention relates to a pharmaceutical or diagnostic composition comprising as the active agent at least one CD27 receptor agonist protein, a respective nucleic acid encoding therefore, or a transformed or transfected cell, all as described herein.

In another aspect, the present invention provides a pharmaceutical composition comprising a CD27 receptor agonist protein disclosed herein and one or more pharmaceutically acceptable carriers, diluents, excipients, and/or adjuvants. In another aspect, the present invention provides a nucleic acid molecule encoding the CD27 receptor agonist protein. In another embodiment, the present invention provides an expression vector comprising the nucleic acid molecule. In another embodiment, the present invention provides a cell comprising the nucleic acid molecule. In a further embodiment, the cell is a eukaryotic cell. In another embodiment, the cell is a mammalian cell. In another embodiment, the cell is a Chinese Hamster Ovary (CHO) cell. In other embodiments, the cell is selected from the group consisting of CHO-DBX11, CHO-DG44, CHO-S, and CHO-K1 cells. In other embodiments, the cell is selected from the group consisting of Vero, BHK, HeLa, COS, MDCK, HEK-293, NIH-3T3, W138, BT483, Hs578T, HTB2, BT20, T47D, NS0, CRL7030, HsS78Bst, PER.C6, SP2/0-Ag14, and hybridoma cells.

In another aspect, the present invention provides a method of treating a subject having a CD27L-associated disease or disorder, the method comprising administering to the subject an effective amount of the CD27 receptor agonist protein. In one embodiment, the CD27 receptor agonist protein is administered alone. In another embodiment, the CD27 receptor agonist protein is administered before, concurrently, or after the administration of a second agent. In another embodiment, the disease or disorder is selected from the group consisting of: tumors, infectious diseases, inflammatory diseases, metabolic diseases, autoimmune disorders, degenerative diseases, apoptosis-associated diseases, and transplant rejections. In one embodiment, the tumors are solid tumors. In one embodiment, the tumors arise from the group of cancers consisting of sarcoma, esophageal cancer, and gastric cancer. In another embodiment, the tumors arise from Ewing's sarcoma or fibrosarcoma. In another embodiment, the tumors arise from the group of cancers consisting of Non-Small Cell Lung Carcinoma (NSCLC), pancreatic cancer, colorectal cancer, breast cancer, ovarian cancer, head and neck cancers, and Small Cell Lung Cancer (SCLC). In another embodiment, the tumors are lymphatic tumors. In one embodiment, the tumors are hematologic tumors.

In another embodiment, the tumors arise from non-Hodgkin's lymphoma, leukemia, acute lymphoblastic leukemia (ALL), acute myeloid leukemia (AML), B cell lymphoma, Burkitt's lymphoma, chronic myelocytic leukemia (CML), chronic lymphocytic leukemia (CLL), or hairy cell leukemia. In another embodiment, the autoimmune disorders are rheumatoid diseases, arthritic diseases, or rheumatoid and arthritic diseases. In a further embodiment, the disease or disorder is rheumatoid arthritis. In another embodiment, the degenerative disease is a neurodegenerative disease. In a further embodiment, the neurodegenerative disease is multiple sclerosis.

In one embodiment, the second agent is a chemotherapeutic, radiotherapeutic, or biological agent. In one embodiment, the second agent is selected from the group consisting of Duvelisib, Ibrutinib, Navitoclax, and Venetoclax. In another embodiment, the second agent is an apoptotic agent. In one embodiment, the apoptotic second agent is selected from the group consisting of Bortezomib, Azacitidine, Dasatinib, and Gefitinib. In a particular embodiment, the pharmaceutical compositions disclosed herein are administered to a patient by intravenous or subcutaneous administration. In other embodiments, the disclosed pharmaceutical compositions are administered to a patient byoral, parenteral, intramuscular, intrarticular, intrabronchial, intraabdominal, intracapsular, intracartilaginous, intracavitary, intracelial, intracerebellar, intracerebroventricular, intracolic, intracervical, intragastric, intrahepatic, intramyocardial, intraosteal, intrapelvic, intrapericardiac, intraperitoneal, intrapleural, intraprostatic, intrapulmonary, intrarectal, intrarenal, intraretinal, intraspinal, intrasynovial, intrathoracic, intrauterine, intravesical, bolus, vaginal, rectal, buccal, sublingual, intranasal, or transdermal administration.

In one embodiment, the CD27 receptor agonist protein is administered as a single bolus. In another embodiment, CD27 receptor agonist protein may be administered over several divided doses. The CD27 receptor agonist protein can be administered at about 0.1-100 mg/kg. In one embodiment, the CD27 receptor agonist protein can be administered at a dosage selected from the group consisting of: about 0.1-0.5, 0.1-1, 0.1-10, 0.1-20, 0.1-50, 0.1-75, 1-10, 1-15, 1-7.5, 1.25-15, 1.25-7.5, 2.5-7.5, 2.5-15, 5-15, 5-7.5,1-20, 1-50, 7-75, 1-100, 5-10, 5-15, 5-20, 5-25, 5-50, 5-75, 10-20, 10-50, 10-75, and 10-100 mg/kg. In other embodiments, the CD27 receptor agonist protein is present in pharmaceutical compositions at about 0.1-100 mg/ml. In one embodiment, the CD27 receptor agonist protein is present in pharmaceutical compositions at an amount selected from the group consisting of: about 0.1-0.5, 0.1-1, 0.1-10, 0.1-20, 0.1-50, 0,1-75, 1-10, 1-20, 1-50, 1-75, 1-100, 5-10, 5-15, 5-20, 5-25, 5-50, 5-75, 10-20, 10-50, 10-75, or 10-100 mg/ml. In other embodiments, a therapeutically effective amount of CD27 receptor agonist protein is administered to a subject. In another embodiment, a prophylactically effective amount of CD27 receptor agonist protein is administered to a subject.

The term "CD27L-associated disease or disorder" as used herein is any disease or disorder which may be ameliorated by administering an effective amount of a CD27 receptor agonist to a subject in need thereof. At least one CD27 receptor agonist protein, respective nucleic acid encoding therefore, or transformed or transfected cell, all as described herein may be used in therapy, e.g., in the prophylaxis and/or treatment of disorders caused by, associated with and/or accompanied by dysfunction of CD27L, particularly proliferative disorders, such as tumors, e,g. solid or lymphatic tumors; infectious diseases; inflammatory diseases; metabolic diseases; autoimmune disorders, e.g. rheumatoid and/or arthritic diseases; degenerative diseases, e.g. neurodegenerative diseases such as multiple sclerosis; apoptosis-associated diseases or transplant rejections.

The term "dysfunction of CD27L" as used herein is to be understood as any function or expression of CD27L that deviates from the normal function or expression of CD27L, e.g., overexpression of the CD27L gene or protein, reduced or abolished expression of the CD27L gene or protein compared to the normal physiological expression level of CD27L, increased activity of CD27L, reduced or abolished activity of CD27L, increased binding of CD27L to any binding partners, e.g., to a receptor, particularly a CD27L receptor or another cytokine molecule, reduced or abolished binding to any binding partner, e.g. to a receptor, particularly a CD27L receptor or another cytokine molecule, compared to the normal physiological activity or binding of CD27L.

In various embodiments, a method is provided for treating a human subject suffering from a disorder which can be treated by targeting CD27 receptors comprising administering to the human subject a CD27 receptor agonist protein disclosed herein such that the effect on the activity of the target, or targets, in the human subject is agonistic, one or more symptoms is alleviated, and/or treatment is achieved. The CD27 receptor agonist proteins provided herein can be used to treat humans suffering from primary and metastatic cancers, including carcinomas of breast, colon, rectum, lung (e.g., small cell lung cancer "SCLC" and non-small cell lung cancer "NSCLC"), oropharynx, hypopharynx, esophagus, stomach, pancreas, liver, gallbladder and bile ducts, small intestine, urinary tract (including kidney, bladder and urothelium), female genital tract (including cervix, uterus, and ovaries as well as choriocarcinoma and gestational trophoblastic disease), male genital tract (including prostate, seminal vesicles, testes and germ cell tumors), endocrine glands (including the thyroid, adrenal, and pituitary glands), and skin, as well as hemangiomas, melanomas, sarcomas (including those arising from bone and soft tissues as well as Kaposi's sarcoma), tumors of the brain, nerves, eyes, and meninges (including astrocytomas, gliomas, glioblastomas, retinoblastomas, neuromas, neuroblastomas, Schwannomas, and meningiomas), tumors arising from hematopoietic malignancies, acute leukemia, acute lymphoblastic leukemia (ALL), acute myeloid leukemia (AML), B cell lymphoma, Burkitt's lymphoma, chronic myelocytic leukemia (CML), chronic lymphocytic leukemia (CLL), hairy cell leukemia, Hodgkin's and non-Hodgkin's lymphomas, DLBCL, follicular lymphomas, hematopoietic malignancies, Kaposi's sarcoma, malignant lymphoma, malignant histiocytosis, malignant melanoma, multiple myeloma, paraneoplastic syndrome/hypercalcemia of malignancy, or solid tumors.

A pharmaceutical composition comprising a CD27 receptor agonist protein disclosed herein and a pharmaceutically acceptable carrier is provided. In some embodiments, the pharmaceutical composition comprises at least one additional therapeutic agent for treating a disorder. For example, the additional agent may be a therapeutic agent, a chemotherapeutic agent; an imaging agent, a cytotoxic agent, an angiogenesis inhibitor, a kinase inhibitor (including but not limited to a KDR and a TIE-2 inhibitor), a co-stimulation molecule modulator or an immune checkpoint inhibitor (including but not limited to anti-B7.1, anti-B7.2, anti-B7.3, anti-B7.4, anti-CD28, anti-B7RP1, CTLA4-Ig, anti-CTLA-4, anti-PD-1, anti-PD-L1, anti-PD-L2, anti-ICOS, anti-LAG-3, anti-Tim3, anti-VISTA, anti-HVEM, anti-BTLA, LIGHT fusion protein, anti-CD137, anti-CD137L, anti-OX40, anti-OX40L, anti-CD70, anti-CD27, anti-GAL9, anti-A2AR, anti-KIR, anti-IDO-1, anti-CD20), a dendritic cell/antigen-presenting cell modulator (including but not limited to anti-CD40 antibody, anti-CD40L, anti-DC-SIGN, anti-Dectin-1, anti-CD301, anti-CD303, anti-CD123, anti-CD207, anti-DNGR1, anti-CD205, anti-DCIR, anti-CD206, anti-ILT7), a modulator for Toll-like receptors (including but not limited to anti-TLR-1, anti-TLR-2, anti-TLR-3, anti-TLR-4, anti-TLR-4, anti-TLR-5, anti-TLR-6, anti-TLR-7, anti-TLR-8, anti-TLR-9), an adhesion molecule blocker (including but not limited to an anti-LFA-1 antibody, an anti-E/L selectin antibody, a small molecule inhibitor), an anti-cytokine antibody or functional fragment thereof (including but not limited to an anti-IL-18, an anti-TNF, or an anti-IL-6/cytokine receptor antibody), a bispecific redirected T cell or NK cell cytotoxicity (including but not limited to a BiTE®), a chimeric T cell receptor (CAR-T) based therapy, a T cell receptor (TCR)-based therapy, a therapeutic cancer vaccine, methotrexate, cyclosporin, rapamycin, FK506, a detectable label or reporter, a TNF antagonist, an anti-rheumatic, a muscle relaxant, a narcotic, a non-steroid anti-inflammatory drug (NSAID), an analgesic, an anesthetic, a sedative, a local anesthetic, a neuromuscular blocker, an antimicrobial, an antipsoriatic, a corticosteriod, an anabolic steroid, an erythropoietin, an immunization, an immunoglobulin, an immunosuppressive, a growth hormone, a hormone replacement drug, a radiopharmaceutical, an antidepressant, an antipsychotic, a stimulant, an asthma medication, a beta agonist, an inhaled steroid, an epinephrine or analog, a cytokine, or a cytokine antagonist.

In an embodiment, a method of treating a cancer or in the prevention or inhibition of metastases from the tumors described herein, the CD27 receptor agonist protein(s) can be used alone or in combination with one or more additional agents, e.g., a chemotherapeutic, radiotherapy, or biological agent. In some embodiments, the agent can include the following: 13-cis-Retinoic Acid; 2-CdA; 2-Chlorodeoxyadenosine; 5-Azacitidine; 5-Fluorouracil; 6-Mercaptopurine; 6-MP; 6-TG; 6-Thioguanine; Abraxane; Accutane®; Actinomycin-D; Adriamycin®; Adrucil®; Afinitor®; Agrylin®; Ala-Cort®; Aldesleukin; Alemtuzumab; ALIMTA; Alitretinoin; Alkaban-AQ®; Alkeran®; All-transretinoic Acid; Alpha Interferon; Altretamine; Amethopterin; Amifostine; Aminoglutethimide; Anagrelide; Anandron®; Anastrozole; Arabinosylcytosine; Ara-C Aranesp®; Aredia®; Arimidex®; Aromasin®; Arranon®; Arsenic Trioxide; Arzerra™; Asparaginase; ATRA; Avastin®; Azacitidine; BCG; BCNU; Bendamustine; Bevacizumab; Bexarotene; BEXXAR®; Bicalutamide; BiCNU; Blenoxane®; Bleomycin; Bortezomib; Busulfan; Busulfex®; C225; Calcium Leucovorin; Campath®; Camptosar®; Camptothecin-11; Capecitabine Carac™ Carboplatin; Carmustine; Carmustine Wafer; Casodex®; CC-5013; CCI-779; CCNU; CDDP; CeeNU; Cerubidine®; Cetuximab; Chlorambucil; Cisplatin; Citrovorum Factor; Cladribine; Cortisone; Cosmegen®; CPT-11; Cyclophosphamide; Cytadren®; Cytarabine; Cytarabine Liposomal; Cytosar-U®; Cytoxan®; Dacarbazine; Dacogen; Dactinomycin; Darbepoetin Alfa; Dasatinib; Daunomycin; Daunorubicin; Daunorubicin Hydrochloride; Daunorubicin Liposomal; DaunoXome®; Decadron; Decitabine; Delta-Cortef®; Deltasone®; Denileukin; Diftitox; DepoCyt™; Dexamethasone; Dexamethasone Acetate; Dexamethasone Sodium Phosphate; Dexasone; Dexrazoxane; DHAD; DIC; Diodex; Docetaxel; Doxil®; Doxorubicin; Doxorubicin Liposomal; Droxia™; DTIC; DTIC-Dome®; Duralone®; Duvelisib; Efudex®; Eligard™; Ellence™; Eloxatin™; Elspar®; Emcyt®; Epirubicin; Epoetin Alfa; Erbitux; Erlotinib; Erwinia L-asparaginase; Estramustine; Ethyol Etopophos®; Etoposide; Etoposide Phosphate; Eulexin®; Everolimus; Evista®; Exemestane; Fareston®; Faslodex®; Femara®; Filgrastim; Floxuridine; Fludara®; Fludarabine; Fluoroplex®; Fluorouracil; Fluorouracil (cream); Fluoxymesterone; Flutamide; Folinic Acid; FUDR®; Fulvestrant; Gefitinib; Gemcitabine; Gemtuzumab ozogamicin; Gemzar; Gleevec™; Gliadel® Wafer; GM-CSF; Goserelin; Granulocyte-Colony Stimulating Factor (G-CSF); Granulocyte Macrophage Colony Stimulating Factor (G-MCSF); Halotestin®; Herceptin®; Hexadrol; Hexalen®; Hexamethylmelamine; HMM; Hycamtin®; Hydrea®; Hydrocort Acetate®; Hydrocortisone; Hydrocortisone Sodium Phosphate; Hydrocortisone Sodium Succinate; Hydrocortone Phosphate; Hydroxyurea; Ibrutinib; Ibritumomab; Ibritumomab Tiuxetan; Idamycin®; Idarubicin Ifex®; Interferon-alpha; Interferon-alpha-2b (PEG Conjugate); Ifosfamide; Interleukin-11 (IL-11); Interleukin-2 (IL-2); Irnatinib mesylate; Imidazole Carboxamide; Intron A®; ipilimumab, Iressae; Irinotecan; Isotretinoin; Ixabepilone; Ixempra™; KADCYCLA®; Kidrolase (t) Lanacort®; Lapatinib; L-asparaginase; LCR; Lenalidomide; Letrozole; Leucovorin; Leukeran; Leukine™; Leuprolide; Leurocristine; Leustatin™; Lirilumab; Liposomal Ara-C; Liquid Pred®; Lomustine; L-PAM; L-Sarcolysin; Lupron®; Lupron Depot®; Matulane®; Maxidex; Mechlorethamine; Mechlorethamine Hydrochloride; Medralone®; Medrol®; Megace®; Megestrol; Megestrol Acetate; MEK inhibitors; Melphalan; Mercaptopurine; Mesna; Mesnex™; Methotrexate; Methotrexate Sodium; Methylprednisolone; Meticorten®; Mitomycin; Mitomycin-C; Mitoxantrone M-Prednisol®; MTC; MTX; Mustargen®; Mustine; Mutamycin®; Myleran®; Mylocel™; Mylotarg®; Navitoclax; Navelbine®; Nelarabine; Neosar®; Neulasta™, Neumega®; Neupogen®; Nexavar®; Nilandron®; Nilotinib; Nilutamide; Nipent®; Nitrogen Mustard Novaldex®; Nivolumab; Novantrone®; Nplate; Octreotide; Octreotide acetate; Ofatumumab; Oncospar®; Oncovin®; Ontak® ; Onxal™; Oprelvekin; Orapred®; Orasone®; Oxaliplatin; Paclitaxel; Paclitaxel Protein-bound; Pamidronate; Panitumumab; Panretin®; Paraplatin®; Pazopanib; Pediapred®; PEG Interferon; Pegaspargase; Pegfilgrastim; PEG-INTRON™; PEG-L-asparaginase; PEMETREXED; Pembrolizumab; Pentostatin; Pertuzumab; Phenylalanine Mustard; Pidilizumab; Platinol®; Platinol-ACM; Prednisolone; Prednisone; Prelone®; Procarbazine; PROCRIT®; Proleukin®; Prolifeprospan 20 with Carmustine Implant; Purinethol®; BRAF inhibitors; Raloxifene; Revlimid®; Rheumatrex®; Rituxan®; Rituximab; Roferon-A®; Romiplostim; Rubex®; Rubidomycin hydrochloride; Sandostatin®; Sandostatin LAR®; Sargramostim; Solu-Cortef®; Solu-Medrol®; Sorafenib; SPRYCEL™; STI-571; STIVAGRA™, Streptozocin; SU11248; Sunitinib; Sutent®; Tamoxifen Tarceva®; Targretin®; Tasigna®; Taxol®; Taxotere®; Temodar®; Temozolomide Temsirolimus; Teniposide; TESPA; Thalidomide; Thalomid®; TheraCys®; Thioguanine; Thioguanine Tabloid®; Thiophosphoamide; Thioplex®; Thiotepa; TICE®; Toposar®; Topotecan; Toremifene; Torise®; Tositumomab; Trastuzumab; Treanda®; Tremelimumab; Tretinoin; Trexall™; Trisenox®; TSPA; TYKERB®; Urelumab; VCR; Vectibix™; Velban®; Velcade®; Venetoclax; VePesid®; Vesanoid®; Viadur™; Vidaza®; Vinblastine; Vinblastine Sulfate; Vincasar Pfs®; Vincristine; Vinorelbine; Vinorelbine tartrate; VLB; VM-26; Vorinostat; Votrient; VP-16; Vumon®; Xeloda®; Zanosar®; Zevalin™; Zinecard®; Zoladex®; Zoledronic acid; Zolinza; or Zometa®, and/or any other agent not specifically listed here that target similar pathways.

When two or more substances or principles are to be used as part of a combined treatment regimen, they can be administered via the same route of administration or via different routes of administration, at essentially the same time or at different times (e.g. essentially simultaneously, consecutively, or according to an alternating regime). When the substances or principles are to be administered simultaneously via the same route of administration, they may be administered as different pharmaceutical formulations or compositions or part of a combined pharmaceutical formulation or composition, as will be clear to the skilled person.

Also, when two or more active substances or principles are to be used as part of a combined treatment regimen, each of the substances or principles may be administered in the same amount and according to the same regimen as used when the compound or principle is used on its own, and such combined use may or may not lead to a synergistic effect. However, when the combined use of the two or more active substances or principles leads to a synergistic effect, it may also be possible to reduce the amount of one, more than one, or all of the substances or principles to be administered, while still achieving the desired therapeutic action. This may, e.g., be useful for avoiding, limiting or reducing any unwanted side-effects that are associated with the use of one or more of the substances or principles when they are used in their usual amounts, while still obtaining the desired pharmaceutical or therapeutic effect.

The effectiveness of the treatment regimen used according to the invention may be determined and/or followed in any manner known per se for the disease or disorder involved, as will be clear to the clinician. The clinician will also be able, where appropriate and on a case-by-case basis, to change or modify a particular treatment regimen, so as to achieve the desired therapeutic effect, to avoid, limit or reduce unwanted side-effects, and/or to achieve an appropriate balance between achieving the desired therapeutic effect on the one hand and avoiding, limiting or reducing undesired side effects on the other hand.

Generally, the treatment regimen will be followed until the desired therapeutic effect is achieved and/or for as long as the desired therapeutic effect is to be maintained. Again, this can be determined by the clinician.

In various embodiments, pharmaceutical compositions comprising one or more CD27 receptor agonist proteins, either alone or in combination with prophylactic agents, therapeutic agents, and/or pharmaceutically acceptable carriers are provided herein. In various embodiments, non-limiting examples of the uses of the pharmaceutical compositions disclosed herein include diagnosing, detecting, and/or monitoring a disorder, preventing, treating, managing, and/or ameliorating a disorder or one or more symptoms thereof, and/or in research. The formulation of pharmaceutical compositions, either alone or in combination with prophylactic agents, therapeutic agents, and/or pharmaceutically acceptable carriers, are known to one skilled in the art (US Patent Publication No. 20090311253 A1).

As used herein, the phrase "effective amount" means an amount of CD27L agonist protein that results in a detectable improvement (e.g., at least about 5%, 10%, 15%, 20%, 25%, 30%, 35%, 40%, 45%, 50%, 55%, 60%, 65%, 70%, 75%, or more from baseline) in one or more parameters associated with a dysfunction of CD27L or with a CD27L-associated disease or disorder.

Methods of administering a therapeutic agent provided herein include, but are not limited to, oral administration, parenteral administration (e.g., intradermal, intramuscular, intraperitoneal, intravenous and subcutaneous), epidural administration, intratumoral administration, mucosal administration (e.g., intranasal and oral routes) and pulmonary administration (e.g., aerosolized compounds administered with an inhaler or nebulizer). The formulation of pharmaceutical compositions for specific routes of administration, and the materials and techniques necessary for the various methods of administration are available and known to one skilled in the art (US Patent Publication No. 20090311253 A1).

In various embodiments, dosage regimens may be adjusted to provide for an optimum desired response (e.g., a therapeutic or prophylactic response). For example, a single bolus may be administered, several divided doses may be administered over time or the dose may be proportionally reduced or increased as indicated by the exigencies of the therapeutic situation. In some embodiments, parenteral compositions are formulated in dosage unit form for ease of administration and uniformity of dosage. The term "dosage unit form" refers to physically discrete units suited as unitary dosages for the mammalian subjects to be treated; each unit containing a predetermined quantity of active compound calculated to produce the desired therapeutic effect in association with the required pharmaceutical carrier.

An exemplary, non-limiting range for a therapeutically or prophylactically effective amount of a CD27 receptor agonist protein provided herein is about 0.1-100 mg/kg, (e.g., about 0.1-0.5, 0.1-1, 0.1-10, 0.1-20, 0.1-50, 0.1-75, 1-10, 1-15, 1-7.5, 1.25-15, 1.25-7.5, 2.5-7.5, 2.5-15, 5-15, 5-7.5, 1-20, 1-50, 7-75, 1-100, 5-10, 5-15, 5-20, 5-25, 5-50, 5-75, 10-20, 10-50, 10-75, or 10-100 mg/kg, or any concentration in between). In some embodiments, the CD27 receptor agonist protein is present in a pharmaceutical composition at a therapeutically effective concentration, e.g., a concentration of about 0.1-100 mg/ml (e.g., about 0.1-0.5, 0.1-1, 0.1-10, 0.1-20, 0.1-50, 0.1-75, 1-10, 1-20, 1-50, 1-75, 1-100, 5-10, 5-15, 5-20, 5-25, 5-50, 5-75, 10-20, 10-50, 10-75. or 10-100 mg/ml, or any concentration in between). Note that dosage values may vary with the type and/or severity of the condition to be alleviated. It is to be further understood that for any particular subject, specific dosage regimens may be adjusted over time according to the individual need and/or the professional judgment of the person administering or supervising the administration of the compositions, and that dosage ranges set forth herein are exemplary only and are not intended to limit the scope or practice of the claimed composition.

EXAMPLES

Example 1

Manufacture of a CD27 Receptor Agonist Protein 1.1 Polypeptide Structure

A) Amino acids Met1-Gly20 Ig-Kappa-signal peptide, assumed signal peptidase cleavage site after amino acid Gly 20.
B) Amino acids Glu21-Pro163 First soluble cytokine domain of the human CD27L ligand (CD27L, amino acid 51-193 of SEQ ID NO: 1).
C) Amino acids Gly164-Ser 171 First peptide linker element of SEQ ID NO: 2.
D) Amino acids Glu172-Pro314 Second soluble cytokine domain of the human CD27L ligand (CD27L, amino acids 51-193 of SEQ ID NO: 1).
E) Amino acids Gly315-Ser322. Second peptide linker element of SEQ ID NO: 2.
F) Amino acids Glu323-Pro465 Third soluble cytokine domain of the human CD27L ligand (CD27L, amino acids 51-193 of SEQ ID NO: 1).
G) Amino acids Gly466-Cys486 Hinge-linker element of SEQ ID NO: 16.
H) Amino acids Pro487-Lys704 Antibody Fc fragment domain of SEQ ID NO: 13.

The above CD27 receptor agonist protein is shown in SEQ ID NO: 25.

The indicated linkers may be replaced by other preferred linkers, e.g. as shown in SEQ ID NOs: 3-12.

The indicated Hinge-linker element may be replaced by other preferred Hinge-linkers, e.g. as shown in SEQ ID NOs: 19-24.

It should be noted that the first and second peptide linkers do not need to be identical.

The signal peptide sequence (A) may be replaced by any other suitable, e.g. mammalian signal peptide sequence.

1.2 Gene Cassette Encoding the Polypeptide

The synthetic gene may be optimized in view of its codon usage for the expression in suitable host cells, e.g. insect cells or mammalian cells. A preferred nucleic acid sequence is shown in SEQ ID NO: 37.

Example 2

Expression and Purification 2.1 Cloning, Expression and Purification of Fusion Polypeptides The aforementioned fusion proteins are expressed recombinantly in two different eukaryotic host cells employing the methods described below:

Method for Small Scale Expression of of CD27 Receptor Agonist Fusion Proteins:

For initial analysis of aforementioned CD27 receptor agonist fusion proteins, Hek293 cells grown in DMEM+GlutaMAX (GibCo) supplemented with 10% FBS, 100 units/ml Penicillin and 100 [mu]g/ml Streptomycin are transiently transfected with a plasmid containing an expression cassette for a fusion polypeptide and an appropriate selection marker, e.g. a functional expression cassette comprising a blasticidine, puromycin or hygromycin resistance gene. In those cases, where a plurality of polypeptide chains is necessary to achieve the final product, the expression cassettes will be either combined on one plasmid or positioned on different plasmids during the transfection. Cell culture supernatant containing recombinant fusion polypeptide will be harvested three days post transfection and clarified by centrifugation at 300×g followed by filtration through a 0.22 μm sterile filter.

Method for Large Scale Expression and Purification of CD27 Receptor Agonist Fusion Proteins For larger scale expression of CD27 receptor agonist fusion proteins to be used in vivo, synthetic DNA cassettes encoding the aforementioned proteins is inserted into eukaryotic expression vectors comprising appropriate selection markers (e.g. a functional expression cassette comprising a blasticidin, puromycin or hygromycin resistance gene) and genetic elements suitable to enhance the number of transcriptionally active insertion sites within the host cells genome. The sequence verified expression vectors are introduced by electroporation into suspension adapted Chinese Hamster Ovary cells (CHO-S, Invitrogen). Appropriate selection pressure will be applied three days post-transfection to the transfected cells. Surviving cells carrying the vector derived resistance gene(s) are recovered by subsequent cultivation under selection pressure. Upon stable growth of the selected cell pools in chemically defined medium (PowerCHO2-CD, Lonza) at 37° C. and 7% CO2 atmosphere in an orbital shaker incubator (100 rpm, 50 mm shaking throw), the individual supernatants are analyzed by ELISA-assays detecting the aforementioned proteins and the cell pools with the highest specific productivity which were expanded in shake flasks prior to protein production (orbital shaker, 100 rpm, shaking throw 50 mm).

For lab-scale protein production, individual cell pools are cultured for 7-12 days in chemically defined medium (PowerCHO2-CD, Lonza) at 37° C. and 7% CO2 atmosphere in a Wave bioreactor 20/50 EHT (GE-Healthcare). The basal medium is PowerCHO2-CD supplemented with 4 mM Glutamax. Wave culture is started with a viable cell concentration of 0.3 to 0.4×10e6 cells/ml and the following settings (for a five- or ten liter bag): shaking frequency 18 rpm, shaking ankle 7°, gas current 0.2-0.3 L/min, 7% CO2, 36.5° C. During the Wave run, the cell culture is fed twice with PowerFeed A (Lonza), usually on day 2 (20% feed) and day 5 (30% feed). After the second feed, shaking frequency is increased to 22 rpm, as well as the shaking ankle to 8°.

The bioreactor is usually harvested in between day 7 to day 12 when the cell viability drops below 80%. First, the culture supernatant is clarified using a manual depth filtration system (Millipore Millistak Pod, MCOHC 0.054 m²). For Strep-tagged proteins, Avidin is added to a final concentration of 0.5 mg/L. Finally, the culture supernatant containing the CD27 receptor agonist fusion protein is sterile filtered using a bottle top filter (0.22 µm, PES, Corning) and stored at 2-8° C. until further processing.

For affinity purification Streptactin Sepharose is packed to a column (gel bed 2 ml), equilibrated with 15 ml buffer W (100 mM Tris-HCl, 150 mM NaCl, pH 8.0) or PBS pH 7.4 and the cell culture supernatant is applied to the column with a flow rate of approx. 4 ml/min. Subsequently, the column is washed with 15 ml buffer W and bound polypeptide is eluted stepwise by addition of 7×1 ml buffer E (100 mM Tris HCl, 150 mM NaCl, 2.5 mM Desthiobiotin, pH 8.0). Alternately, PBS pH 7.4 containing 2.5 mM Desthiobiotin can be used for this step.

Alternatively to the Streptactin Sepharose based method, the affinity purification is performed employing a column with immobilized Protein-A as affinity ligand and an Äkta chromatography system (GE-Healthcare). A solid phase material with high affinity for the FC-domain of the fusion protein was chosen: MABSelect Sure™ (GE Healthcare). Briefly, the clarified cell culture supernatant is loaded on a HiTrap MabSelectSure column (CV=5 ml) equilibrated in wash-buffer-1 (20 mM Pi, 95 mM NaCl, pH7.2) not exceeding a load of 10 mg fusion protein per ml column-bed. The column is washed with ten column-volumes (10CV) of aforementioned equilibration buffer followed by four column-volumes (4CV) of wash-buffer-2 (20 mM Pi, 95 mM NaCl, pH 8.0) to deplete host-cell protein and host-cell DNA. The column is then eluted with elution buffer (20 mM Pi, 95 mM NaCl, pH 3.5) and the eluate is collected in up to ten fractions with each fraction having a volume equal to column-bed volume (5 ml). Each fraction is neutralized with an equal volume of aforementioned wash-buffer-2. The linear velocity is set to 150 cm/h and kept constant during the aforementioned affinity chromatography method. The protein amount of the eluate fractions is quantitated and peak fractions are concentrated by ultrafiltration and further purified by size exclusion chromatography (SEC).

Figure 5:
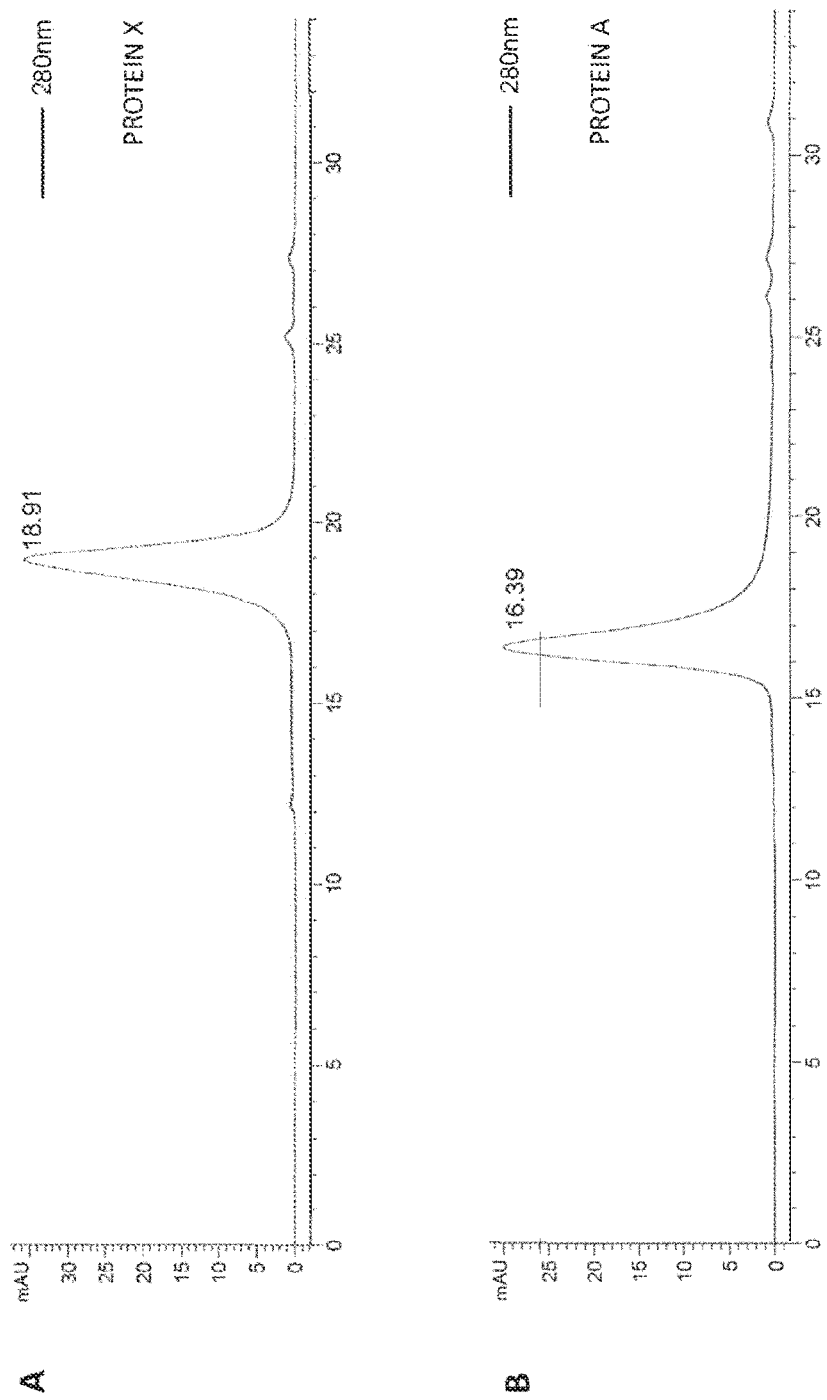
FIG. 5 Analytical size exclusion chromatography of PROTEIN A (SEQ ID NO: 15) and PROTEIN X (SEQ ID NO: 38) performed on a 1260 Infinity HPLC system using a Tosoh TSKgelG3000SWxI column. The column was loaded with protein at a concentration of 0.6 mg/ml in a total volume of 20 μl. The flow rate was set to 0.5 ml/min. One observes a single main peak at 16.39 min for PROTEIN A (Part B) and 18.91 min for PROTEIN X (Part A).

Analytical size exclusion chromatography of PROTEIN A (SEQ ID NO: 15) and the trivalent control protein PROTEIN X (SEQ ID NO: 38) is shown in FIG. 5. For preparation of the control protein please refer to Example 4. The SEC was performed on a 1260 Infinity HPLC system using a Tosoh TSKgelG3000SWxl column. The column was loaded with protein at a concentration of 0.6 mg/ml in a total volume of 20 µl. The flow rate was set to 0.5 ml/min. One observes a single main peak at 16.39 min for PROTEIN A (FIG. 5: Part B) and 18.91 min for PROTEIN X (FIG. 5 Part A). By using an internal molecular weight standard (BioRad SEC Standard) one can intrapolate the molecular weight of PROTEIN A and PROTEIN X from respective retention times. Consequently, PROTEIN X has an apparent molecular weight of 80.4 kDa and PROTEIN A shows a molecular weight of 201.8 kDA. These values are in line with theoretically expected values derived from the amino acid sequence.

Employing the aforementioned methods, recombinant CD27 receptor agonist fusion protein (PROTEIN-A, SEQ ID NO: 15) was expressed in CHO-S cells and purified employing affinity chromatography and subsequent SEC-based polishing. The chromatogram of an analytical SEC of hexavalent scCD27L-RBD-FC (PROTEIN-A, SEQ ID NO: 15) fusion protein is shown in FIG. 5 (Part B). The chromatogram of an analytical SEC of trivalent control protein (PROTEIN X SEQ ID NO: 38) is shown in FIG. 5 (Part A).

For determination of the apparent molecular weight of purified fusion polypeptide under native conditions a Superdex 200 column was loaded with standard proteins of known molecular weight. Based on the elution volume of the standard proteins a calibration curve was plotted and the apparent molecular weight of purified fusion polypeptide was determined. The FC-domain comprising CD27 receptor agonist fusion proteins typically eluted from the Superdex200 columns with an apparent molecular weight of approx. 160-180 kDa confirming the homodimerisation of the mature CD27 receptor agonist fusion polypeptide by the Fc domain.

Example 3

SDS-PAGE Results of Dimer Proteins Expressed from Protein A

Figure 7:
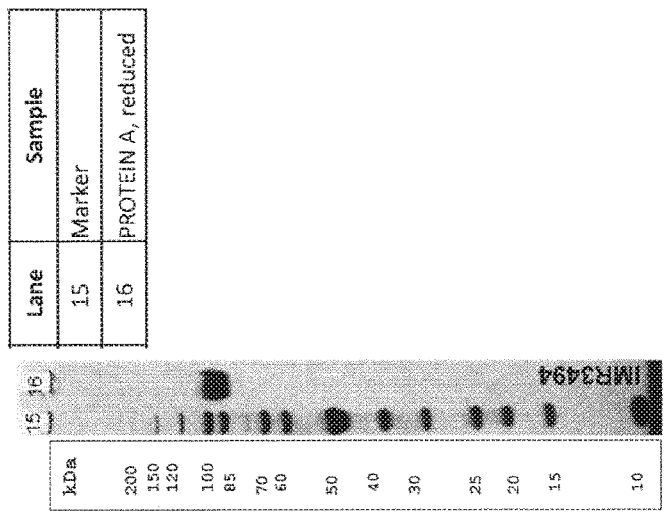
FIG. 7 SDS-PAGE results of PROTEIN A under non-reducing and reducing conditions. 465 ng of PROTEIN A were loaded on an SDS-PAGE 4-12% Bis-Tris gel under non-reducing (A) or reducing (B) conditions containing DTT as reducing agent. Gels were run at 170V for 60 min and were subsequently stained using a silver-stain protocol. One observes a molecular weight difference between the main bands in A and B of about 80-100 kDa. As this is about half the molecular weight as observed for the main band in A, this indicates that the homodimer in A is covalently linked by disulfide bridges. The bonds are lost under reducing conditions in B FIG. 8 Elution fractions from affinity chromatography of PROTEIN X along with column load and flow-through samples were loaded on an SDS-PAGE 4-12% Bis-Tris gel under reducing (lanes 2-8) or non-reducing (lanes 10-16) conditions. DTT was used as reducing agent. Gels were run at 170V for 60 min and were subsequently stained using a silver-stain protocol. Single bands of PROTEIN X can be seen in lanes 4-6 and 12-14 indicating that all protein elutes from the column in fractions 1 to 3. Shown is: Lane 1 and 9: marker/lane 17: empty/lane 2-8 and 10-16: Protein X with: (2) reduced column load; (3) reduced column flow-through; (4) reduced elution fraction 1; (5) reduced elution fraction 2; (6) reduced elution fraction 3; (7) reduced elution fraction 4; (8) reduced elution fraction 5; (10) non reduced column load; (11) non reduced column flow-through; (12) non-reduced elution fraction 1; (13) non-reduced elution fraction 2; (14) non-reduced elution fraction 3; (15) non-reduced elution fraction 4; (16) non-reduced elution fraction 5
Figure 7:
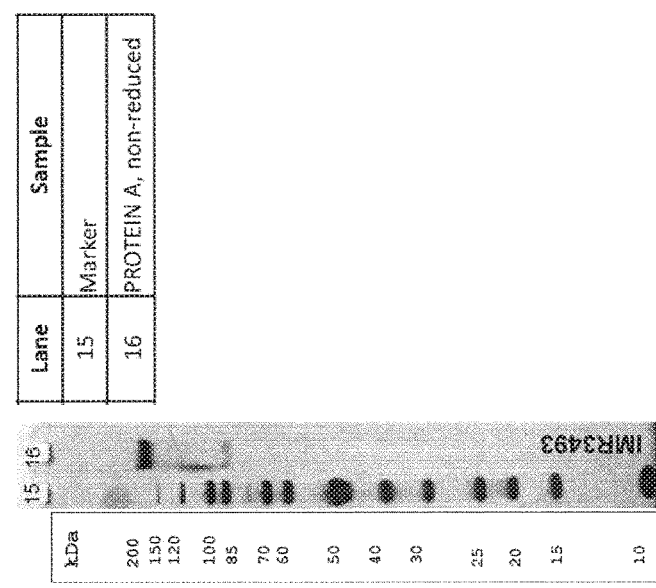
Figure 8:
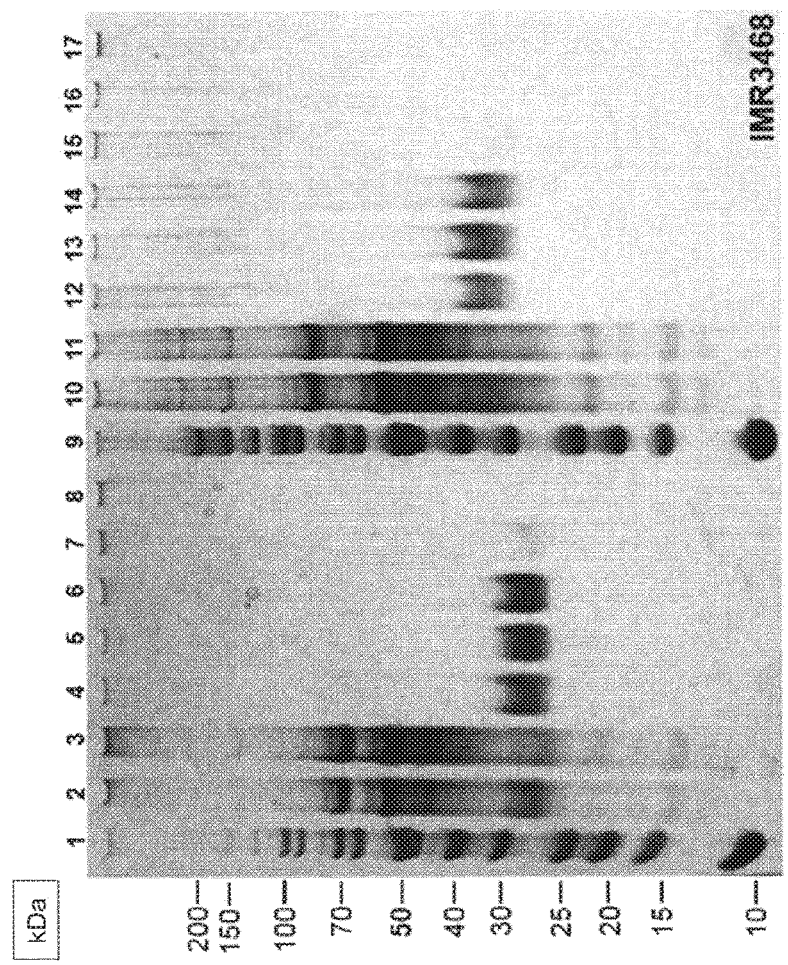

To determine if the homodimer of Protein A is covalently linked, sodium dodecyl sulfate polyacrylamide gel electrophoresis (SDS-PAGE) experiments were performed under reducing and non-reducing conditions. The size of the main band under reducing conditions is only about half of the size as observed under non-reducing conditions. This indicates that the homodimer is covalently linked by disulfide bridges (see also FIG. 7).

Example 4

Trivalent Control Protein

To compare the relative binding between hexavalent CD27 receptor agonist fusion proteins and the, trivalent CD27 stabilized with bacteriophage RB69-FOLDON, PROTEIN X (SEQ ID NO: 38) was expressed in CHO-S cells and purified as described in the former section. The SEC-purified protein is served as control in the following Examples. The sequence of PROTEIN X (SEQ ID NO: 38) is shown in Table 7. Amino-acids 1-20 of PROTEIN X represent the signal peptide and the mature proteins starts with amino acid Glu51. This protein consists of three identical polypeptides each comprising one soluble CD27L domain (E51-P193 of SEQ ID NO: 1); this assembly stabilized by the trimerisation domain of bacteriophage RB69 fibritin fused with a flexible linker to the C-terminus of CD27L.

TABLE 7

Trivalent control protein including a signal peptide

| SEQ ID NO | Sequence |
|---|---|
| 38 | METDTLLVFVLLVWVPAGNGESLGWDVAELQLNHTGPQQDPRLYWQGGPALGRSF LHGPELDKGQLRIHRDGIYMVHIQVTLAICSSTTASRHHPTTLAVGICSPASRSI SLLRLSFHQGCTIASQRLTPLARGDTLCTNLTGTLLPSRNTDETFFGVQWVRPGS GSSGSSGSSGSGYIEDAPSDGKFYVRKDGAWVELPTASGPSSSSSSAWSHPQFEK |

Example 5

CD27 Receptor Agonist Combined with TCR Activation Activates Murine T-Cells

To assess the T cell activation capability of the CD27 receptor agonist protein, T cells are purified from mouse spleens by negative selection using magnetic beads. Cells are labeled with CFSE and incubated with or without varying amounts of the CD27 receptor agonist protein and combined with an anti-mouse CD3 antibody for 2-5 days at 37° C. Data on CFSE dilution as a means to measure cell division is acquired on a flow cytometer. IFNγ production is measured by an ELISA assay using cell culture supernatants and an anti-mouse IFNγ antibody for capture.

One expects to observe a clear augmentation of IFNγ secretion by both CD4+ and CD8+ T cells when the CD27 receptor agonist protein is present in the T cell cultures along with the anti-mouse CD3 antibody. As well as higher IFNγ production one expects to see more T cells to be driven into cell cycle by measuring CFSE dilution using flow cytometry. This would demonstrate a co-stimulatory effect of the CD27 receptor agonist protein in the context of T cell activation.

Example 6

In Vivo Binding of CD27 Receptor Agonist Protein to Mouse Immune Cells and the Effect on Circulating Lymphocytes To assess the binding of the CD27 receptor agonist protein to immune cells in vivo, mice are treated with or without a single i.v. injection of the CD27 receptor agonist protein at varying concentrations. Animals are followed for up to 20 days and blood samples are collected daily starting on the day of injection. Blood samples are incubated with a fluorescent anti-human Fc antibody on ice and red blood cells are subsequently lysed using red blood cell lysis buffer. Samples are then analyzed on a flow cytometer. Total lymphocytes from blood are identified based on their side and forward scatter profile and stained populations from injected mice are compared to cells from untreated control animals.

One expects the CD27 receptor agonist protein to bind to the surface of circulating lymphocytes expressing the target receptor CD27. The binding is likely to decline over time due to target-mediated drug disposition, which potentially occurs via internalization of agonist/receptor complexes.

In addition, the effect of the CD27 receptor agonist protein on circulating lymphocyte populations is assessed. For that purpose blood samples from mice, which receive a single i.v. injection of the CD27 receptor agonist protein at varying concentrations are obtained daily over the course of 20 days starting on the day of injection (see above). After red blood cell lysis, cells are stained with fluorescent antibodies directed against immune cell subsets such as B cells, CD4+ T cells, CD8+ T cells or NK cells. Stained samples are analyzed on a flow cytometer.

One expects to observe no significant changes in the number of circulating immune cell subsets over the course of the treatment period.

Example 7

CD27 Receptor Agonist Protein Enhances Antigen-Specific CD8+ T-Cell Proliferation and Activation as well as Pentamer Staining on Mouse Peripheral Blood Cells and Splenocytes Mice are intravenously injected with 1-10 mg of chicken ovalbumin in combination with varying amounts of the CD27 receptor agonist protein. Anti-mouse CD27 and an irrelevant human IgG1 antibody are included as positive and negative controls, respectively. The CD27 receptor agonist protein is co-injected with ovalbumin on day 0 and an additional amount of CD27 receptor agonist protein alone on day 1. Peripheral blood and spleen cells are harvested on days 7-10. Splenocytes and whole-blood are used for staining. After Fc-receptor blocking, cells are stained, at room temperature for 30 min to 1 h, with fluorescently labelled H-2 Kb/SIINFEKL, a tetrameric complex of mouse MHC class I complexed with the peptide T cell epitope from ovalbumin, and additionally with fluorescent antibodies detecting mouse CD8 and mouse CD27, Samples are subsequently treated with red blood cell lysis buffer to eliminate red blood cells, washed and fixed. Cells are analyzed on a flow cytometer counting the number of cells within the CD8+ and CD27+ T cell compartment, which recognize the SIINFEKL peptide in the context of MHC class I and which are thus antigen specific.

One would expect to observe a supplementary effect elicited by the CD27 receptor agonist protein in a sense that the agonist enhances the expansion of antigen-specific CD8+ T cells in the context of an immune response. This would demonstrate a clear co-stimulatory effect exerted by the CD27 receptor agonist protein.

Example 8

Determination of the in Vitro Stability of CD27 Receptor Agonist Proteins by Limited Protease Digestion All CD27 receptor agonist proteins to be investigated will be expressed and purified as hexavalent Fc-Fusion protein as described in Example 1. The set will include CD27 receptor agonist proteins comprising the N297S mutation [according to the EU numbering system] in the CH2-domain and a hinge region that enables the formation of three disulfide bridges and additionally lack the upper hinge lysine [K223, according to the EU numbering system] which is mutated to glycine [K223G], In a limited protease digestion assay, the aforementioned CD27 receptor agonist proteins comprising the N297S mutation and the K223G mutation simultaneously in context of a three disulfide enabling hinge will be compared to CD27 receptor agonist proteins comprising the N297S mutation but have the K223 wildtype present either in the context of a two disulfide or three disulfide enabling hinge region.

In addition CD27 receptor agonist proteins with the second linker element (iv) reduced to 4 amino-acids and the shortened hinge element (vi) will be investigated (e.g. SEQ ID NO: 32 and 34). Both engineering strategies (N297S combined with K223G mutation in context of a three disulfide enabling hinge region) and shortage of linker elements (iv and vi) have a potential impact on the stability of the respective molecules. The stability of different CD27 agonistic proteins of the present invention can be addressed by limited protease digestion in vitro. For this analysis, the aforementioned CD27 receptor agonist proteins are incubated with low concentrations of proteases (e.g. Trypsin, V8 protease) at different temperatures (e.g. 4° C., 25° C., 37° C.) for different amounts of time. Quantification of specific proteolytic fragments and their appearance over time can be subsequently measured by different methods, like SDS-PAGE, analytical SEC or analytical Mass-Spectrometry methods known in the art (e.g Nano-RP-HPLC-ESI-MSMS). As the investigated proteins have most of their sequences in common, the faster appearance and enlarged quantities of specific proteolytic fragments from individual proteins over time can then be used to judge their relative stability and rank them to each other. With regard to protease based decoy kinetics of the aforementioned CD27 receptor agonist proteins investigated, the following order regarding their proteolytic stability is to be expected:

The CD27 receptor agonist proteins comprising the N297S and the K223G and the three disulfide enabling hinge region simultaneously have a prolonged stability as compared to the CD27 receptor agonist proteins comprising the N297S and wildtype K223 in the hinge region. The CD27 receptor agonist proteins comprising the SEQ ID NO: 21 as hinge linker have a prolonged stability as compared to CD27 receptor agonist proteins comprising the SEQ ID NO: 16 as hinge linker element.

Example 9

Half-Life Determination

Molecule PROTEIN A is made up of two polypeptides covalently linked by three interchain disulfide bonds and comprises the K223G mutation in the hinge linker as well as the N297S mutation the Fc region (according to the EU numbering), resulting in aglycosylation of the CH2 domain. The purified PROTEIN-A was tested on the half-life in mice.

Female CD1 mice were administered with 1.0 mg/kg of PROTEIN A as a single intravenous bolus injection. Whole blood was collected before application (pre-dose), and up to 312 hours after test item administration. Serum was prepared and samples were stored at −80° C. until determination of serum concentrations.

Quantitation of the PROTEIN A concentrations in mouse serum was performed with an ELISA-assay detecting the CD27 agonist shown in Table 8. Plates were coated with CD27-Fc. CD27-Ligand constructs specifically binding to its receptor CD27 were then detected via their Strep-Tag employing StrepTactin-HRP. ELISA assays were carried out using reference PROTEIN A as calibration and control samples. The measured data of the standard concentrations were used to create calibration curves using a 5-parameter fit. This enabled the determination of the unknown PROTEIN A concentrations in the respective mouse serum samples.

Pharmacokinetic parameters were calculated using the mean serum concentrations and the pharmacokinetic evaluation program PK Solutions Version 2.0 for non-compartmental pharmacokinetic data analysis (Summit Research Services, Montrose, Colo.). PK Solutions is an automated, Excel-based application, which computes pharmacokinetic parameters from concentration-time data obtained from analysis of e.g. biological samples following intravenous or extra-vascular routes of administration. PK Solutions calculates results without presuming any specific compartmental model.

The results from the pharmacokinetics evaluation are summarized in Table 8.

TABLE 8

Results of the exploratory PK study in CD1-mice: single intravenous dose of 1 mg/kg of PROTEIN A.

| | PROTEIN A |
|---|---|
| $t_{max}$ (h) | 0.083 |
| $C_{max}$ (µg/ml) | 9.63 |
| $t_{last}$ (h) | 24 |

TABLE 8-continued

Results of the exploratory PK study in CD1-mice: single intravenous dose of 1 mg/kg of PROTEIN A.

| | PROTEIN A |
|---|---|
| $C_{last}$ (µg/ml) | 0.288 |
| $t_{1/2}$ E (h) | 10.42 |
| $t_{1/2}$ E (d) | 0.43 |
| $AUC_{0-t}$ (µg * h/ml) | 33 |
| $AUC_{0-inf}$ (µg * h/ml) | 38 |

The results show that PROTEIN A has a surprisingly short terminal half-life of 10.42 hours in mice. This short half-life constitutes a favorable therapeutic option since a short co-stimulatory stimulus with CD27 receptor agonist proteins is desirable.

Example 10

Stability/Aggregation Test

The contents of monomers and aggregates are determined by analytical SEC as described in Example 2. For this particular purpose the analysis is performed in buffers containing physiological salt concentrations at physiological pH (e.g. 0.9% NaCl, pH 7.4; PBS pH 7.4). A typical aggregation analysis is done on a Superdex200 column (GE Healthcare). This column separates proteins in the range between 10 to 800 kDa.

For determination of the apparent molecular weight of purified fusion polypeptide under native conditions a Superdex 200 column is loaded with standard proteins of known molecular weight. Based on the elution volume of the standard proteins a calibration curve is plotted and the apparent molecular weight of purified fusion proteins of unknown molecular weight is calculated based on the elution volume.

SEC analysis of soluble, non-aggregated protein typically shows a distinct single protein peak at a defined elution volume (measured at OD at 280 nm or at OD 214 nm). This elution volume corresponds to the apparent native molecular weight of the particular protein. With regard to the definition of "monomer" in the case of FC-fusion proteins, the assembly of two polypeptide-chains is driven by the FC-part of the protein and the functional unit is a protein consisting of two chains. This unit that contains two FC-linked polypeptide chains is defined as "monomer" in the case of Fc-fusion proteins regardless of being a dimerized single-chain fusion polypeptide.

If protein aggregation occurs, the SEC analysis shows additional protein peaks with lower retention volumes. Protein oligomers potentially serve as aggregation seeds and a high content of oligomers potentially leads to aggregation of the protein. Oligomers of large molecular weight and aggregates elute in the void volume of the Superdex200 column and cannot be analyzed by SEC with respect to their native molecular weight.

Purified preparations of CD27 receptor agonist fusion proteins should preferably contain only defined monomeric protein and only a very low amount of oligomeric protein. The degree of aggregation/oligomerization of a particular CD27 receptor agonist fusion protein preparation is determined on basis of the SEC analysis by calculating the peak areas of the OD280 diagram for the defined monomer and the oligomer/aggregate fraction, respectively. Based on the total peak area the percentage of defined monomer protein is calculated as follows:

monomer content [%]=[Peak area monomer protein]/[Total peak area]×100)

Example 11

Determination of the Equilibrium Binding Constants for Tri- and Hexavalent CD27 Receptor Ligand Constructs by QCM Analysis The equilibrium binding constants ($K_D$) of trivalent and hexavalent PROTEIN X and PROTEIN A are calculated based on kinetic binding data ($k_{on}$ and $k_{off}$) that are determined with an automated biosensor system (Attana A100). The A100 allows to investigate molecular interactions in real-time based on the Quartz Crystal Microbalance (QCM) technique.

For this purpose the human CD27 receptor is immobilized to the surface of a carboxyl-activated QCM-chip. Subsequently the tri- or hexavalent PROTEIN X or PROTEIN A, respectively, is used as an analyte at different concentrations (e.g. 0.5, 1, 2, 5, and 10 µg/ml) for analyzing the kinetic binding data for ligand-receptor binding ($k_{on}$) and dissociation ($k_{off}$). The analysis is done in real time and the respective $K_D$ can be calculated: $K_D=k_{off}/k_{on}$.

The QCM analysis shows that the trivalent PROTEIN X binds to the respective immobilized CD27 receptor with a $K_D$ in the low nM-range with an expected $K_D$ of 1-100 nm. However, hexavalent constructs of PROTEIN A show a higher binding affinity in the pM-range towards the respective immobilized CD27 receptor with an expected $K_D$ of 1-1000 pM. A common characteristic of the kinetic binding data ($k_{on}$ and $k_{off}$) is that the hexavalent constructs show faster $k_{on}$ in comparison to the trivalent constructs. In addition slower dissociation ($k_{off}$) is commonly observed for the hexavalent ligands if compared to the trivalent ligand.

Example 12

T Cell Proliferation Assay

Primary, human T cells were isolated from fresh buffy coat preparations using negative selection and magnetic beads. Cells were loaded with the dye CFSE and were seeded into 24-well plates at 2×10e6 cells per well. T cells were incubated with an anti-human CD3 antibody (clone HIT3a, 1 µg/ml), anti-human CD28 antibody (clone CD28.2, 5 µg/ml) and varying amounts of the CD27L agonist (Protein A), 10-1000 ng/ml) or simply left in medium as control. All cells were assessed for CFSE fluorescence on a guava easyCyte flow cytometer after 6 days of incubation at 37° C.

It was observed (Table 9) that cells only incubated with the anti-CD3 and anti-CD28 antibodies loose CFSE fluorescence (GeoMean) compared to the medium control indicating cell division thereby diluting the CFSE dye. Importantly, this effect was even stronger and concentration-dependent when cells were also incubated with the CD27L agonist (Protein A). Using the GeoMean values one can derive a percentage for cells driven into proliferation and it is clear that cells incubated with the CD27L (Protein A) agonist proliferated stronger than cells only being incubated with anti-CD3 and anti-CD28 antibodies or being left in medium alone.

TABLE 9

Protein A dependent T Cell Proliferation Assay

| Stimulation | % of proliferating cells | GeoMean (All events) |
|---|---|---|
| Medium | 0.39 | 559.94 |
| a-CD3+a-CD28 | 21.57 | 292.85 |
| a-CD3+a-CD28+CD27L 10 ng/ml | 35.64 | 180.9 |
| a-CD3+a-CD28+CD27L 100 ng/ml | 44.87 | 140.92 |
| a-CD3+a-CD28+CD27L 1000 ng/ml | 50.03 | 137.17 |

Example 13

CD27 Agonist Binding Assay

Primary, human T cells were isolated from fresh buffy coat preparations using negative selection and magnetic beads. Cells were seeded into 24-well plates at 2×10e6 cells per well. T cells were incubated with an anti-human CD3 antibody (clone HIT3a, 1 µg/ml), anti-human CD28 antibody (clone CD28.2, 5 µg/ml) and varying amounts of Protein A (CD27L, 10-1000 ng/ml) or simply left in medium as control. After 3 days at 37° C. cells were fluorescently labbelled with anti-human CD27 and anti-human CD4 or anti-human CD8 antibodies. CD27 fluorescence was assessed on a guava easyCyte flow cytometer within CD4+ and CD8+ T cell populations.

When comparing (Table 10) T cells incubated with anti-CD3 and anti-CD28 antibodies to control cells left in medium alone, one observes a lower flourescent signal for CD27 indicating an activation-induced downregulation of the receptor. Importantly, this effect was even stronger and dose-dependent, when cells were co-incubated with the CD27 agonist (Protein A), which indicates a supplementary effect caused by the CD27 agonist (Protein A). As the agonist mimics the receptor-binding domain of the natural CD27 ligand (CD70), it is likely that the lower surface expression of CD27 is due to receptor internalisation upon binding of the CD27 agnonist (Protein A). These results clearly suggest a binding of the CD27 agonist (Protein A) to its receptor in vitro.

TABLE 10

CD27 agonist binding assay

| Stimulation | % of CD27 positive cells CD4 | % of CD27 positive cells CD8 |
|---|---|---|
| Medium | 70.04 | 70.14 |
| a-CD3+a-CD28 | 55.82 | 45.8 |
| a-CD3+a-CD28+CD27L 1 ng/ml | 51.98 | 38.41 |
| a-CD3+a-CD28+CD27L 10 ng/ml | 42.86 | 21.43 |
| a-CD3+a-CD28+CD27L 100 ng/ml | 9.43 | 5.34 |

Example 14

Antitumor Efficacy of PROTEIN A in Subcutaneous Syngeneic Colon Carcinoma MC38-CEA in Female C57Bl/6N Mice Material and Methods For the evaluation of the anti-tumor efficacy of PROTEIN A in the subcutaneously implanted syngeneic colon carcinoma model MC38-CEA, the study consisted in 3 experimental groups each containing 12 female C57Bl/6N mice 5-6 weeks of age.

All animals were implanted subcutaneously with 1×106 MCE38-CEA tumor cells in PBS in to the left flank of the animals, 8 days after tumor implantation when primary tumors reach a volume of 24.5-106.25 mm3, 36 tumor bearing animals were randomized into 3 groups (n=12). On the same day, treatment with 10 ml/kg vehicle control (PBS), 1 mg/kg and 10 mg/kg test compound PROTEIN A was initiated. Animals of all groups were treated intravenously (i.v) twice weekly on days 8, 12, 15 and 19. The study was terminated 24 hours (day 20) after last administration on day 19, animals sacrificed and a necropsy performed. At necropsy, animals were weight and anaesthetized by isoflurane. Blood samples were collected via retro bulbar vein puncture for preparation of serum. Thereafter, animals were killed by cervical dislocation, primary tumors were collected and wet weights and tumor volumes determined. Additionally, also spleens tissues were collected for analysis.

Results

The mean animal body weight of all study groups either remain stable or slightly increased during the course of the study. No major body weight losses could be observed.

Figure 9:
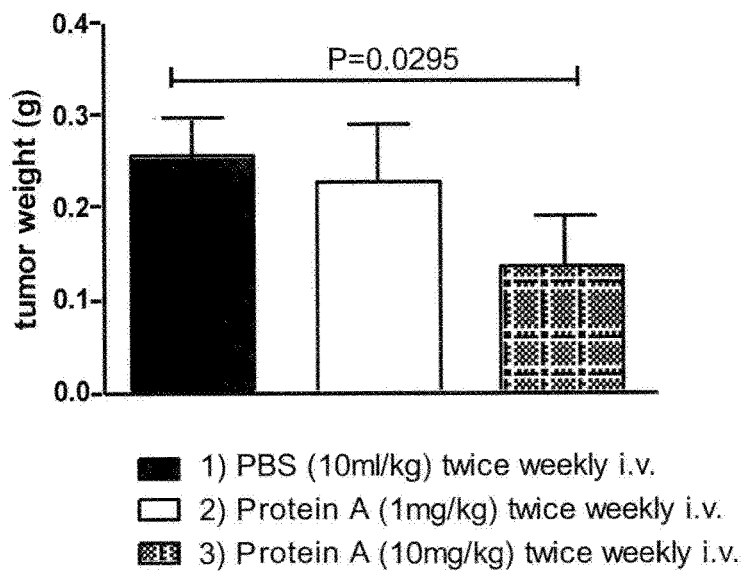
FIG. 9 Effect of PROTEIN A on subcutaneous syngeneic colon carcinoma model MC38-CEA female in female C57Bl/6N mice. Shown is wet tumor weight at necropsy.

PROTEIN A showed a dose-dependent inhibition of he primary tumor growth. Whereas tumor growth inhibition of PROTEIN A at dose of 1 mg/kg (25.8%) was noticeable although not statistically significant. APG 1293 at dose of 10 mg/kg produced a statistically significant tumor growth inhibition (48.2%) as measured in vivo on day 20. During necropsy, primary tumors were excised and tumor volumes and wet tumor weights determined. Wet tumor weight of high dose group (10 mg/kg) was significantly (P=0.0295) reduced compared to vehicle (FIG. 9). And tumor volume of high dose group was also significantly reduced compared to vehicle group. (FIG. 10).

Conclusion

PROTEIN A showed an in vivo dose-dependent antitumoral efficacy response in the subcutaneous syngeneic MC38-CEA colon carcinoma model in female C57Bl/6N mice.

Example 15

Antitumor Efficacy of PROTEIN A in Subcutaneous Syngeneic Colon Carcinoma CT26 in Female BALB/c Mice Material and Methods The anti-tumor efficacy of PROTEIN A was evaluated in a subcutaneously implanted syngeneic colon carcinoma CT26 in female BALB/c mice, the study consisted in 3 experimental groups each containing 10 females 5-6 weeks of age BALB/c mice. All animals were implanted subcutaneously with 5.0×105 CT26 tumor cells in cell culture media (RPMI w/o Phenol red) in to the right flank of the animals. On day 0 (11 days after tumor implantation), when primary tumors reach a volume of 23.5 mm3 to 132.7 mm3, 30 tumor bearing animals were randomized into 3 groups (n=10). On the same day, treatment with 10 ml/kg vehicle control (Group 1, PBS), 1 mg/kg (Group 2) and 10 mg/kg (Group3) test compound PROTEIN A was initiated. Animals of all groups were treated intravenously (i.v) twice weekly on days 11 (day 0), 15 (day 4) and 18 (day 7). The study was terminated on day 21 (day 10) 72 hours after last administration on day 18, animals sacrificed and a necropsy performed. At necropsy, animals were weight and anaesthetized by isoflurane. Blood samples were collected for preparation of serum. Thereafter, animals were killed by cervical dislocation, primary tumors were collected and wet weights determined. Additionally, also spleens tissues were collected for analysis.

Results

Figure 1:
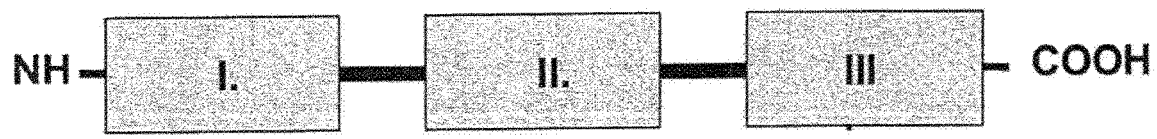
FIG. 1 Domain structure of a single-chain fusion polypeptide comprising three CD27L domains. I., II., III. Soluble CD27L domains.
Figure 1:
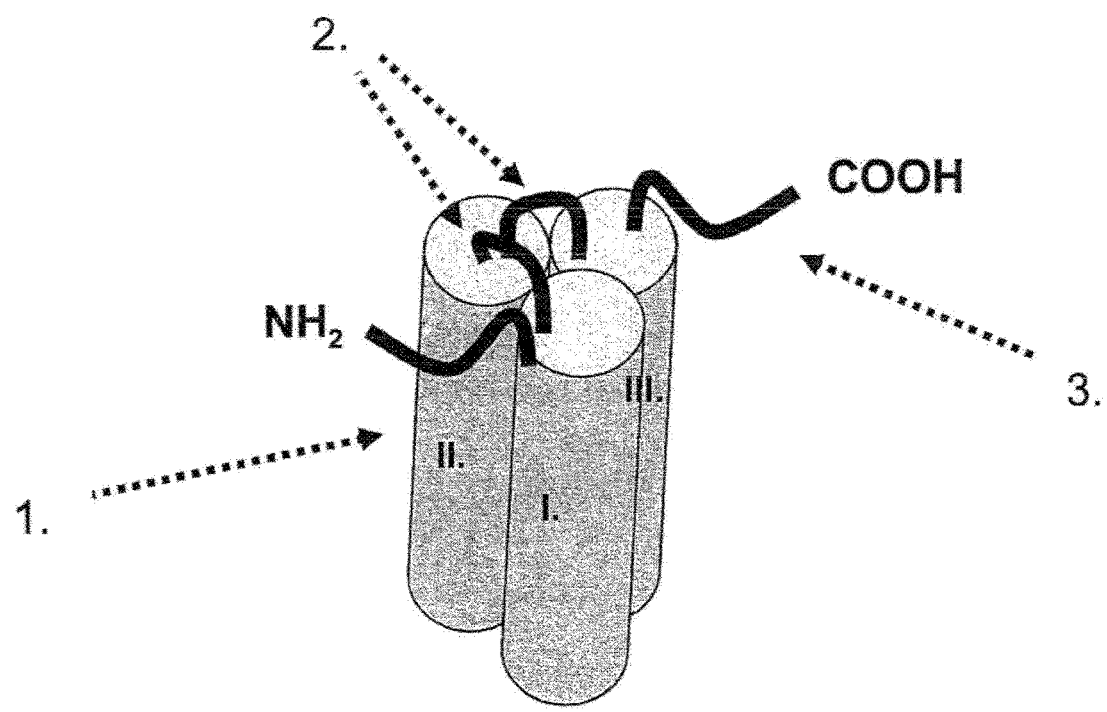

The mean animal body weight of all study groups either remain stable or slightly increased during the course of the study (FIG. 1). It was not influenced by treatment with PROTEIN A.

PROTEIN A induced tumor growth inhibition compared to vehicle control (PBS) in a subcutaneously implanted syngeneic colon carcinoma CT26 model in female BALB/c at any dose tested (1 mg/kg and 10 mg/kg). The effect of treatment with 1 mg/kg and 10 mg/kg PROTEIN A on estimated tumor volume was comparable and significant after 2nd PROTEIN A administration day 15 (day 4) onwards. PROTEIN A at dose of 1 mg/kg and 10 mg/kg produced a statistically significant tumor growth inhibition effect 84.7% (P<0.001) and 73.1% (P<0.001) respectively as measured in vivo on day 20.

Figure 12:
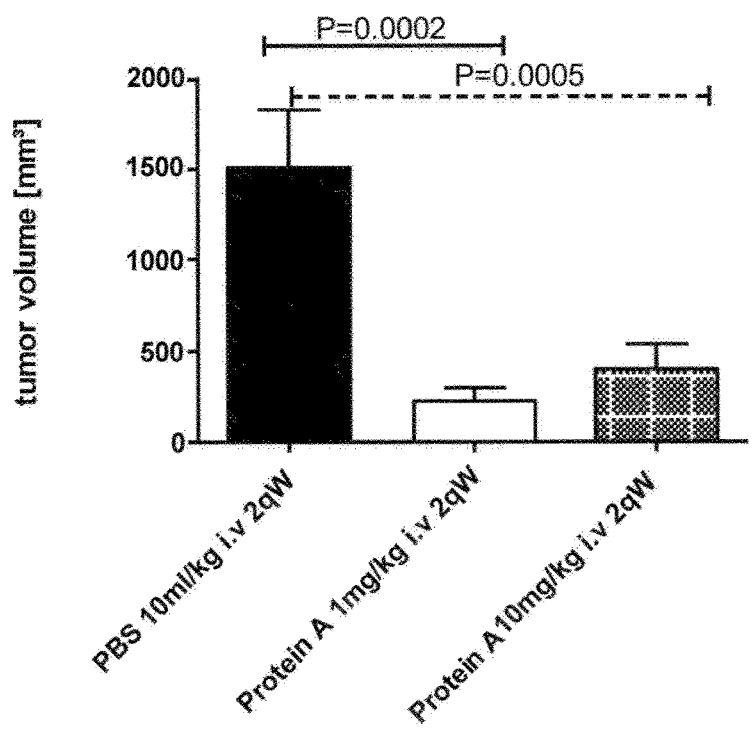

During necropsy, primary tumors were excised and tumor volumes and wet tumor weights determined. Wet tumor weight of low dose group (1 mg/kg) was significantly (P=0.0175) reduced compared to vehicle (FIG. 12). And tumor volume of high and low dose groupe were also significantly reduced (P=0.0005 and P=0.0002) compared to vehicle group. (FIG. 11).

Conclusion

PROTEIN A showed a highly significant tumor growth inhibition effect compared to vehicle control (PBS) in a subcutaneously implanted syngeneic colon carcinoma CT26 model in female BALB/c at the tested doses of 1 mg/kg and 10 mg/kg.

Example 16

CD27 Receptor Agonist Protein Enhances Murine Antigen-Specific CD8 Positive T Cell Clonal Expansion in Vivo T cells were isolated from the spleens and lymph nodes of "donor" OT-1 mice using a gentleMACS Octo Dissociator (Miltenyi Biotec). Cells were resuspended in PBS and injected intravenously in "recipient" C57Bl/6 mice. One day later ("day 0"), mice were injected intraperitoneally with 5 mg of chicken ovalbumin (OVA protein) and intravenously with hexavalent Protein A (0.1, 1 or 10 mg/kg), trimeric CD27 ligand (Protein X) (10 mg/kg) or vehicle control. At various time points, serial blood collection was performed. Spleens were also collected at the final time point.

Blood and spleen samples were lysed and stained with specific antibodies and Kb/OVA tetramer (H-2 Kb/SIINFEKL—specific for OT-1 cells, Biozol—MBL) and analyzed by flow cytometry with a BD Biosciences FACSCelesta BVR12, The Kb/OVA tetramer is a complex of mouse MHC class I plus the OVA peptide that binds specifically to the T cell receptor (TCR) of CD8 positive OT-1 T cells as well as any other OVA-specific CD8 positive T cells. Data analysis was performed with FlowJo 10.1 software (FlowJo, LLC). A minimum of ten thousand CD8+ T cells were recorded and examined per sample and there were three replicate animals per group. The percentage of Kb/OVA tetramer positive cells (OT-1 cells) as a percentage of total CD8 positive cells (plus average deviation) is presented in Table 11. As one would expect, the hexavalent CD27 receptor agonist but not the trimeric agonist enhanced the antigen-specific clonal expansion of the CD8 positive OT-1 T cells. This demonstrates a clear co-stimulatory effect exerted by the CD27 receptor agonist protein.

TABLE 11

OVA-specific CD8 positive OT-1 T cell clonal expansion following treatment with Protein A

| Time of blood sampling post treatment | Treatment (n = 3 per group) | | | | |
|---|---|---|---|---|---|
| | PBS | Protein A 10 mg/kg | ProteinA 1 mg/kg | Protein A 0.1 mg/kg | Trimeric ligand 10 mg/kg |
| | OT-1 as a percent of total CD8+ T cells - average (deviation) | | | | |
| Day 06 | 1% (0%) | 30% (4%) | 31% (3%) | 4% (2%) | 1% (0%) |
| Day 09 | 1% (0%) | 10% (1%) | 5% (1%) | 2% (1%) | 1% (0%) |
| Day 13 | 1% (1%) | 6% (1%) | 4% (1%) | 2% (3%) | 1% (0%) |

Example 17

Half-Life of the CO27 Receptor Agonist is Correlated to the Total Number of N-Linked Carbohydrates Molecule PROTEIN A is made up of two polypeptides covalently linked by three interchain disulfide bonds and comprises the K223G mutation in the hinge linker as well as the N297S mutation the Fc region (according to the EU numbering), resulting in a glycosylation of the CH2 domain. PROTEIN B has the same Fc-domain layout like PROTEIN A, but with linker element (iv) shorter and lacking N-linked glycosylation consensus site. PROTEIN-B is represented by SEQ ID NO: 47, but carries a C-terminal Streptag. PROTEIN C has the same layout as PROTEIN B but comprising in each of the soluble CD27L domains (i), (iii) and (v) the N63D mutation. PROTEIN-C is represented by SEQ ID NO: 43. PROTEIN D has the same layout as PROTEIN C comprising in each of the soluble CD27L domains (i), (iii) and (v) the N63D mutation, but with the N-terminal shortened soluble CD27L domains. PROTEIN-D is represented by SEQ ID NO: 45.

Therefore, as the mature proteins consists of two covalently linked polypeptides PROTEIN A comprises 16 N-linked carbohydrates, PROTEIN B comprises 14 N-linked carbohydrates and PROTEIN C and PROTEIN D both comprise 8 N-linked carbohydrates in total. The purified PROTEIN-A, -B, -C and -D were tested regarding their half-life in mice.

Female CD1 mice were administered with 10 mg/kg of PROTEIN A or -B or -C or -D as a single intravenous bolus injection. Whole blood was collected before application (pre-dose), and up to 312 hours after test item administration. Serum was prepared and samples were stored at −80° C. until determination of serum concentrations.

Quantitation of the PROTEIN A/-B/-C or -D concentrations in mouse serum was performed with an ELISA-assay detecting the CD27 agonists shown in table 8. Plates were coated with CD27-Fc. CD27-Ligand constructs specifically binding to its receptor CD27 were then detected via their Strep-Tag employing StrepTactin-HRP. ELISA assays were carried out using reference PROTEIN A, -B, -C or -D as calibration and control samples. The measured data of the standard concentrations were used to create calibration curves using a 5-parameter fit. This enabled the determination of the unknown PROTEIN A, -B, -C or -D concentrations in the respective mouse serum samples.

Pharmacokinetic parameters were calculated using the mean serum concentrations and the pharmacokinetic evaluation program PK Solutions Version 2.0 for non-compartmental pharmacokinetic data analysis (Summit Research Services, Montrose, Colo.). PK Solutions is an automated, Excel-based application, which computes pharmacokinetic parameters from concentration-time data obtained from analysis of e.g. biological samples following intravenous or extra-vascular routes of administration. PK Solutions calculates results without presuming any specific compartmental model.

The results from the pharmacokinetics evaluation are summarized in Table 12.

TABLE 12

Results of the exploratory PK study in CD1-mice: single intravenous dose of 10 mg/kg of PROTEIN A, -B -C and -D.

| | PROTEIN A (16 N-linked carbohydrates) | PROTEIN B (14 N-linked carbo-hydrates) | PROTEIN C (8 N-linked carbo-hydrates) | PROTEIN D (8 N-linked carbo-hydrates) |
|---|---|---|---|---|
| $t_{max}$ (h) | 0.083 | 0.083 | 0.083 | 0.083 |
| $C_{max}$ (µg/ml) | 150 | 158 | 125 | 149 |
| $AUC_{0-t}$ (µg * h/ml) | 557 | 190.1 | 191.4 | 203.9 |
| $AUC_{0-inf}$ (µg * h/ml) | 576.8 | 201.9 | 220.8 | 243.8 |
| Vd (ml/kg) | 350.8 | 1904.5 | 1741.5 | 1847.6 |
| Cl (ml/h) | 16.755 | 49.526 | 45.294 | 41.022 |
| $t_{1/2}$ E (h) | 14.5 | 20.3 | 26.6 | 31.2 |

The results show that PROTEIN A, -B, -C and -D have different half lifes of 14.5, 20.3 26.6 and 31.2 hours in mice. The half-life is inversely correlated to the total number of N-linked carbohydrates. The CD27 receptor agonist (PROTEIN D) with 8 N-linked carbohydrates but comprising the N-terminal shortened CD27L domains (i), (iii) and (v) confirms the data obtained with PROTEIN C. The short half-lifes observed constitute a favorable therapeutic option since a short co-stimulatory stimulus with CD27 receptor agonist proteins is desirable.

The invention claimed is:
1. A cluster of differentiation 27 (CD27) receptor agonist protein comprising a single-chain fusion polypeptide comprising:
   (i) a first soluble CD27L (CD27 ligand) domain,
   (ii) a first peptide linker having 3 to 8 amino acids,
   (iii) a second soluble CD27L domain,
   (iv) a second peptide linker having 3 to 8 amino acids, and
   (v) a third soluble CD27L domain,
   (vi) a hinge-linker selected from the group consisting of SEQ ID NOs: 16 and 19-24, and
   (vii) an antibody Fc fragment, wherein the antibody Fc fragment (vii) consists of the amino acid sequence of SEQ ID NO: 13 or amino acids 1-217 of SEQ ID NO: 13,
      wherein each of the soluble CD27L domains (i) (iii) and (v) consists of amino acids Glu51-Pro193 or Asp56-Pro193 of SEQ ID NO: 1.
2. The CD27 receptor agonist protein of claim 1, wherein the antibody Fc fragment (vii) is fused to the C-terminal end of the third CD27L domain (v) via a hinge-linker (vi).
3. The CD27 receptor agonist protein of claim 1, wherein the soluble CD27L domains (i), (iii) and (v) consist of amino acids Glu51—Pro193 of SEQ ID NO: 1.
4. The CD27 receptor agonist protein of claim 1, wherein the first and second peptide linkers (ii) and (iv) independently have one of the amino acid sequences of SEQ ID NOs: 2-12.
5. The CD27 receptor agonist protein of claim 4, wherein the first and the second peptide linkers (ii) and (iv) consist of the amino acid sequence according to SEQ ID NO: 2.
6. The CD27 receptor agonist protein of claim 1, which additionally comprises an N-terminal signal peptide domain.
7. The CD27 receptor agonist protein of claim 1, comprising the amino acid sequence selected from the group consisting of SEQ ID NOs: 15, 25, 27, 28, 30- 35, and 43-47.
8. A pharmaceutical composition comprising the CD27 receptor agonist protein of claim 1, and one or more pharmaceutically acceptable carriers, diluents, excipients, or adjuvants.
9. A CD27 receptor agonist protein comprising a single-chain fusion polypeptide comprising:
   (i) a first soluble CD27L domain,
   (ii) a first peptide linker having 3 to 8 amino acids,
   (iii) a second soluble CD27L domain,
   (iv) a second peptide linker having 3 to 8 amino acids, and
   (v) a third soluble CD27L domain,
   (vi) a hinge-linker selected from the group consisting of SEQ ID NOs: 16 and 19-24, and
   (vii) an antibody Fc fragment consisting of the amino acid sequence of SEQ ID NO:
   13 or amino acids 1-217 of SEQ ID NO: 13;
   wherein each of the soluble CD27L domains (i), (iii), and (v) consists of amino acids Glu51-Pro193 or Asp56-Pro193 of SEQ ID NO: 1, with one or more of the soluble CD27L domains (i), (iii), and (v) having a mutation at the amino acid position Glu51, Trp55, Asn63, Arg83, Arg122, Arg138, Arg144, His123, His124, His148, Asn170, Arg179, or Asp182 of SEQ ID NO: 1.
10. The CD27 receptor agonist protein of claim 9, wherein the Glu51 is mutated to a neutral amino acid.
11. The CD27 receptor agonist protein of claim 9, wherein one or more of the soluble CD27L domains (i), (iii), and (v) comprise a mutation of Asn63 or Asn170 to aspartate, serine or glycine.
12. The CD27 receptor agonist protein of claim 11, wherein the mutation is restricted to the soluble CD27L domains (iii) and (v).
13. A dimer comprising two polypeptides each having the amino acid sequence as set forth in SEQ ID NOs: 27, 30-35, or 43-47, fused via three disulfide bridges.
14. The dimer of claim 13, wherein the two polypeptides are covalently linked through three interchain disulfide bonds formed at:
   a) positions 457, 463, and 466 of SEQ ID NO: 27, 30, or 35, or
   b) positions 453, 459 and 462 of SEQ ID NO: 31, 43, or 47, or
   c) positions 450, 456 and 459 of SEQ ID NO: 32, or
   d) positions 436, 442 and 445 of SEQ ID NO: 33, or
   e) positions 454, 460 and 463 of SEQ ID NO: 34, or
   f) positions 442, 448 and 451 of SEQ ID NO: 44 or 46, or
   g) positions 438, 444 and 447 of SEQ ID NO: 45.
15. The dimer of claim 13, comprising one or more N-glycosylated asparagine residues selected from the group consisting of N149 and N300 of SEQ ID NO: 27, 30, 34, and 35, N149 of SEQ ID NO: 31, 32, 43, and 47, N145 of SEQ ID NO: 33, N144 and N290 of SEQ ID NO: 44 and 46, and N144 of SEQ ID NO: 45.
16. A CD27 receptor agonist protein comprising a single-chain fusion polypeptide comprising:
   (i) a first soluble CD27L domain,
   (ii) a first peptide linker having 3 to 8 amino acids,
   (iii) a second soluble CD27L domain,
   (iv) a second peptide linker having 3 to 8 amino acids, and
   (v) a third soluble CD27L domain,
   (vi) a hinge-linker selected from the group consisting of SEQ ID NOs: 16 and 19-24, and
   (vii) an antibody Fc fragment consisting of the amino acid sequence of SEQ ID NO: 13 or amino acids 1-217 of SEQ ID NO: 13;
   wherein the soluble CD27L domain (i) consists of amino acids Glu51-Pro193 of SEQ ID NO: 1, with the Glu51 being post-translationally modified to pyroglutamate, and each the soluble CD27L domains (iii) and (v) consists of amino acids Glu51-Pro193 or Asp56-Pro193 of SEQ ID NO: 1.

* * * * *